United States Patent
Crow et al.

(10) Patent No.: US 10,793,917 B2
(45) Date of Patent: Oct. 6, 2020

(54) METHOD AND KIT OF DETECTING THE ABSENCE OF MICRO-ORGANISMS

(71) Applicant: Momentum Bioscience Limited, Cardiff, Wales (GB)

(72) Inventors: Matthew A. Crow, Oxfordshire (GB); Helen V. Bennett, Buckinghamshire (GB); Daniel S. Wratting, Oxfordshire (GB); William H. Mullen, Berkshire (GB)

(73) Assignee: MOMENTUM BIOSCIENCE LIMITED, Wales (GB)

( * ) Notice: Subject to any disclaimer, the term of this patent is extended or adjusted under 35 U.S.C. 154(b) by 244 days.

(21) Appl. No.: 15/325,225

(22) PCT Filed: Jul. 10, 2015

(86) PCT No.: PCT/GB2015/052006
§ 371 (c)(1),
(2) Date: Jan. 10, 2017

(87) PCT Pub. No.: WO2016/005768
PCT Pub. Date: Jan. 14, 2016

(65) Prior Publication Data
US 2017/0240957 A1    Aug. 24, 2017

(30) Foreign Application Priority Data

Jul. 10, 2014 (GB) .................................. 1412316.0

(51) Int. Cl.
| C12P 19/34 | (2006.01) |
| C12Q 1/689 | (2018.01) |
| C12Q 1/6848 | (2018.01) |
| C12Q 1/04 | (2006.01) |

(52) U.S. Cl.
CPC .............. *C12Q 1/689* (2013.01); *C12Q 1/04* (2013.01); *C12Q 1/6848* (2013.01); *C12Q 2521/101* (2013.01); *C12Q 2525/101* (2013.01); *C12Q 2525/113* (2013.01); *G01N 2333/91245* (2013.01)

(58) Field of Classification Search
CPC ........ C12Q 1/04; C12Q 1/6848; C12Q 1/689; C12Q 2525/113; C12Q 2525/101; C12Q 2125/101; G01N 2333/91245
See application file for complete search history.

(56) References Cited

U.S. PATENT DOCUMENTS

| 5,939,262 A | 8/1999 | Pasloske et al. |
| 2013/0196318 A1 | 8/2013 | O'Hara et al. |
| 2013/0295576 A1 | 11/2013 | Yamamoto et al. |

FOREIGN PATENT DOCUMENTS

| JP | 2005269957 A | 10/2005 |
| WO | 90/06320 A1 | 6/1990 |
| WO | 2004020603 A2 | 3/2004 |
| WO | 2004097003 A2 | 11/2004 |
| WO | 2005069969 A2 | 8/2005 |
| WO | WO 2011130584 | * 4/2011 |
| WO | 2011130584 A2 | 10/2011 |
| WO | WO 2012/102208 | 8/2012 |
| WO | 2013/103744 A1 | 7/2013 |
| WO | 2013/155361 A1 | 10/2013 |

OTHER PUBLICATIONS

Zweitzig et al., Nucleic Acid Research, vol. 40, No. 14, e109, pp. 1-12, Apr. 11, (Year: 2012).*
Zweitzig et al., Transfusion, vol. 54, pp. 1642-1650, Nov. 5, (Year: 2013).*
Skerra et al., Nucleic acids Research, vol. 20, No. 14, pp. 3551-3554 (Year: 1992).*
Zweitzig, et al., "Characterization of a novel DNA polymerase activity assay enabling sensitive, quantitative and universal detection of viable microbes", Nucleic Acids Research, vol. 40, No. 14, 2012, pp. e109-e109.
Zweitzig, et al., "Feasibility of a Novel Approach for Rapid Detection of Simulated Bloodstream Infections via Enzymatic Template Generation and Amplification (TGA) eMediated Measurement of Microbial DNA Polymerase Activity", Journal of Molecular Diagnostics, vol. 15, No. 3, May 3, 2013.
Zweitzig, et al., "Measurement of Microbial DNA Polymerase Activity Enables Detection and Growth Monitoring of Microbes from Clinical Blood Cultures", PLOS One, vol. 8, No. 10, Oct. 14, 2013, p. e78488.
Zweitzig, et al., "A novel approach for rapid detection of bacterially contaminated platelet concentrates via sensitive measurement of microbial DNA polymerase activity", Transfusion, vol. 54, Jun. 2014, pp. 1642-1651.
International Preliminary Report on Patentability for PCT/GB2015/052006 dated Jun. 6, 2016.
International Search Report for PCT/GB2015/052006 dated Oct. 2, 2015.
Written Opinion for PCT/GB2015/052006 dated Oct. 2, 2015.
Combined Search and Examination Report for GB1516796.8 dated Jul. 26, 2016.
Japanese Office Action Summary, P253767.
Japanese Office Action P253767.
Japan Patent Office, Final Rejection for application 2017-521621, dated Jan. 7, 2020, with associate translation.

\* cited by examiner

*Primary Examiner* — Cynthia B Wilder
(74) *Attorney, Agent, or Firm* — Quarles & Brady LLP

(57) ABSTRACT

Methods of detecting the absence or presence of a micro-organism in a sample comprising: contacting the sample with a nucleic acid molecule which acts as a substrate for nucleic acid modifying activity of the micro-organism in the sample, incubating the thus contacted sample under conditions suitable for nucleic acid modifying activity; and specifically determining the absence or presence of a modified nucleic acid molecule resulting from the action of the nucleic acid modifying activity on the substrate nucleic acid molecule to indicate the absence or presence of the micro-organism. Corresponding kits are also provided.

23 Claims, 20 Drawing Sheets

Specification includes a Sequence Listing.

METHOD AND KIT OF DETECTING THE ABSENCE OF MICRO-ORGANISMS

CROSS-REFERENCE TO RELATED APPLICATIONS

The present application is the U.S. national stage of International Application PCT/GB2015/052006, filed on Jul. 10, 2015, which international application was published on Jan. 14, 2016 as International Publication No. WO2016/005768. The International Application claims priority to British Patent Application No. GB 1412316.0, filed on Jul. 10, 2014, the contents of which are incorporated herein by reference in their entireties.

FIELD OF THE INVENTION

The present invention relates generally to the field of detecting the absence or presence of microorganisms in a sample. The methods typically rely upon measuring microbial enzyme activity (if any) present in a sample and may relate to such methods which are capable of being performed using nucleic acid amplification techniques such as the polymerase chain reaction. The methods of the invention therefore enable determination of the absence and presence of microbial pathogens in samples such as un-purified blood, blood culture and other body fluids. This invention also relates to reagents for use in such methods, and to test kits comprising such reagents useful for carrying out the methods.

BACKGROUND TO THE INVENTION

Measuring the presence and levels of certain molecules which are associated with cell viability is important in a number of contexts. For example, measuring levels of ATP is useful in mammalian cells for growth analysis and toxicology purposes. Culture approaches can be used to detect small numbers of bacteria but such techniques require several days to complete, especially when attempting to detect small numbers of bacteria and also when detecting slower growing microorganisms.

Detection of adenylate kinase as an indicator of viability has also been proposed (Squirrell D J, Murphy M J, Leslie R L, Green J C D: A comparison of ATP and adenylate kinase as bacterial cell markers: correlation with agar plate counts. WO96/002665 describes a method for determining the presence and/or amount of microorganisms and/or their intracellular material present in a sample characterized in that the amount of adenylate kinase in the sample is estimated by mixing it with adenosine diphosphate (ADP), determining the amount of adenosine triphosphate (ATP) produced by the sample from this ADP, and relating the amount of ATP so produced to the presence/or amount of adenylate kinase and to microorganisms and/or their intracellular material, wherein the conversion of ADP to ATP is carried out in the presence of magnesium ions at a molar concentration sufficient to allow maximal conversion of ADP to ATP.

In WO2009/007719, ligases, in particular NAD– dependent ligases, are disclosed as a useful indicator of the presence of a (viable) microorganism in a sample. Ligases are enzymes which catalyze ligation of nucleic acid molecules. The ligation reaction requires either ATP or NAD+ as co-factor depending upon the ligase concerned. In this disclosure, the use of NAD– dependent ligase activity is utilized as an indicator of the presence of a (viable) microorganism in a sample.

WO2011/130584 describes a method for detection of viable microorganisms based on detection of DNA or RNA polymerases in which a sample is contacted with a nucleic acid substrate that acts as a substrate for microbial polymerase, incubated under conditions suitable for polymerase activity from intact microorganisms and any resulting nucleic acid product is determined using a nucleic acid amplification technique such as quantitative polymerase chain reaction. Such assays have been termed "ETGA assays", where ETGA stands for Enzymatic Template Generation and Amplification. A problem with ETGA assays for viable microorganisms in crude samples is the presence of contaminating polymerase activity outside the microorganisms arising from host (e.g. human) cells and dead microorganisms. The ETGA assay is unable to distinguish microorganism polymerase activity from that of the host or from dead microorganisms.

Applicant's co-pending application WO2010/119270 describes a method for removing enzyme activity (in this case, DNA ligase) outside intact microorganisms and this can be used also for removal of contamination nucleic acid polymerase activity.

DESCRIPTION OF THE INVENTION

However, the conditions used in WO2010/119270 for removing contaminating activity include incubation at high pH (around pH 11) for 20 min. Whilst useful, these conditions have been found by the inventors to be detrimental to particular bacterial strains such as certain clinical strains of H. influenzae.

It has further been discovered that treatment with high pH does not, in all cases, remove all the extramicrobial nuclease activity in samples such as blood culture and that this nuclease activity can have a detrimental effect on the assay by degrading the nucleic acid substrate used in the test. Nucleic acid amplification assays may include an internal control probe to monitor for the correct functioning of the amplification reaction (see for example WO2013/103744 where this is applied to a DNA polymerase assay similar to that of WO2011/130584). However, this internal control is added as part of the nucleic acid amplification reagent mix and would not detect prior nuclease activity. An additional problem with the method as described in WO2011/130584 is a relative lack of sensitivity in detecting yeast such as C. albicans and C. glabrata.

In rapid testing, the art has focused on detection of the presence of microorganisms rather than determining their absence. By "determining their absence" the applicants do not mean that the sample is necessarily sterile but may have an organism load that is sufficiently low as to be negative for practical purposes. For example, blood cultures are often taken from patients suspected of having bloodstream infections which can be associated with sepsis, a condition that can be rapidly fatal if left untreated. It is routine for clinical microbiology laboratories to incubate such specimens for at least five days before reporting a negative result, during which time the patients are often kept on broad spectrum antibiotics. Typically up to 90% of such patients are negative, and so a large number of patients are left for 5 days on antibiotic therapy that is not necessary for their condition. A faster method for determining a negative result (relative to a five-day blood culture) would be of significant value in reducing the cost of unnecessary antibiotic therapy and provide health benefits in terms of reducing the risks of *C. difficile* infection, antibiotic toxicity and lowering the rate of increase in antimicrobial resistance.

The inventors have devised and tested a range of improvements to existing ETGA assays with a view to optimising determination of the absence or presence of a micro-organism in a sample. The foundation of the invention is thus methods of detecting the absence or presence of a micro-organism in a sample comprising:
  (a) contacting the sample with a nucleic acid molecule which acts as a substrate for nucleic acid modifying activity of the micro-organism in the sample,
  (b) incubating the thus contacted sample under conditions suitable for nucleic acid modifying activity; and
  (c) specifically determining the absence or presence of a modified nucleic acid molecule resulting from the action of the nucleic acid modifying activity on the substrate nucleic acid molecule to indicate the absence or presence of the micro-organism. Various developments of this basic assay format are presented herein.

Accordingly, in a first aspect, the invention provides a method of detecting the absence or presence of a micro-organism in a sample comprising:
  (a) contacting the sample with a nucleic acid molecule which acts as a substrate for nucleic acid modifying activity of the micro-organism in the sample,
  (b) incubating the thus contacted sample under conditions suitable for nucleic acid modifying activity; and
  (c) specifically determining the absence or presence of a modified nucleic acid molecule resulting from the action of the nucleic acid modifying activity on the substrate nucleic acid molecule to indicate the absence or presence of the micro-organism, characterised in that the nucleic acid molecule is modified so as to protect it from nuclease activity.

In the context of the present invention, the nucleic acid molecule is pre-modified so as to protect it from nuclease activity i.e. the nucleic acid molecule is modified so as to protect it from nuclease activity before it is contacted with the sample in step (a).

The inventors have determined that protection of the substrate nucleic acid molecule from nuclease activity is advantageous in the context of the assays of the invention. More specifically as shown herein, incorporation of protected nucleic acid molecules into the methods of the invention improves sensitivity of detection. Any suitable means may be employed in order to protect the nucleic acid molecule from nuclease activity. Non-limiting examples include incorporation of methylation into the nucleic acid molecule, end modification such as protection of the 3' and/or 5' ends and incorporation of synthetic nucleotides. In specific embodiments, the synthetic nucleotides comprise phosphorothioate nucleotides and/or locked nucleic acid nucleotides. Preferably, the synthetic nucleotides are phosphorothioate nucleotides. In certain embodiments, the synthetic nucleotides replace at least one up to all of the nucleotides in the nucleic acid molecule.

The inventors have further determined that, compared to prior ETGA assays, increasing the concentration of the nucleic acid molecule in the reaction can lead to improved results. Thus, in a further aspect the invention provides a method of detecting the absence or presence of a micro-organism in a sample comprising:
  (a) contacting the sample with a nucleic acid molecule which acts as a substrate for nucleic acid modifying activity of the micro-organism in the sample,
  (b) incubating the thus contacted sample under conditions suitable for nucleic acid modifying activity; and
  (c) specifically determining the absence or presence of a modified nucleic acid molecule resulting from the action of the nucleic acid modifying activity on the substrate nucleic acid molecule to indicate the absence or presence of the micro-organism, characterised in that the nucleic acid molecule is added to the sample at a concentration of at least 2 nM but less than 50 nM.

Previously, in such assays, the nucleic acid substrate has been utilised at a concentration of 1 nM. The inventors have determined that increasing this concentration to less than 50 nM, such as 2 nM, 5 nM, 7.5 nM or 10 nM, results in improved sensitivity of detection. At or above 50 nM, the improved sensitivity is lost due to the increase in false positives resulting from the assay. The concentration as stated herein, is typically the concentration in the lysis mixture used to lyse the micro-organisms if present in the sample. Thus, step (a) of contacting the sample with the substrate nucleic acid molecule typically involves addition of the substrate in a lysis mixture which lyses the micro-organisms if present in the sample. Further details of the lysis reagent/mixture are provided herein.

The inventors have still further determined that increasing the concentration of free nucleotides in the reaction further serves to improve assay sensitivity. Accordingly, in some embodiments, the methods of the invention comprise adding to the sample deoxyribonucleotide triphosphates (dNTPs) at a concentration of more than 50 µM, such as 55 to 300 µM, or 60 to 250 µM, or 75 to 200 µM in particular at least 100 µM. The dNTPs may be added in either step (a) and/or step (b) in some embodiments. The concentration as stated herein, is typically the concentration in the lysis mixture used to lyse the micro-organisms if present in the sample. Thus, step (a) of contacting the sample with the substrate nucleic acid molecule typically involves addition of the substrate in a lysis mixture which lyses the micro-organisms if present in the sample, in which the lysis mixture contains the dNTPs. Further details of the lysis reagent/mixture are provided herein.

As discussed above, the inventors have discovered that while the high pH conditions adopted in WO2010/119270 for removing contaminating activity are useful, these conditions may be detrimental to particular bacterial strains such as certain clinical strains of *H. influenzae*. Accordingly, in a further aspect the invention provides a method of detecting the absence or presence of a micro-organism in a sample, the sample containing a non-microorganism source of nucleic acid modifying activity comprising:
  (a) treating the sample under high pH conditions for no more than 8 minutes in order to inhibit the non-microorganism source of nucleic acid modifying activity (whilst not affecting the nucleic acid modifying activity of the microorganism in the sample),
  (b) contacting the sample with a nucleic acid molecule which acts as a substrate for nucleic acid modifying activity of the micro-organism in the sample,
  (c) incubating the thus contacted sample under conditions suitable for nucleic acid modifying activity; and
  (d) specifically determining the absence or presence of a modified nucleic acid molecule resulting from the action of the nucleic acid modifying activity on the substrate nucleic acid molecule to indicate the absence or presence of the microorganism.

The duration of the high pH conditions is less than 20 minutes and may be not more than 10, 9, 8, 7, 6 or 5 minutes and may be around 5, 6, 7, 8, 9 or 10 minutes. In yet further embodiments, the treatment is carried out for between around 2 and 15 minutes, such as around 5 minutes. By "around" is meant plus or minus 30 seconds.

Any suitable reagent may be added to the sample in order to provide high pH conditions. In particular embodiments, the high pH conditions comprise contacting the sample with an alkali. In particular embodiments, NaOH or Na2CO3 is used. In specific embodiments, the concentration of the NaOH or Na2CO3 is around 5 mM or greater.

The high pH conditions typically inhibit the activity of nucleic acid modifying enzymes including ATP-dependent ligase and polymerases from non-microorganism sources such as mammalian cells, but do not inhibit the activity of the microbial ligases or polymerases. This may be due to the greater resistance of microbial enzymes to these conditions and/or to differential lysis conditions employed in the methods to ensure that only the non-microorganism enzymes are exposed to the high pH conditions. High pH is generally a pH of at least around 10, such as around 10, 11, 12, 13 or 14. Low pH is generally a pH of less than or equal to around 4, such as around 4, 3, 2, or 1. By "around" is meant 0.5 of a pH unit either side of the stated value. Altering the pH of the sample may be achieved using any suitable means, as would be readily appreciated by one skilled in the art. Microbial enzymes such as polymerases and ligases may be resistant to extremes of pH, whereas mammalian ligases may be inactivated under the same pH conditions. This permits selective detection of microbial ligases in a sample containing both mammalian cells and microbial cells. In specific embodiments, the conditions that inhibit the activity of non-microorganism nucleic acid modifying activity, such as ATP-dependent ligase, from mammalian cells but which do not inhibit the activity of the microorganism source of nucleic acid modifying activity, such as microbial ligases, comprise treating the sample with sodium hydroxide (NaOH) or sodium carbonate (Na2CO3). Such agents can readily be used, as shown herein, to increase the pH of the sample to high pH thus inactivating mammalian ligase activity whilst leaving the microbial (fungal and bacterial) ligases active. Suitable concentrations and volumes of the appropriate agent can be applied by a skilled person. In certain embodiments, however, the NaOH is at least around 5 mM NaOH. In some embodiments, the alkali concentration is no more than 10 mM, such as 5, 6, 7, 8, 9 or 10 mM.

In further embodiments, the pH is around 12 to inactivate mammalian nucleic acid modifying activity (such as polymerase and/or ATP-dependent ligase activity), but not microbial nucleic acid modifying activity (such as polymerase and/or ligase activity). In specific embodiments, pH conditions may be increased to at least around 11, or at least 11.2. This treatment may result in lysis of micro-organisms in the sample and thus lead to nucleic acid modifying activity (e.g. polymerase and/or ligase) release into the sample. This permits detection of nucleic acid modifying activity (e.g. polymerases and/or ligases) in the sample, originating from the micro-organism, without the need for a separate cell lysis step. Under these conditions, mammalian ligases (such as blood ATP-dependent ligases) are inactivated. However, typically the methods include a separate step for lysing microorganisms in the sample, as discussed in greater detail herein below.

In some embodiments, the treatment under high pH conditions is stopped by adding a reagent to lower the pH. Suitable reagents include a buffer and/or an acid. In specific embodiments, the buffer comprises a Tris-HCl buffer (e.g. pH 7.2 or 8). Other suitable agents for lowering the pH include acids such as hydrochloric acid (HCl) and sulphuric acid (H2SO4). These (and other) acids may be incorporated into a buffer as would be readily appreciated by one skilled in the art. These steps may be incorporated into step (a) of the method outlined above.

In specific embodiments, step (a) is performed at a temperature between around (to mean plus or minus 0.5 degrees) 15 and 30 degrees Celsius. In certain embodiments, step (a) is performed at room temperature. The entirety of the methods described herein may be performed at these temperatures.

In a more specific recitation of these methods, the invention further provides a method of detecting the absence or presence of a micro-organism in a sample, the sample containing a non-micro-organism source of nucleic acid modifying activity comprising:
(i) incubation of the sample with a reagent that lyses non-microorganisms if present in the sample but does not lyse microorganisms in the sample
(ii) optionally separation of the lysed cell material from the intact microorganisms (if any) in the sample
(iii) contacting the (separated) intact microorganisms (if any) in the sample with a high pH reagent and incubating for no more than 5 minutes in order to inhibit the non-microorganism source of nucleic acid modifying activity (whilst not affecting the nucleic acid modifying activity of the microorganism in the sample)
(iv) adding a pH lowering reagent in order to stop the incubation at high pH
(v) separation of the microorganisms if present in the sample from the pH modifying reagents
(vi) lysis of any separated microorganisms
(vi) contacting the sample with a nucleic acid molecule which acts as a substrate for nucleic acid modifying activity of the micro-organism in the sample,
(vii) incubating the thus contacted sample under conditions suitable for nucleic acid modifying activity; and
(viii) specifically determining the absence or presence of a modified nucleic acid molecule resulting from the action of the nucleic acid modifying activity on the substrate nucleic acid molecule to indicate the absence or presence of the micro-organism.

Step (ii) is an optional step because, in some embodiments, the lysed cell material does not need to be separated from the intact microorganisms. This is because step (iii) is used to inhibit the nucleic acid modifying activity found in the lysed cell material in any case.

By "lysed cell material" is meant the product of lysis of the non-microorganisms. This includes the cell membranes and intracellular content of the lysed cells.

More specifically, the methods may comprise the steps of:
(i) incubation of the sample with a reagent that lyses non-micro-organisms if present in the sample but does not lyse micro-organisms in the sample
(ii) centrifugation of the sample to form a pellet containing micro-organisms if present in the sample
(iii) removal of the supernatant from the pellet
(iv) re-suspending the pellet in a high pH reagent and incubating for no more than 8 minutes in order to inhibit the non-micro-organism source of nucleic acid modifying activity (whilst not affecting the nucleic acid modifying activity of the micro-organism in the sample)
(v) adding a pH lowering reagent in order to stop the incubation at high pH
(vi) a second centrifugation of the sample to form a pellet containing micro-organisms if present in the sample
(vi) removal of the supernatant from the pellet (vii) lysing any micro-organisms in the pellet
(viii) contacting the sample with a nucleic acid molecule which acts as a substrate for nucleic acid modifying activity of the micro-organism in the sample,
(ix) incubating the thus contacted sample under conditions suitable for nucleic acid modifying activity; and
(x) specifically determining the absence or presence of a modified nucleic acid molecule resulting from the action of the nucleic acid modifying activity on the substrate nucleic acid molecule to indicate the absence or presence of the micro-organism.

In specific embodiments, step (iii) or (iv) respectively, or the entire method is performed at a temperature between 15 and 30 degrees Celsius. Alternatively, step (iii) or (iv) respectively or the entire method may be performed at room temperature.

The reagent that lyses non-micro-organisms, in particular mammalian cells, if present in the sample but does not lyse micro-organisms in the sample may be any suitable reagent. The reagent may include a surfactant or detergent in some embodiments, such as a non-ionic detergent. Suitable examples include polyethylene glycol sorbitan monolaurate (Tween 20), for example at 5% w/v. The reagent may include a saponin, for example at 5% w/v. The reagent may include a metal halide salt, such as sodium chloride, for example at 8.5 g/l. The reagent may include a mixture of all three components. The sample may be mixed with the reagent under suitable conditions to ensure lysis of non-micro-organisms, in particular mammalian cells, if present in the sample but no (or insignificant) lysis of micro-organisms if present in the sample. The sample may be exposed to the reagent for a period of between around 5 and 30 minutes, such as 5, 10, 15, 20, 25 or 30 minutes. This step may be performed at any suitable temperature, for example between 15 and 30 degrees Celsius or at room temperature.

Where used, separation of the lysed cell material from the intact microorganisms (if any) in the sample may be performed by any suitable method. It may for example rely upon a form of affinity purification, such as an (polyclonal) antibody-based approach. It may rely upon filtration in some embodiments. Separation may rely upon centrifugation of the sample to form a pellet containing micro-organisms if present in the sample. Centrifugation of the sample may be performed at any suitable speed and for any suitable duration. For example, the sample may be centrifuged at a speed of between 3000 and 10000 g, such as around 7000 g or 7300 g. The sample may be centrifuged for a suitable period of time to ensure successful lysis of non-micro-organisms, in particular mammalian cells, if present in the sample but no or insignificant lysis of micro-organisms in the sample. This may be determined in conjunction with the speed of centrifugation. The time period may be between around 1 and 30 minutes, such as 1, 2, 3, 4, 5, 10, 15, 20, 25 or 30 minutes. This step may be performed at any suitable temperature, for example between 15 and 30 degrees Celsius or at room temperature. Following separation, the lysed cell material may be discarded (in the form of a supernatant) and the non-lysed cells retained (for example as a pellet).

The discussion provided above in respect of the more general methods applies mutatis mutandis here. Thus, in some embodiments the high pH reagent comprises NaOH or Na2CO3. In some embodiments, the concentration of the high pH reagent is around 5 mM or greater. In certain embodiments, the pH lowering reagent comprises a buffer or an acid, such as a Tris-HCl buffer. The buffer may be a pH 7.2 or 8 buffer in specific embodiments.

Following exposure to the pH modifying agent, any microorganisms in the sample are separated from the pH modifying conditions. This may be achieved by a second centrifugation of the sample to form a pellet containing micro-organisms if present in the sample, followed by removal of the supernatant from the pellet. Suitable centrifugation conditions are discussed above.

The method then requires lysis of any separated micro-organisms to permit detection of nucleic acid modifying activity. This may be achieved by addition of a lysis mixture. The lysis mixture is generally useful in the methods of the invention. The lysis mixture may include a specific mixture of components to ensure efficient lysis of microorganisms without adversely affecting nucleic acid modifying activity within the cells. The components may be selected from carrier/serum proteins such as BSA, surfactants/detergents, metal halide salts, buffers, chelators etc. In its basic form, the lysis mixture of the invention may include the following components:
1. A surfactant/detergent
2. Serum protein such as albumin (e.g. BSA)
3. Buffer
4. Nucleotides, such as dNTPs
5. Nucleic acid molecule (acting as a substrate in the assays of the invention).

A suitable lysis mixture is set forth below in table 1 and forms a separate aspect of the invention:

TABLE 1

| | Lysis mixture components | |
|---|---|---|
| L1 | Bovine serum albumin | 1.5% w/v |
| | Triton X100 | 1.5% v/v |
| | Tween 20 | 1.5% v/v |
| L2 | Ammonium sulphate | 2.64 g/L |
| | Magnesium sulphate heptahydrate | 0.98 g/L |
| | Potassium chloride | 1.5 g/L |
| | Tris-HCl, pH 8.0 | 40 mM |
| | dNTP (A, G, C, T) | 500 µM |
| L3 | ETGA substrate (nucleic acid molecule) | 0.001 µM-0.01 µM |
| | Tris-HCl, pH 8.5 | 20 mM |
| | KCl | 10 mM |
| | EDTA | 10 µM |

Exemplary concentrations of each component are listed but may be modified as would be readily appreciated by one skilled in the art.

Lysis may also require disruption of the cells. For example, the cells may be disrupted using the lysis mixture in combination with physical and/or enzymatic means. In some embodiments, physical disruption employs a disruptor. The disruptor may incorporate beads such as glass beads to lyse the cells. Suitable apparatus are commercially available and include the Disruptor Genie manufactured by Scientific Industries, Inc. Enzymatic disruption may require use of an agent selected from lysostaphin, lysozyme and/or lyticase in some embodiments.

As indicated in table 1, the step of contacting the sample with a nucleic acid molecule which acts as a substrate for nucleic acid modifying activity of the micro-organism in the sample may include adding the nucleic acid molecule to the lysis mixture.

The sample is then incubated under conditions suitable for nucleic acid modifying activity. This may involve incubation at an optimum temperature for nucleic acid modifying activity. For example, the sample may be incubated at a temperature between around 15 and 40 degrees Celsius, such as around 37 degrees Celsius. This may be for any suitable period of time, for example between 5 and 60 minutes, such as around 5, 10, 15, 20, 25 or 30 minutes. Following this, the nucleic acid modifying activity may be inactivated prior to the modified nucleic acid molecule detection step. This may be achieved by elevating the temperature, for example to a temperature above 60 degrees Celsius, such as 95 degrees Celsius for a suitable time period. This may be a relatively short time period such as 1, 2, 3, 4, 5, 10, 15 or more minutes.

Specifically determining the absence or presence of a modified nucleic acid molecule resulting from the action of the nucleic acid modifying activity on the substrate nucleic acid molecule to indicate the absence or presence of the micro-organism may be performed by any suitable method as discussed herein. Preferred methods are nucleic acid amplification based and may permit quantification of the nucleic acid modifying activity (and thus microorganisms) in the sample.

The inventors have also investigated the use of an internal positive control (IPC) molecule in the context of the ETGA methods. In particular, the invention may rely upon inclusion of the IPC with the substrate nucleic acid molecule so that the IPC is exposed to identical conditions. They have found that residual nuclease activity in the sample may affect the substrate added to the sample (particularly in the lysis mixture, as defined herein). Thus, there is an advantage in protecting the IPC from nuclease activity. Accordingly, the invention also provides a method of detecting the absence or presence of a micro-organism in a (liquid) sample, the sample potentially containing a non-micro-organism source of nuclease activity comprising:

(i) incubation of the sample with a reagent that lyses non-microorganisms if present in the sample but does not lyse microorganisms in the sample (ii) separation of the lysed cell material from the intact microorganisms (if any) in the sample and/or inactivation of the lysed cell material (iii) lysing any microorganisms following the separation and/or inactivation (iv) contacting the sample with a nucleic acid molecule which acts as a substrate for nucleic acid modifying activity of the micro-organism in the sample together with an internal positive control (IPC) nucleic acid molecule, (v) incubating the thus contacted sample under conditions suitable for nucleic acid modifying activity; and (vi) specifically determining the absence or presence of a modified nucleic acid molecule resulting from the action of the nucleic acid modifying activity on the substrate nucleic acid molecule to indicate the absence or presence of the micro-organism, characterised in that the IPC nucleic acid molecule is modified so as to protect it from nuclease activity.

Separation in step (ii) is an optional step because, in some embodiments, the lysed cell material does not need to be separated from the intact microorganisms. In some embodiments, an alternative or additional step of inactivating the nucleic acid modifying activity found in the lysed cell material is performed. Any suitable inactivation technique may be employed as discussed herein. For example, inactivation may be of nucleic acid modifying activity and/or nuclease activity in the lysed cell material. Inactivation may be achieved using any suitable means, for example high pH treatment as discussed herein. The fact that the microorganisms remain intact may protect them from an inactivation treatment.

Similarly, the invention also provides a method of detecting the absence or presence of a micro-organism in a (liquid) sample, the sample potentially containing a non-micro-organism source of nuclease activity comprising:

(a) centrifugation of the sample to form a pellet containing micro-organisms if present in the sample (b) removal of the supernatant from the pellet (c) lysing any micro-organisms in the pellet (d) contacting the sample with a nucleic acid molecule which acts as a substrate for nucleic acid modifying activity of the micro-organism in the sample together with an internal positive control (IPC) nucleic acid molecule, (e) incubating the thus contacted sample under conditions suitable for nucleic acid modifying activity; and (f) specifically determining the absence or presence of a modified nucleic acid molecule resulting from the action of the nucleic acid modifying activity on the substrate nucleic acid molecule to indicate the absence or presence of the micro-organism, characterised in that the IPC nucleic acid molecule is modified so as to protect it from nuclease activity.

The protected IPC is particularly advantageous in the context of use of protected substrate molecules. Accordingly, in some embodiments, the (substrate) nucleic acid molecule is also modified so as to protect it from nuclease activity. This ensures that both nucleic acid molecules are protected and subjected to the same conditions. Any suitable means may be employed in order to protect the nucleic acid molecules from nuclease activity. Non-limiting examples include incorporation of methylation into the nucleic acid molecules, end modification such as protection of the 3' and/or 5' ends and incorporation of synthetic nucleotides. In specific embodiments, the synthetic nucleotides comprise phosphorothioate nucleotides and/or locked nucleic acid nucleotides. Preferably, the synthetic nucleotides are phosphorothioate nucleotides. In certain embodiments, the synthetic nucleotides replace at least one up to all of the nucleotides in the nucleic acid molecules. In specific embodiments, the IPC and substrate nucleic acid molecule are modified in the same manner. This is with a view to providing as equal as possible protection from nuclease activity.

In the context of the present invention, if the IPC is modified so as to protect it from nuclease activity, the IPC is pre-modified so as to protect it from nuclease activity i.e. the IPC is modified so as to protect it from nuclease activity before it is contacted with the sample.

The invention also contemplates using the IPC in order to monitor potential contaminating nuclease activity in the sample. Accordingly, the invention also provides a method of detecting the absence or presence of a micro-organism in a (liquid) sample, the sample potentially containing a non-micro-organism source of nuclease activity comprising:

(i) incubation of the sample with a reagent that lyses non-microorganisms if present in the sample but does not lyse micro-organisms in the sample (ii) separation of the lysed cell material from the intact microorganisms (if any) in the sample and/or inactivation of the lysed cell material (iii) lysing any microorganisms following the separation and/or inactivation (iv) contacting the sample with a nucleic acid molecule which acts as a substrate for nucleic acid modifying activity of the micro-organism in the sample together with an internal positive control (IPC) nucleic acid molecule, (v) incubating the thus contacted sample under conditions suitable for nucleic acid modifying activity; and
(vi) specifically determining the absence or presence of a modified nucleic acid molecule resulting from the action of the nucleic acid modifying activity on the substrate nucleic acid molecule to indicate the absence or presence of the micro-organism, characterised in that the IPC nucleic acid molecule is susceptible to nuclease activity and is used to identify contaminating nuclease activity in the pellet.

Separation in step (ii) is an optional step because, in some embodiments, the lysed cell material does not need to be separated from the intact microorganisms. In some embodiments, an alternative or additional step of inactivating the nucleic acid modifying activity found in the lysed cell material is performed. Any suitable inactivation technique may be employed as discussed herein. For example, inactivation may be of nucleic acid modifying activity and/or nuclease activity in the lysed cell material. Inactivation may be achieved using any suitable means, for example high pH treatment as discussed herein. The fact that the microorganisms remain intact may protect them from an inactivation treatment.

Similarly, there is further provided a method of detecting the absence or presence of a micro-organism in a (liquid) sample, the sample potentially containing a non-microorganism source of nuclease activity comprising:
(a) centrifugation of the sample to form a pellet containing micro-organisms if present in the sample
(b) removal of the supernatant from the pellet
(c) lysing any micro-organisms in the pellet
(d) contacting the sample with a nucleic acid molecule which acts as a substrate for nucleic acid modifying activity of the micro-organism in the sample together with an internal positive control (IPC) nucleic acid molecule,
(e) incubating the thus contacted sample under conditions suitable for nucleic acid modifying activity; and
(f) specifically determining the absence or presence of a modified nucleic acid molecule resulting from the action of the nucleic acid modifying activity on the substrate nucleic acid molecule to indicate the absence or presence of the micro-organism, characterised in that the IPC nucleic acid molecule is susceptible to nuclease activity and is used to identify contaminating nuclease activity in the pellet.

Typically, steps (iii) and (iv) or (c) and (d) are performed together.

In specific embodiments, the (substrate) nucleic acid molecule used in the methods of the invention is at least partially double stranded and comprises uracil residues in the complementary strand and the step of specifically determining the absence or presence of the modified nucleic acid molecule comprises adding Uracil DNA Glycosylase (UDG) to the sample in order to degrade the uracil residues in the complementary strand.

In certain embodiments, the first strand of the partially double stranded (substrate) nucleic acid molecule comprises (or consists of) synthetic nucleotides (e.g. phosphorothioate nucleotides) and the second (complementary) strand comprises (or consists of) uracil residues and, optionally, synthetic nucleotides (e.g. phosphorothioate nucleotides). Preferably, the double stranded region encompasses the 3' end regions of the first and second (complementary) strands. Preferably, the double stranded region is at least 5, at least 10, at least 15, at least 20 or at least 25 nucleotides; optionally, the double stranded region is no more than 50 nucleotides. The first strand may be extended during an incubation step, as described herein, using unprotected (or standard) dNTPs by the polymerase activity of a microorganism in the sample to form an extended first strand that comprises unprotected (or standard) nucleotides. This step relies upon using the second strand as template (upstream of the region of complementarity between the first and second strands). Following the incubation step, the second (complementary) strand may be degraded by adding Uracil DNA Glycosylase (UDG) to the sample leaving the extended first strand as a single stranded molecule comprising synthetic nucleotides and unprotected nucleotides. Following degradation of the second strand, the extended first strand of the (substrate) nucleic acid molecule may be detected in an amplification step. The inventors have found that the use of a partially double stranded (substrate) nucleic acid molecule as described above improves the detection of a microorganism in the sample.

In certain embodiments, the IPC nucleic acid molecule comprises identical primer binding sites to the nucleic acid molecule such that there is competition for primer binding (in step (vi) or (f) of the method).

In further embodiments, a nucleic acid probe is added (in step (vi) or (f)) which binds to a target probe sequence within the nucleic acid molecule. Typically, the probe binds to the sense strand of the nucleic acid molecule. In other embodiments, a further nucleic acid probe is added in step (vi) or (f) respectively which binds to a target probe sequence within the IPC nucleic acid molecule. In specific embodiments, the nucleic acid probe does not bind to the IPC nucleic acid molecule and the further nucleic acid probe does not bind to the nucleic acid molecule. The nucleic acid probe and/or further nucleic acid probe may be labelled. Preferably, they are differently labelled.

In specific embodiments, the complementary strand of the nucleic acid molecule comprises a modification at the 3' end to prevent extension. This modification may comprise incorporation of a non-extendible nucleotide. In specific embodiments, the non-extendible nucleotide is a dideoxy nucleotide triphosphate (ddNTP), such as dideoxyCytidine.

In the methods in which the IPC is susceptible to nuclease activity, the (substrate) nucleic acid molecule may be modified so as to protect it from nuclease activity. Suitable modifications are discussed herein and may be selected from incorporation of methylation, protection of the 3' and/or 5' ends, incorporation of synthetic nucleotides. Examples of synthetic nucleotides comprise phosphorothioate nucleotides and/or locked nucleic acid nucleotides. Preferably, the synthetic nucleotides are phosphorothioate nucleotides.

The various developments of the basic assay format can advantageously be combined to produce a particularly specific and sensitive method. Accordingly, the invention further provides a method of detecting the absence or presence of a micro-organism in a sample, the sample containing a non-micro-organism source of nucleic acid modifying activity comprising:
(i) incubation of the sample with a reagent that lyses non-microorganisms if present in the sample but does not lyse microorganisms in the sample
(ii) optionally separation of the lysed cell material from the intact microorganisms (if any) in the sample
(iii) contacting the (separated) intact microorganisms (if any) in the sample with a high pH reagent and incubating for no more than 5 minutes in order to inhibit the non-micro-organism source of nucleic acid modifying activity (whilst not affecting the nucleic acid modifying activity of the microorganism in the sample)

(iv) adding a pH lowering reagent in order to stop the incubation at high pH
(v) separation of the microorganisms if present in the sample from the pH modifying reagents
(vi) lysis of any separated microorganisms
(vii) contacting the sample with a nucleic acid molecule which acts as a substrate for nucleic acid modifying activity of the micro-organism in the sample,
(viii) incubating the thus contacted sample under conditions suitable for nucleic acid modifying activity; and
(ix) specifically determining the absence or presence of a modified nucleic acid molecule resulting from the action of the nucleic acid modifying activity on the substrate nucleic acid molecule to indicate the absence or presence of the microorganism, wherein the nucleic acid molecule is modified so as to protect it from nuclease activity.

Step (ii) is an optional step because, in some embodiments, the lysed cell material does not need to be separated from the intact microorganisms. This is because step (iii) is used to inhibit the nucleic acid modifying activity found in the lysed cell material in any case.

Similarly, the invention further provides a method of detecting the absence or presence of a microorganism in a sample, the sample containing a non-microorganism source of nucleic acid modifying activity comprising:
(a) incubation of the sample with a reagent that lyses non-microorganisms if present in the sample but does not lyse micro-organisms in the sample
(b) centrifugation of the sample to form a pellet containing microorganisms if present in the sample
(c) removal of the supernatant from the pellet
(d) re-suspending the pellet in a high pH reagent and incubating for no more than 5 minutes in order to inhibit the non-micro-organism source of nucleic acid modifying activity (whilst not affecting the nucleic acid modifying activity of the microorganism in the sample)
(e) adding a pH lowering reagent in order to stop the incubation at high pH
(f) a second centrifugation of the sample to form a pellet containing micro-organisms if present in the sample
(g) removal of the supernatant from the pellet
(h) lysing any micro-organisms in the pellet
(i) contacting the sample with a nucleic acid molecule which acts as a substrate for nucleic acid modifying activity of the micro-organism in the sample,
(j) incubating the thus contacted sample under conditions suitable for nucleic acid modifying activity; and
(k) specifically determining the absence or presence of a modified nucleic acid molecule resulting from the action of the nucleic acid modifying activity on the substrate nucleic acid molecule to indicate the absence or presence of the micro-organism, wherein the nucleic acid molecule is modified so as to protect it from nuclease activity.

Thus, these methods represent a combination of the other methods described herein. Accordingly, all relevant embodiments apply to this overall method mutatis mutandis. For example, as for other embodiments in which the nucleic acid is modified, the modification may be selected from incorporation of methylation, protection of the 3' and/or 5' ends, incorporation of synthetic nucleotides. The synthetic nucleotides may comprise phosphorothioate nucleotides and/or locked nucleic acid nucleotides. Preferably, the synthetic nucleotides are phosphorothioate nucleotides.

In particular embodiments, the nucleic acid molecule is added to the sample at a concentration of at least 2 nM and less than 50 nM (e.g. 2 nM to 25 nM, 5 nM to 15 nM, or 7.5 to 12.5 nM), such as 2 nM, 5 nM, 7.5 nM or 10 nM. The nucleic acid molecule may be included in the lysis mixture used in step (vi) or (h) of the method (i.e. the specified concentration is the concentration in the lysis mixture). Thus, steps (vi) and (vii) or (h) and (i) respectively may effectively be combined as a single step in some embodiments. The lysis mixture may be as specified in Table 1 or as discussed elsewhere in this disclosure.

The method may similarly comprise adding to the sample deoxyribonucleotide triphosphates at a concentration of more than 50 µM, preferably at least 100 µM, such as 55 to 300 µM, or 60 to 250 µM, or 75 to 200 µM. Again, the dNTPs may be included in the lysis mixture used in step (vi) or (h) of the method (i.e. the specified concentration is the concentration in the lysis mixture). Thus, steps (vi) and (vii) or (h) and (i) respectively may effectively be combined as a single step in some embodiments.

As discussed in greater detail hereinabove, the high pH reagent may be or comprise NaOH or Na2CO3. In specific embodiments, the concentration of the high pH reagent is around 5 mM or greater. The pH lowering reagent may comprise a buffer or an acid, such as a Tris-HCl buffer (e.g. pH 7.2 or 8). In specific embodiments, step (iii) or (d) is performed at a temperature between 15 and 30 degrees Celsius or is performed at room temperature. Each and/or all steps of the method may be performed at a temperature between 15 and 30 degrees Celsius or at room temperature in some embodiments. Where nucleic acid amplification steps such as PCR are utilised, those steps will need to be performed at appropriate temperatures as detailed herein and understood by the skilled person.

In specific embodiments, a nuclease susceptible IPC may be employed. Thus, step (vii) or (i) respectively may comprise contacting the sample with a nucleic acid molecule which acts as a substrate for nucleic acid modifying activity of the micro-organism in the sample together with an internal positive control (IPC) nucleic acid molecule, wherein the IPC nucleic acid molecule is susceptible to nuclease activity and is used to identify contaminating nuclease activity in the pellet.

Alternatively, a nuclease resistant IPC may be employed. Thus, step (vii) or (i) respectively may comprise contacting the sample with a nucleic acid molecule which acts as a substrate for nucleic acid modifying activity of the micro-organism in the sample together with an internal positive control (IPC) nucleic acid molecule, wherein the IPC nucleic acid molecule is modified so as to protect it from nuclease activity. Suitable modifications are discussed in greater detail herein and may be selected from incorporation of methylation, protection of the 3' and/or 5' ends, incorporation of synthetic nucleotides. The synthetic nucleotides may be or comprise phosphorothioate nucleotides and/or locked nucleic acid nucleotides. Preferably, the synthetic nucleotides are phosphorothioate nucleotides. If both molecules are modified, it is preferable that they are modified in the same or similar manner such that the nuclease resistance is comparable. This permits the IPC to perform a most useful comparator role to determine the impact of nuclease activity on the substrate molecule.

As already mentioned, in some embodiments, steps (vi) and (vii) or (h) and (i) are performed together. Here, the nucleic acid molecule is added to the sample together with a lysis reagent to form a lysis mixture.

As discussed in further detail herein, which discussion applies mutatis mutandis, the detection of the modified nucleic acid molecule may be detected by a range of methods including by sequencing or nucleic acid amplification. In specific embodiments, step (ix) or (k) respectively comprises a nucleic acid amplification step.

Any suitable nucleic acid molecule may be employed. In some embodiments, the nucleic acid molecule incorporates uracil residues. In specific embodiments, the nucleic acid molecule is at least partially double stranded and comprises uracil residues in the complementary strand. In such embodiments, the methods (and in particular step (ix) or (k) of the respective method) may comprise adding Uracil DNA Glycosylase (UDG) to the sample in order to degrade the uracil residues in the complementary strand. In further embodiments, the complementary strand of the nucleic acid molecule comprises a modification at the 3' end to prevent extension. By "extension" is meant the addition of further nucleotides. Any suitable modification may be employed. In specific embodiments, the modification is or comprises incorporation of a non-extendible nucleotide. Any suitable non-extendible nucleotide may be employed. For example, the non-extendible nucleotide may be or comprise a dideoxy nucleotide triphosphate (ddNTP), such as dideoxyCytidine.

In certain embodiments, the IPC nucleic acid molecule comprises identical primer binding sites to the nucleic acid molecule such that there is competition for primer binding during the step of detection of the modified nucleic acid molecule (in step (ix) or (k)).

As discussed herein there are a range of amplification technologies available, many of which rely upon probes (such as hydrolytic or hairpin probes). Thus, in some embodiments the methods include use of a probe, in particular in step (ix) or (k). In specific embodiments, a nucleic acid probe is added in step (ix) or (k) of the method. This probe binds to a target probe sequence within the (sense strand of the) nucleic acid molecule. By "binds" is meant hybridization under the conditions applied to the method as would be readily appreciated by one skilled in the art. In some embodiments, a further nucleic acid probe is utilised, for example added in step (ix) or (k), which binds to a target probe sequence within the IPC nucleic acid molecule. In specific embodiments, the nucleic acid probe does not bind to the IPC nucleic acid molecule and the further nucleic acid probe does not bind to the (substrate) nucleic acid molecule. The probes and nucleic acid molecules (IPC or substrate) can be designed to avoid unwanted cross-hybridization using techniques and tools (such as online design tools) known in the art.

The nucleic acid probe and/or further nucleic acid probe may be labelled. In specific embodiments, the nucleic acid probe and further nucleic acid probe are differently labelled. For example, they may be labelled with fluorophores which have different wavelengths of maximal emission. Suitable pairs of labels can be readily selected by one skilled in the art, for example FAM and Texas Red may be used as different labels.

According to all aspects of the invention, the nucleic acid modifying activity may be any activity that is useful for indicating microorganism viability. The nucleic acid modifying activity is an enzymatic activity provided by the microorganism. Examples include polymerase and/or ligase activity. Preferably, the nucleic acid modifying activity is polymerase activity. Polymerase activity may comprise DNA and/or RNA polymerase activity. Preferably the polymerase activity is DNA and/or RNA polymerase activity. Ligase activity may be ATP or NAD dependent. Other nucleic acid modifying activities relevant to viability may alternatively be measured such as phosphatase, kinase and/or nuclease activity.

Preferably, the action of the nucleic acid modifying activity on the substrate nucleic acid molecule produces an extended nucleic acid molecule.

Suitable substrate molecules are described herein in detail. Reference can also be made to WO2011/130584, WO2010/119270 and WO2009/007719 (the pertinent disclosures of which are hereby incorporated) where suitable substrate molecules useful for detecting nucleic acid modifying activity are disclosed. In the case of phosphatase activity, suitable nucleic acid molecules are disclosed in WO2006/123154, which disclosure is hereby incorporated by reference.

The substrate nucleic acid molecules for use in the methods, and inclusion in the kits, of the invention, must be of sequence and structure such that the NAD- dependent ligase can act on the molecule to produce a detectable ligated (novel) nucleic acid molecule.

Suitable substrate nucleic acid molecules for use in the invention are described in more detail in the experimental section below. Thus, the substrate may be comprised of the following molecules:

AS
(SEQ ID NO: 6)
Uaggcgucggugacaaacggccagcguuguugucucu-DDC (3' terminal is a dideoxy-C)

S1
(SEQ ID NO: 7)
Gccgatatcggacaacggccgaactgggaaggcgagactgaccgaccgat aagctagaacagagagacaacaac This is an example of a substrate nucleic acid molecule which incorporates uracil residues in the antisense strand. The nucleic acid molecule is partially double stranded and comprises uracil residues in the complementary strand. This permits Uracil DNA Glycosylase (UDG) to degrade the uracil residues in the complementary strand following extension and thus prevents the substrate molecule from being non-specifically amplified in the absence of extension (i.e. in the absence of nucleic acid modifying activity in the sample). In further embodiments, the complementary strand of the nucleic acid molecule comprises a modification at the 3' end to prevent extension. By "extension" is meant the addition of further nucleotides. Any suitable modification may be employed. In specific embodiments, the modification is or comprises incorporation of a non-extendible nucleotide. Any suitable non-extendible nucleotide may be employed. For example, the non-extendible nucleotide may be or comprise a dideoxy nucleotide triphosphate (ddNTP), such as dideoxyCytidine as shown in SED ID NO: 6.

It is noted that variants of these sequences may be utilised in the present invention. For example, additional flanking sequences may be added. Alternative ddNTPs may be employed. Variant sequences may have at least 90%, at least 91%, at least 92%, at least 93%, at least 94%, at least 95%, at least 96%, at least 97%, at least 98%, or at least 99% nucleotide sequence identity with the nucleotide sequences of the substrate nucleic acid molecules set forth as SEQ ID NOs 6 and 7. The nucleic acid molecules may incorporate synthetic nucleotide analogues as appropriate or may be RNA or PNA based for example, or mixtures thereof. Suitable modifications, for example, to protect from nuclease activity, are described herein. They may be labelled, such as using a fluorescent label, or FRET pair, in certain embodiments to facilitate detection. Suitable detection methods are described herein.

Thus, the (substrate) nucleic acid molecules include any natural nucleic acid and natural or synthetic analogues that are capable of being acted upon by nucleic acid modifying activity in order to generate a (novel detectable) nucleic acid molecule. The substrate may be extended and/or ligated in specific embodiments. Combinations of nucleic acid substrate molecules may be employed to permit detection of polymerase and ligase activity in some embodiments.

Preferably, the nucleic acid substrate is present in excess, and in particular in large molar excess, over the nucleic acid modifying activity (provided by the microorganisms) in the sample. This is an important technical distinction over prior art methods. Because a novel extended or ligated nucleic acid molecule is detected, only the presence of this molecule in the sample is essential for the detection methods to work effectively. Thus, it is not detrimental to the methods of the invention if other nucleic acid molecules are present in the sample such as from the microorganisms to be detected or from mammalian or other sources which may be found in the sample to be tested for example.

In some embodiments, the substrate and/or primers may incorporate complementary non-naturally occurring molecules which can base pair with each other, to avoid non-specific detection of genomic DNA. As an example, pyDAD and puADA may be incorporated into primers and substrate molecules as appropriate (Sismour et al., Nucleic Acids Research, 2004, Vol. 32, No. 2: 728-735).

As also discussed herein, the methods of the invention may incorporate an IPC molecule. Any suitable IPC may be employed according to the requirements of the method. As an example, the following IPC may be used in the invention:

(SEQ ID NO: 3)
gcc gat atc gga caa cgg ccg aac tgg gaa ggc gag
atc agc agg cca cac gtt aaa gac aga gag aca aca
acg ctg gcc gtt tgt cac cga cgc cta In all methods of the invention specifically determining the absence or presence of the modified nucleic acid molecule may comprise, consist essentially of or consist of a nucleic acid amplification step. This serves to make the methods of the invention maximally sensitive. Such amplification techniques are well known in the art, and include methods such as PCR, NASBA (Compton, 1991), 3SR (Fahy et al., 1991), Rolling circle replication, Transcription Mediated Amplification (TMA), strand displacement amplification (SDA) Clinical Chemistry 45: 777-784, 1999, the DNA oligomer self-assembly processes described in U.S. Pat. No. 6,261,846 (incorporated herein by reference), ligase chain reaction (LCR) (Barringer et al., 1990), selective amplification of target polynucleotide sequences (U.S. Pat. No. 6,410,276), arbitrarily primed PCR (WO 90/06995), consensus sequence primed PCR (U.S. Pat. No. 4,437,975), invader technology, strand displacement technology and nick displacement amplification (WO 2004/067726). The list above is not intended to be exhaustive. Any nucleic acid amplification technique may be used provided the appropriate nucleic acid product is specifically amplified. Similarly, sequencing based methodologies may be employed in some embodiments to include any of the range of next generation sequencing platforms.

Amplification is achieved with the use of amplification primers specific for the sequence of the modified nucleic acid molecule which is to be detected. In order to provide specificity for the nucleic acid molecules primer binding sites corresponding to a suitable region of the sequence may be selected. The skilled reader will appreciate that the nucleic acid molecules may also include sequences other than primer binding sites which are required for detection of the novel nucleic acid molecule produced by the modifying activity in the sample, for example RNA Polymerase binding sites or promoter sequences may be required for isothermal amplification technologies, such as NASBA, 3SR and TMA.

One or more primer binding sites may bridge the ligation/extension boundary of the substrate nucleic acid molecule such that an amplification product is only generated if ligation/extension has occurred, for example. Alternatively, primers may bind either side of the ligation/extension boundary and direct amplification across the boundary such that an amplification product is only generated (exponentially) if the ligated/extended nucleic acid molecule is formed. Primers and the substrate nucleic acid molecule(s) may be designed to avoid non-specific amplification (e.g. of genomic DNA in the sample).

Suitable primers for use in the methods of the invention are set forth in the experimental section below. They include primers comprising, consisting essentially of or consisting of SEQ ID NO: 4 and/or 5. These primers form a separate aspect of the invention. It is noted that variants of these sequences may be utilised in the present invention. In particular, additional sequence specific flanking sequences may be added, for example to improve binding specificity, as required. Variant sequences may have at least 90%, at least 91%, at least 92%, at least 93%, at least 94%, at least 95%, at least 96%, at least 97%, at least 98%, or at least 99% nucleotide sequence identity with the nucleotide sequences of the primers set forth in the experimental section. The primers may incorporate synthetic nucleotide analogues as appropriate or may be RNA or PNA based for example, or mixtures thereof. The primers may be labelled, such as with fluorescent labels and/or FRET pairs, depending upon the mode of detection employed. Probes may be utilised, again which may be labelled, as desired.

Thus, in certain aspects, the methods of the invention are carried out using nucleic acid amplification techniques in order to detect the modified nucleic acid molecule produced as a direct result of the action of nucleic acid-modifying activity on the substrate nucleic acid molecule which indicates the presence of a micro-organism in the sample. In certain embodiments the technique used is selected from PCR, NASBA, 3SR, TMA, SDA and DNA oligomer self-assembly.

Detection of the amplification products may be by routine methods, such as, for example, gel electrophoresis but in some embodiments is carried out using real-time or end-point detection methods.

A number of techniques for real-time or end-point detection of the products of an amplification reaction are known in the art. These include use of intercalating fluorescent dyes such as SYBR Green I (Sambrook and Russell, Molecular Cloning—A Laboratory Manual, Third edition), which allows the yield of amplified DNA to be estimated based upon the amount of fluorescence produced. Many of the real-time detection methods produce a fluorescent read-out that may be continuously monitored; specific examples including molecular beacons and fluorescent resonance energy transfer probes. Real-time and end-point techniques are advantageous because they keep the reaction in a "single tube". This means there is no need for downstream analysis in order to obtain results, leading to more rapidly obtained results. Furthermore keeping the reaction in a "single tube" environment reduces the risk of cross contamination and allows a quantitative output from the methods of the invention. This may be particularly important in the context of the present invention where health and safety concerns may be of paramount importance (such as in detecting potential microbial infection in a patient samples for example).

Real-time and end-point quantitation of PCR reactions may be accomplished using the TaqMan® system (Applied Biosystems), see Holland et al; Detection of specific polymerase chain reaction product by utilising the 5'-3' exonuclease activity of Thermus aquaticus DNA polymerase; Proc. Natl. Acad. Sci. USA 88, 7276-7280 (1991), Gelmini et al. Quantitative polymerase chain reaction-based homogeneous assay with flurogenic probes to measure C-Erb-2 oncogene amplification. Clin. Chem. 43, 752-758 (1997) and Livak et al. Towards fully automated genome wide polymorphism screening. Nat. Genet. 9, 341-342 (19995) (incorporated herein by reference). This type of probe may be generically referred to as a hydrolytic probe. Suitable hydrolytic/Taqman probes for use in real time or end point detection are also provided. The probe may be suitably labelled, for example using the labels detailed below.

In the Molecular Beacon system, see Tyagi & Kramer. Molecular beacons—probes that fluoresce upon hybridization. Nat. Biotechnol. 14, 303-308 (1996) and Tyagi et al. Multicolor molecular beacons for allele discrimination. Nat. Biotechnol. 16, 49-53 (1998) (incorporated herein by reference), the beacons are hairpin-shaped probes with an internally quenched fluorophore whose fluorescence is restored when bound to its target. These probes may be referred to as hairpin probes. Suitable probes useful in the present invention are set forth as SEQ ID NO: 1 and 2.

A further real-time fluorescence based system which may be incorporated in the methods of the invention is the Scorpion system, see Detection of PCR products using self-probing amplicons and fluorescence by Whitcombe et al. Nature Biotechnology 17, 804-807 (1 Aug. 1999). Additional real-time or end-point detection techniques which are well known to those skilled in the art and which are commercially available include Lightcycler® technology, Amplifluour® primer technology, DzyNA primers (Todd et al., Clinical Chemistry 46:5, 625-630 (2000)), or the Plexor™ qPCR and qRT-PCR Systems.

Thus, in further aspects of the invention the products of nucleic acid amplification are detected using real-time or end point techniques. In specific embodiments of the invention the real-time technique consists of using any one of hydrolytic probes (the Taqman® system), FRET probes (Lightcycler® system), hairpin primers (Amplifluour® system), hairpin probes (the Molecular beacons system), hairpin probes incorporated into a primer (the Scorpion® probe system), primers incorporating the complementary sequence of a DNAzyme and a cleavable fluorescent DNAzyme substrate (DzYNA), Plexor qPCR and oligonucleotide blocking systems.

Amplification products may be quantified to give an approximation of the microbial nucleic acid modifying activity in the sample and thus the level of microorganisms in the sample. Thus, "absence or presence" is intended to encompass quantification of the levels of microorganisms in the sample.

In certain embodiments, the reaction mixture will contain all of; the sample under test, the substrate nucleic acid molecule(s), reagents, buffers and enzymes required for amplification of the modified nucleic acid molecule optionally in addition to the reagents required to allow real time or end-point detection of amplification products. Thus the entire detection method for the nucleic acid modifying activity (from the one or more bacterial cells or microorganisms of interest) may occur in a single reaction, with a quantitative output, and without the need for any intermediate washing steps. Use of a "single tube" reaction is advantageous because there is no need for downstream analysis in order to obtain results, leading to more rapidly obtained results. Furthermore keeping the reaction in a "single tube" environment reduces the risk of cross contamination and allows a quantitative output from the methods of the invention. Also, single tube reactions are more amenable to automation, for example in a high throughput context.

Alternatively, the methods of the invention may be carried out in step-wise fashion. Thus, in a first step it may first be necessary to prepare the sample in a form suitable for use in the method of the invention. For example, as discussed herein, selective cell lysis or increasing cellular permeability may be required. Capture of specific nucleic acid modifying activity, such as polymerase or ligase, may also be desirable again as described herein. Other (sources of) nucleic acid modifying activity, such as nuclease activity, may be inhibited etc.

The steps of the methods of the invention prior to the amplification step may not comprise a step performed at a temperature of more than 40° C., more than 50° C., more than 60° C., more than 70° C., more than 80° C., more than 90° C. or more than 95° C.

Alternatively, the methods of the invention may not comprise any steps performed at a temperature of more than 40° C., more than 50° C., more than 60° C., more than 70° C., more than 80° C., more than 90° C. or more than 95° C.

The steps of the methods of the invention prior to the amplification step may be performed at a temperature between 10 and 50 degrees Celsius, between 15 and 45 degrees Celsius, between 20 and 40 degrees Celsius, between 25 and 40 degrees Celsius, between 30 and 40 degrees Celsius, between 25 and 35 degrees Celsius, or between 15 and 30 degrees Celsius, optionally the steps of the methods prior to the amplification step may be performed at room temperature.

Alternatively, steps of the methods of the invention may all be performed at a temperature between 10 and 50 degrees Celsius, between 15 and 45 degrees Celsius, between 20 and 40 degrees Celsius, between 25 and 40 degrees Celsius, between 30 and 40 degrees Celsius, between 25 and 35 degrees Celsius, or between 15 and 30 degrees Celsius, optionally all of the steps of the methods may be performed at room temperature.

The methods of the invention may comprise a step of inactivating nuclease activity in the sample. Alternatively, the methods of the invention do not comprise a step of inactivating nuclease activity in the sample. If performed, the step of inactivating nuclease activity takes place after the incubation step and before the step of specifically determining the absence or presence of a modified nucleic acid molecule (e.g. by amplification).

A "sample" in the context of the present invention is defined to include any sample in which it is desirable to test for the presence of a microorganism, such as a fungus (e.g. a yeast) or a bacterium, expressing nucleic acid modifying activity. Thus the sample may comprise, consist essentially of or consist of a clinical sample, such as a blood sample. The methods of the invention are particularly applicable to the rapid determination of negative blood cultures. Thus, the sample may comprise a blood culture sample from a patient suspected of suffering from, or being screened for, a bloodstream infection. The sample may be any suitable volume such as 1 to 10 ml, preferably a 1 ml blood culture sample.

Alternatively the sample may be or comprise an in vitro assay system for example. Samples may comprise, consist essentially of or consist of beverage or food samples or preparations thereof, or pharmaceutical or cosmetic products such as personal care products including shampoos, conditioners, moisturisers etc., all of which are tested for microbial contamination as a matter of routine. The sample may comprise, consist essentially of or consist of tissue or cells and may comprise, consist essentially of or consist of a sputum or a blood sample or a platelet sample for example. In addition, the methods and kits of the invention may be used to monitor contamination of surfaces, such as for example in locations where food is being prepared. Contamination is indicated by the presence of microbial nucleic acid modifying activity. The contamination may be from any microbial source, in particular bacterial or fungal (e.g yeast) contamination. Furthermore, the invention is also useful in monitoring environmental conditions such as water supplies, wastewater, marine environments etc. The invention is also useful in monitoring bacterial growth in fermentation procedures and in air sampling where bacteria or spore content can be assessed in hospital, industrial facilities or in biodefence applications.

The methods of the invention have various utilities in addition to screening samples for the absence or presence of a microorganism. Accordingly, in a further aspect the invention provides for use of a method as described herein for screening for resistance of a micro-organism to an agent directed against micro-organism. The method may involve steps of exposing the sample containing the microorganism of interest to the agent and then performing a method of the invention to determine whether the microorganism is resistant. If the microorganism is resistant, the modified nucleic acid molecule will be detected. Typically such methods are performed using well characterised samples, such as a cultured clinical isolate of a microorganism of interest.

Similarly, the invention provides for use of a method as described herein for screening candidate agents which may be capable of killing or preventing growth of one or more micro-organisms. This method may involve exposing the sample containing the microorganism to the agent and then performing a method of the invention. If the agent is an effective killing agent, there would be no (or reduced) modified nucleic acid detected. Typically such methods are performed using well characterised samples, such as a cultured clinical isolate of a microorganism of interest. The methods may be performed as a time course experiment to determine whether the agent is able to prevent growth of the microorganism (even if not able to kill). There may be a parallel reaction run in the absence of the agent to determine the growth of the microorganism in the absence of the agent. This provides a comparison for the effectiveness of the agent in terms of growth inhibition activity.

Further, the invention provides for use of the method as described herein for diagnosing an infection, or a disease associated with the presence of a micro-organism in a subject. In this context the "sample" will generally be a clinical sample. The sample being used will depend on the condition that is being tested for. Typical samples which may be used, but which are not intended to limit the invention, include whole blood, serum, plasma, platelet and urine samples etc. taken from a patient, most preferably a human patient. In a preferred embodiment, the test will be an in vitro test carried out on a sample removed from a subject. In a further embodiment, the above-described diagnostic methods may additionally include the step of obtaining the sample from a subject. Methods of obtaining a suitable sample from a subject are well known in the art. Alternatively, the method may be carried out beginning with a sample that has already been isolated from the patient in a separate procedure. The diagnostic methods will most preferably be carried out on a sample from a human, but the method of the invention may have diagnostic utility for many animals.

The diagnostic methods of the invention may be used to complement any already available diagnostic techniques, potentially as a method of confirming an initial diagnosis. Alternatively, the methods may be used as a preliminary diagnosis method in their own right, since the methods provide a quick and convenient means of diagnosis. Furthermore, due to their inherent sensitivity, the diagnostic methods of the invention require only a minimal sample, thus preventing unnecessary invasive surgery. Also, a large but non-concentrated sample may also be tested effectively according to the methods of the invention.

Thus, the methods of the invention have multiple applications beyond detection of contaminating organisms in a sample. The description provided above with respect to the various aspects of the invention applies mutatis mutandis to the other aspects of the invention and is not repeated for reasons of conciseness. For example, suitable controls may be incorporated for each method of the invention.

In specific embodiments the microorganism is a pathogenic microorganism, such as a pathogenic bacterium. The bacterium may be any bacterium which is capable of causing infection or disease in a subject, preferably a human subject. In one embodiment, the bacteria comprises or consists essentially of or consists of any one or more of *Staphylococcus* species, in particular *Staphylococcus aureus* and preferably methicillin resistant strains, *Enterococcus* species, *Streptococcus* species, *Mycobacterium* species, in particular *Mycobacterium tuberculosis*, *Vibrio* species, in particular *Vibrio cholerae*, *Salmonella* and/or *Escherichia coli* etc. The bacteria may comprise, consist essentially of or consist of *Clostridium* species and in particular *C. difficile* in certain embodiments. *C. difficile* is the major cause of antibiotic-associated diarrhoea and colitis, a healthcare associated intestinal infection that mostly affects elderly patients with other underlying diseases. *Candida* species such as *C. albicans, C. parapsilosis* and *C. glabrata* may be detected. *Cryptococcus* species such as *C. neoformans* may be detected. Fungaemia such as Candidaemia may be detected (presence or absence) using the invention.

In certain embodiments, according to these further aspects of the invention, the molecule which is being tested in the method (either for resistance or ability to treat an infection or toxicity to cells) is an antimicrobial compound. In the compound screening methods, any molecule may be tested. Examples include antimicrobial agents, nucleic acid molecules including siRNA (dsRNA) molecules and antisense molecules, small molecules, antibodies and all derivatives thereof including Fab fragments, variable region fragments and single domain antibodies for example provided they retain binding affinity etc. The method may be carried out in a high throughput context to screen large numbers of molecules in a short period of time.

The antimicrobial agent, in one embodiment, may be taken from the two main types of antimicrobial agents, antibiotics (natural substances produced by micro-organisms) and chemotherapeutic agents (chemically synthesized), or may be a hybrid of the two such as semi-synthetic antibiotics (a subsequently modified naturally produced antibiotic) or synthetic antibiotics (synthesised versions of natural antibiotics).

Suitable candidate antimicrobial agents may, following a positive result in the methods of the invention in terms of ability to kill or prevent growth of a bacterium or bacterial cell or other suitable micro-organism be tested for at least one or more of the following properties:

(1) the agent should be non-toxic to the subject and without adverse side effects,
(2) the agent should be non-allergenic to the subject,
(3) the agent should not eliminate the natural flora of the subject,
(4) the agent should be stable,
(5) the agent should preferably be cheap and readily available/easy to manufacture; and
(6) the agent should be sufficiently potent that pathogen resistance does not develop (to any appreciable degree). This feature may be tested according to the methods described above.

In one embodiment, a combination of multiple suitable antimicrobial agents may be tested for ability to treat an infection and/or for resistance thereto.

Antibiotics or derivatives thereof which may be tested for resistance and perhaps also for their novel ability to treat certain infections may be selected from the following groups, provided by way of example and not limitation; beta-lactams such as penicillin, in particular penicillin G or V, and cephalosporins such as cephalothin, semi-synthetic penicillins such as ampicillin, methicillin and amoxicillin, clavulanic acid preferably used in conjunction with a semi-synthetic penicillin preparation (such as clavamox or augmentin for example), monobactams such as aztreonam, carboxypenems such as imipenem, aminoglycosides such as streptomycin, kanamycin, tobramycin and gentamicin, glycopeptides such as vancomycin, lincomycin and clindamycin, macrolides such as erythromycin and oleandomycin, polypeptides such as polymyxin and bacitracin, polyenes such as amphotericin and nystatin, rifamycins such as rifampicin, tetracyclines such as tetracycline, semi-synthetic tetracyclines such as doxycycline, chlor tetracycline, chloramphenicol, quinolones such as nalidixic acid and fluoroquinolone and competitive inhibitors such as sulfonamides, for example gantrisin and trimethoprim. Ceftriaxone and/or nitroflurazone may also be utilised.

Still further the invention provides for use of a method as described herein for detecting the presence of microorganism contamination in a platelet containing sample. In such aspects, the methods may incorporate sub-steps of:

(i) lysis of the platelets under conditions that leave the microorganism cells intact. This principally allows selective concentration of microorganisms prior to testing for the presence of nucleic acid modifying activity. Thus, nucleic acid modifying activity provided by mammalian cells can be removed prior to testing
(ii) concentration of the microorganisms (for example by centrifugation to produce a bacterial cell containing pellet)
(iii) lysis of the microorganisms or a treatment to increase the permeability of the microorganisms to release the nucleic acid modifying activity.

The invention also relates to kits useful in performing the methods of the invention. Thus, there is provided a kit for carrying out a method as described herein comprising:

(a) at least one nucleic acid molecule which acts as a substrate for nucleic acid modifying activity of the micro-organism in the sample, wherein the at least one nucleic acid molecule is at least partially double stranded and comprises uracil residues in the complementary strand, characterised in that the nucleic acid molecule is modified so as to protect it from nuclease activity
(b) at least one internal positive control (IPC) nucleic acid molecule which comprises identical primer binding sites to the nucleic acid molecule such that there is competition for primer binding in a nucleic acid amplification reaction containing both the nucleic acid molecule and the IPC.

The kits may incorporate any of the components required to perform the methods of the invention. Accordingly, all discussion of the methods of the invention applies mutatis mutandis.

In the context of the present invention, the nucleic acid molecule is pre-modified so as to protect it from nuclease activity.

In some embodiments, the kit further comprises a nucleic acid probe which binds to a target probe sequence within the (sense strand of the) nucleic acid molecule. The kit may further comprise a further nucleic acid probe which binds to a target probe sequence within the IPC nucleic acid molecule. In certain embodiments, the nucleic acid probe does not bind to the IPC nucleic acid molecule and the further nucleic acid probe does not bind to the nucleic acid molecule. The nucleic acid probe and/or further nucleic acid probe may be labelled. In specific embodiments, the nucleic acid probe and further nucleic acid probe are differently labelled. For example, they may be labelled with fluorophores which have different wavelengths of maximal emission. Suitable pairs of labels can be readily selected by one skilled in the art, for example FAM and Texas Red may be used as different labels.

In further embodiments, the complementary strand of the nucleic acid molecule comprises a modification at the 3' end to prevent extension. By "extension" is meant the addition of further nucleotides. Any suitable modification may be employed. In specific embodiments, the modification is or comprises incorporation of a non-extendible nucleotide. Any suitable non-extendible nucleotide may be employed. For example, the non-extendible nucleotide may be or comprise a dideoxy nucleotide triphosphate (ddNTP), such as dideoxyCytidine.

In further embodiments, the IPC is modified so as to protect it from nuclease activity. In the context of the present invention, the IPC is pre-modified so as to protect it from nuclease activity. Suitable modifications are discussed in greater detail herein and may be selected from incorporation of methylation, protection of the 3' and/or 5' ends, incorporation of synthetic nucleotides. The synthetic nucleotides may be or comprise phosphorothioate nucleotides and/or locked nucleic acid nucleotides. Preferably, the synthetic nucleotides are phosphorothioate nucleotides. If both molecules are modified, it is preferable that they are modified in the same or similar manner such that the nuclease resistance is comparable. This permits the IPC to perform a most useful comparator role to determine the impact of nuclease activity on the substrate molecule.

In further embodiments, the kit further comprises a high pH reagent. The high pH reagent may be or comprise NaOH or Na2CO3. In specific embodiments, the concentration of the high pH reagent is around 5 mM or greater. The kit may further comprise a pH lowering agent. The pH lowering reagent may comprise a buffer or an acid, such as a Tris-HCl buffer (e.g. pH 7.2 or 8).

The kits may incorporate a suitable carrier in which the reactions take place. Advantageously, such a carrier may comprise a multi-well plate, such as a 48 or 96 well plate for example. Such a carrier allows the detection methods to be carried out in relatively small volumes—thus facilitating scale up and minimising the sample volume required.

The kits will typically incorporate suitable instructions. These instructions permit the methods of the invention to be carried out reliably using the kits of the invention.

The invention may be further defined in the following set of numbered clauses:

A method of detecting the absence or presence of a micro-organism in a sample comprising:
  (a) contacting the sample with a nucleic acid molecule which acts as a substrate for nucleic acid modifying activity of the micro-organism in the sample,
  (b) incubating the thus contacted sample under conditions suitable for nucleic acid modifying activity; and
  (c) specifically determining the absence or presence of a modified nucleic acid molecule resulting from the action of the nucleic acid modifying activity on the substrate nucleic acid molecule to indicate the absence or presence of the micro-organism, characterised in that the nucleic acid molecule is modified so as to protect it from nuclease activity.

2. The method of clause 1 wherein the modification is selected from incorporation of methylation, protection of the 3' and/or 5' ends and incorporation of synthetic nucleotides.

3. The method of clause 2 wherein the synthetic nucleotides comprise phosphorothioate nucleotides and/or locked nucleic acid nucleotides.

4. A method of detecting the absence or presence of a micro-organism in a sample comprising:
  (a) contacting the sample with a nucleic acid molecule which acts as a substrate for nucleic acid modifying activity of the micro-organism in the sample,
  (b) incubating the thus contacted sample under conditions suitable for nucleic acid modifying activity; and
  (c) specifically determining the absence or presence of a modified nucleic acid molecule resulting from the action of the nucleic acid modifying activity on the substrate nucleic acid molecule to indicate the absence or presence of the micro-organism, characterised in that the nucleic acid molecule is added to the sample at a concentration of at least 2 nM but less than 50 nM.

5. The method of clause 4 wherein step (a) and/or (b) comprises adding to the sample deoxyribonucleotide triphosphates at a concentration of at least 100 µM.

6. A method of detecting the absence or presence of a micro-organism in a sample, the sample containing a non-micro-organism source of nucleic acid modifying activity comprising:
  (a) treating the sample under high pH conditions for no more than 5 minutes in order to inhibit the non-micro-organism source of nucleic acid modifying activity (whilst not affecting the nucleic acid modifying activity of the micro-organism in the sample),
  (b) contacting the sample with a nucleic acid molecule which acts as a substrate for nucleic acid modifying activity of the micro-organism in the sample,
  (c) incubating the thus contacted sample under conditions suitable for nucleic acid modifying activity; and
  (d) specifically determining the absence or presence of a modified nucleic acid molecule resulting from the action of the nucleic acid modifying activity on the substrate nucleic acid molecule to indicate the absence or presence of the micro-organism.

7. The method of clause 6 wherein the high pH conditions comprise contacting the sample with NaOH or Na2CO3.

8. The method of clause 7 wherein the concentration of the NaOH or Na2CO3 is around 5 mM or greater.

9. The method of any one of clauses 6 to 8 wherein the treatment under high pH conditions is stopped by adding a reagent to lower the pH.

10. The method of clause 9 wherein the pH is lowered by adding a buffer or an acid.

11. The method of clause 10 wherein the buffer comprises a Tris-HCl buffer (e.g. pH 7.2 or 8).

12. The method of any one of clauses 6 to 11 wherein step (a) is performed at a temperature between 15 and 30 degrees Celsius.

13. The method of any one of clauses 6 to 12 wherein step (a) is performed at room temperature.

14. The method of any one of clauses 1 to 13 wherein the method is performed at a temperature between 15 and 30 degrees Celsius.

15. The method of any one of clauses 1 to 14 wherein the method is performed at room temperature.

16. A method of detecting the absence or presence of a micro-organism in a sample, the sample containing a non-micro-organism source of nucleic acid modifying activity comprising:
  (a)
    (i) incubation of the sample with a reagent that lyses non-microorganisms if present in the sample but does not lyse microorganisms in the sample
    (ii) optionally separation of the lysed cell material from the intact microorganisms (if any) in the sample
    (iii) contacting the (separated) intact microorganisms (if any) in the sample with a high pH reagent and incubating for no more than 5 minutes in order to inhibit the non-micro-organism source of nucleic acid modifying activity (whilst not affecting the nucleic acid modifying activity of the micro-organism in the sample)
    (iv) adding a pH lowering reagent in order to stop the incubation at high pH
    (v) separation of the microorganisms if present in the sample from the pH modifying reagents
    (vi) lysis of any separated microorganisms
    (vi) contacting the sample with a nucleic acid molecule which acts as a substrate for nucleic acid modifying activity of the micro-organism in the sample,
    (vii) incubating the thus contacted sample under conditions suitable for nucleic acid modifying activity; and
    (viii) specifically determining the absence or presence of a modified nucleic acid molecule resulting from the action of the nucleic acid modifying activity on the substrate nucleic acid molecule to indicate the absence or presence of the micro-organism.
  or
  (b)
    (i) incubation of the sample with a reagent that lyses non-microorganisms if present in the sample but does not lyse micro-organisms in the sample
    (ii) centrifugation of the sample to form a pellet containing micro-organisms if present in the sample
    (iii) removal of the supernatant from the pellet
    (iv) re-suspending the pellet in a high pH reagent and incubating for no more than 8 minutes in order to inhibit the non-micro-organism source of nucleic acid modifying activity (whilst not affecting the nucleic acid modifying activity of the micro-organism in the sample)
    (v) adding a pH lowering reagent in order to stop the incubation at high pH (vi) a second centrifugation of the sample to form a pellet containing micro-organisms if present in the sample
(vi) removal of the supernatant from the pellet
(vii) lysing any micro-organisms in the pellet
(viii) contacting the sample with a nucleic acid molecule which acts as a substrate for nucleic acid modifying activity of the micro-organism in the sample,
(ix) incubating the thus contacted sample under conditions suitable for nucleic acid modifying activity; and
(x) specifically determining the absence or presence of a modified nucleic acid molecule resulting from the action of the nucleic acid modifying activity on the substrate nucleic acid molecule to indicate the absence or presence of the micro-organism.

17. The method of clause 16 wherein the high pH reagent comprises NaOH or Na2CO3.

18. The method of clause 16 or 17 wherein the concentration of the high pH reagent is around 5 mM or greater.

19. The method of any one of clauses 16 to 18 wherein the pH lowering reagent comprises a buffer or an acid.

20. The method of clause 19 wherein the buffer comprises a Tris-HCl buffer (pH 7.2 or 8)

21. The method of any one of clauses 16 to 20 wherein step (a)(iii) or (b)(iv) is performed at a temperature between 15 and 30 degrees Celsius.

22. The method of any one of clauses 16 to 21 wherein step (a)(iii) or (b)(iv) is performed at room temperature.

23. The method of any one of clauses 16 to 22 wherein the method is performed at a temperature between 15 and 30 degrees Celsius.

24. The method of any one of clauses 16 to 23 wherein the method is performed at room temperature.

25. A method of detecting the absence or presence of a micro-organism in a (liquid) sample, the sample potentially containing a non-micro-organism source of nuclease activity comprising:
   (i) incubation of the sample with a reagent that lyses non-micro-organisms if present in the sample but does not lyse micro-organisms in the sample
   (ii) separation of the lysed cell material from the intact microorganisms (if any) in the sample and/or inactivation of the lysed cell material
   (iii) lysing any microorganisms following the separation and/or inactivation
   (iv) contacting the sample with a nucleic acid molecule which acts as a substrate for nucleic acid modifying activity of the micro-organism in the sample together with an internal positive control (IPC) nucleic acid molecule,
   (v) incubating the thus contacted sample under conditions suitable for nucleic acid modifying activity; and
   (vi) specifically determining the absence or presence of a modified nucleic acid molecule resulting from the action of the nucleic acid modifying activity on the substrate nucleic acid molecule to indicate the absence or presence of the micro-organism, characterised in that the IPC nucleic acid molecule is modified so as to protect it from nuclease activity
or
   (a) centrifugation of the sample to form a pellet containing micro-organisms if present in the sample
   (b) removal of the supernatant from the pellet
   (c) lysing any micro-organisms in the pellet
   (d) contacting the sample with a nucleic acid molecule which acts as a substrate for nucleic acid modifying activity of the micro-organism in the sample together with an internal positive control (IPC) nucleic acid molecule,
   (e) incubating the thus contacted sample under conditions suitable for nucleic acid modifying activity; and
   (f) specifically determining the absence or presence of a modified nucleic acid molecule resulting from the action of the nucleic acid modifying activity on the substrate nucleic acid molecule to indicate the absence or presence of the micro-organism, characterised in that the IPC nucleic acid molecule is modified so as to protect is from nuclease activity.

26. The method of clause 25 wherein the nucleic acid molecule is modified so as to protect it from nuclease activity.

27. The method of clause 25 or 26 wherein the modification is selected from incorporation of methylation, protection of the 3' and/or 5' ends, incorporation of synthetic nucleotides.

28. The method of clause 27 wherein the synthetic nucleotides comprise phosphorothioate nucleotides and/or locked nucleic acid nucleotides.

29. A method of detecting the absence or presence of a micro-organism in a (liquid) sample, the sample potentially containing a non-micro-organism source of nuclease activity comprising:
   (i) incubation of the sample with a reagent that lyses non-micro-organisms if present in the sample but does not lyse micro-organisms in the sample
   (ii) separation of the lysed cell material from the intact microorganisms (if any) in the sample and/or inactivation of the lysed cell material
   (iii) lysing any microorganisms following the separation and/or inactivation
   (iv) contacting the sample with a nucleic acid molecule which acts as a substrate for nucleic acid modifying activity of the micro-organism in the sample together with an internal positive control (IPC) nucleic acid molecule,
   (v) incubating the thus contacted sample under conditions suitable for nucleic acid modifying activity; and
   (vi) specifically determining the absence or presence of a modified nucleic acid molecule resulting from the action of the nucleic acid modifying activity on the substrate nucleic acid molecule to indicate the absence or presence of the micro-organism, characterised in that the IPC nucleic acid molecule is susceptible to nuclease activity and is used to identify contaminating nuclease activity in the pellet.
or
   (a) centrifugation of the sample to form a pellet containing micro-organisms if present in the sample
   (b) removal of the supernatant from the pellet
   (c) lysing any micro-organisms in the pellet
   (d) contacting the sample with a nucleic acid molecule which acts as a substrate for nucleic acid modifying activity of the micro-organism in the sample together with an internal positive control (IPC) nucleic acid molecule,
   (e) incubating the thus contacted sample under conditions suitable for nucleic acid modifying activity; and
   (f) specifically determining the absence or presence of a modified nucleic acid molecule resulting from the action of the nucleic acid modifying activity on the substrate nucleic acid molecule to indicate the absence or presence of the micro-organism, characterised in that the IPC nucleic acid molecule is susceptible to nuclease activity and is used to identify contaminating nuclease activity in the pellet.

30. The method of any one of clauses 25 to 29 wherein steps (iii) and (iv) or (c) and (d) respectively are performed together.

31. The method of clause 30 wherein the nucleic acid molecule is added to the sample together with a lysis reagent.

32. The method of any one of clauses 1 to 31 wherein specifically determining the absence or presence of the modified nucleic acid molecule comprises a nucleic acid amplification step.

33. The method of clause 32 wherein the nucleic acid molecule is at least partially double stranded and comprises uracil residues in the complementary strand and the step of specifically determining the absence or presence of the modified nucleic acid molecule comprises adding Uracil DNA Glycosylase (UDG) to the sample in order to degrade the uracil residues in the complementary strand.

34. The method of any one of clauses 25 to 33 wherein the IPC nucleic acid molecule comprises identical primer binding sites to the nucleic acid molecule such that there is competition for primer binding in step (f).

35. The method of any one of clauses 25 to 34 wherein a nucleic acid probe is added in step (f) which binds to a target probe sequence within the (sense strand of the) nucleic acid molecule.

36. The method of any one of clauses 25 to 35 wherein a further nucleic acid probe is added in step (f) which binds to a target probe sequence within the IPC nucleic acid molecule.

37. The method of clause 36 wherein the nucleic acid probe does not bind to the IPC nucleic acid molecule and the further nucleic acid probe does not bind to the nucleic acid molecule.

38. The method of any one of clauses 35 to 37 wherein the nucleic acid probe is labelled.

39. The method of any one of clauses 35 to 38 wherein the further nucleic acid probe is labelled.

40. The method of clause 38 or 39 wherein the nucleic acid probe and further nucleic acid probe are differently labelled 41. The method of clause 33 wherein the complementary strand of the nucleic acid molecule comprises a modification at the 3' end to prevent extension.

42. The method of clause 41 wherein the modification comprises incorporation of a non-extendible nucleotide 43. The method of clause 42 wherein the non-extendible nucleotide is a dideoxy nucleotide triphosphate (ddNTP).

44. The method of clause 43 wherein the ddNTP is dideoxyCytidine.

45. The method of any one of clauses 29 to 44 wherein the nucleic acid molecule is modified so as to protect it from nuclease activity.

46. The method of clause 45 wherein the modification is selected from incorporation of methylation, protection of the 3' and/or 5' ends, incorporation of synthetic nucleotides.

47. The method of clause 46 wherein the synthetic nucleotides comprise phosphorothioate nucleotides and/or locked nucleic acid nucleotides.

48. A method of detecting the absence or presence of a microorganism in a sample, the sample containing a non-microorganism source of nucleic acid modifying activity comprising:

(i) incubation of the sample with a reagent that lyses non-microorganisms if present in the sample but does not lyse microorganisms in the sample
(ii) optionally separation of the lysed cell material from the intact microorganisms (if any) in the sample
(iii) contacting the (separated) intact microorganisms (if any) in the sample with a high pH reagent and incubating for no more than 5 minutes in order to inhibit the non-micro-organism source of nucleic acid modifying activity (whilst not affecting the nucleic acid modifying activity of the micro-organism in the sample)
(iv) adding a pH lowering reagent in order to stop the incubation at high pH
(v) separation of the microorganisms if present in the sample from the pH modifying reagents
(vi) lysis of any separated microorganisms
(vii) contacting the sample with a nucleic acid molecule which acts as a substrate for nucleic acid modifying activity of the micro-organism in the sample,
(viii) incubating the thus contacted sample under conditions suitable for nucleic acid modifying activity; and
(ix) specifically determining the absence or presence of a modified nucleic acid molecule resulting from the action of the nucleic acid modifying activity on the substrate nucleic acid molecule to indicate the absence or presence of the micro-organism, wherein the nucleic acid molecule is modified so as to protect it from nuclease activity.

or (a) incubation of the sample with a reagent that lyses non-micro-organisms if present in the sample but does not lyse micro-organisms in the sample
(b) centrifugation of the sample to form a pellet containing micro-organisms if present in the sample
(c) removal of the supernatant from the pellet
(d) re-suspending the pellet in a high pH reagent and incubating for no more than 8 minutes in order to inhibit the non-micro-organism source of nucleic acid modifying activity (whilst not affecting the nucleic acid modifying activity of the micro-organism in the sample)
(e) adding a pH lowering reagent in order to stop the incubation at high pH
(f) a second centrifugation of the sample to form a pellet containing micro-organisms if present in the sample
(g) removal of the supernatant from the pellet
(h) lysing any micro-organisms in the pellet
(i) contacting the sample with a nucleic acid molecule which acts as a substrate for nucleic acid modifying activity of the micro-organism in the sample,
(j) incubating the thus contacted sample under conditions suitable for nucleic acid modifying activity; and
(k) specifically determining the absence or presence of a modified nucleic acid molecule resulting from the action of the nucleic acid modifying activity on the substrate nucleic acid molecule to indicate the absence or presence of the micro-organism, wherein the nucleic acid molecule is modified so as to protect it from nuclease activity.

49. The method of clause 48 wherein the modification is selected from incorporation of methylation, protection of the 3' and/or 5' ends, incorporation of synthetic nucleotides.

50. The method of clause 49 wherein the synthetic nucleotides comprise phosphorothioate nucleotides and/or locked nucleic acid nucleotides.

51. The method of any one of clauses 48 to 50 further characterised in that the nucleic acid molecule is added to the sample at a concentration of at least 2 nM and less than 50 nM.

52. The method of any one of clauses 48 to 51 wherein step (vii) or (i) respectively comprises adding to the sample deoxyribonucleotide triphosphates at a concentration of at least 100 µM.

53. The method of any one of clauses 48 to 52 wherein the high pH reagent comprises NaOH or Na2CO3.

54. The method of any one of clauses 48 to 53 wherein the concentration of the high pH reagent is around 5 mM or greater.

55. The method of any one of clauses 48 to 54 wherein the pH lowering reagent comprises a buffer or an acid.

56. The method of clause 55 wherein the buffer comprises a Tris-HCl buffer (pH 7.2 or 8)

57. The method of any one of clauses 48 to 56 wherein step (iv) or (d) respectively is performed at a temperature between 15 and 30 degrees celcius.

58. The method of any one of clauses 48 to 57 wherein step (iv) or (d) respectively is performed at room temperature.

59. The method of any one of clauses 48 to 58 wherein the method is performed at a temperature between 15 and 30 degrees celcius.

60. The method of any one of clauses 48 to 59 wherein the method is performed at room temperature.

61. The method of any one of clauses 48 to 60 wherein step (vi) or (i) respectively comprises contacting the sample with a nucleic acid molecule which acts as a substrate for nucleic acid modifying activity of the micro-organism in the sample together with an internal positive control (IPC) nucleic acid molecule, wherein the IPC nucleic acid molecule is susceptible to nuclease activity and is used to identify contaminating nuclease activity in the pellet.

62. The method of any one of clauses 48 to 60 wherein step (vi) or (i) respectively comprises contacting the sample with a nucleic acid molecule which acts as a substrate for nucleic acid modifying activity of the micro-organism in the sample together with an internal positive control (IPC) nucleic acid molecule, wherein the IPC nucleic acid molecule is modified so as to protect it from nuclease activity.

63. The method of clause 62 wherein the modification is selected from incorporation of methylation, protection of the 3' and/or 5' ends, incorporation of synthetic nucleotides.

64. The method of clause 63 wherein the synthetic nucleotides comprise phosphorothioate nucleotides and/or locked nucleic acid nucleotides.

65. The method of any one of clauses 48 to 64 wherein steps (vi) and (vii) or (h) and (i) respectively are performed together 66. The method of clause 65 wherein the nucleic acid molecule is added to the sample together with a lysis reagent.

67. The method of any one of clauses 48 to 66 wherein step (xi) or (k) respectively comprises a nucleic acid amplification step.

68. The method of any one of clauses 48 to 67 wherein the nucleic acid molecule is at least partially double stranded and comprises uracil residues in the complementary strand and step (k) comprises adding Uracil DNA Glycosylase (UDG) to the sample in order to degrade the uracil residues in the complementary strand.

69. The method of any one of clauses 64 to 68 wherein the IPC nucleic acid molecule comprises identical primer binding sites to the nucleic acid molecule such that there is competition for primer binding in step (xi) or (k) respectively.

70. The method of any one of clauses 48 to 69 wherein a nucleic acid probe is added in step (xi) or (k) respectively which binds to a target probe sequence within the (sense strand of the) nucleic acid molecule.

71. The method of clause 70 wherein a further nucleic acid probe is added in step (xi) or (k) respectively which binds to a target probe sequence within the IPC nucleic acid molecule.

72. The method of clause 71 wherein the nucleic acid probe does not bind to the IPC nucleic acid molecule and the further nucleic acid probe does not bind to the nucleic acid molecule.

73. The method of any one of clauses 70 to 72 wherein the nucleic acid probe is labelled.

74. The method of any one of clauses 71 to 73 wherein the further nucleic acid probe is labelled.

75. The method of clause 74 wherein the nucleic acid probe and further nucleic acid probe are differently labelled.

76. The method of any one of clauses 68 to 75 wherein the complementary strand of the nucleic acid molecule comprises a modification at the 3' end to prevent extension.

77. The method of clause 76 wherein the modification comprises incorporation of a non-extendible nucleotide.

78. The method of clause 77 wherein the non-extendible nucleotide is a dideoxy nucleotide triphosphate (ddNTP).

79. The method of clause 78 wherein the ddNTP is dideoxyCytidine.

80. The method of any one of clauses 1 to 79 wherein the nucleic acid modifying activity comprises polymerase activity.

81. Use of the method according to any one of clauses 1 to 80 for screening for resistance of a micro-organism to an agent directed against micro-organism.

82. Use of the method according to any one of clauses 1 to 80 for screening candidate agents which may be capable of killing or preventing growth of one or more micro-organisms.

83. Use of the method according to any one of clauses 1 to 80 for diagnosing an infection, or a disease associated with the presence of a micro-organism in a subject.

84. Use of the method according to any one of clauses 1 to 80 for detecting the presence of micro-organism contamination in a platelet containing sample.

85. A kit for carrying a method according to any one of clauses 1 to 84 comprising:
  (a) at least one nucleic acid molecule which acts as a substrate for nucleic acid modifying activity of the micro-organism in the sample, wherein the at least one nucleic acid molecule is at least partially double stranded and comprises uracil residues in the complementary strand, characterised in that the nucleic acid molecule is modified so as to protect it from nuclease activity
  (b) at least one internal positive control (IPC) nucleic acid molecule which comprises identical primer binding sites to the nucleic acid molecule such that there is competition for primer binding in a nucleic acid amplification reaction containing both the nucleic acid molecule and the IPC.

86. The kit of clause 85 wherein the kit further comprises a nucleic acid probe which binds to a target probe sequence within the (sense strand of the) nucleic acid molecule.

87. The kit of clause 85 or 86 wherein the kit further comprises a further nucleic acid probe which binds to a target probe sequence within the IPC nucleic acid molecule.

88. The kit of clause 86 or 87 wherein the nucleic acid probe does not bind to the IPC nucleic acid molecule and the further nucleic acid probe does not bind to the nucleic acid molecule.

89. The kit of any one of clauses 86 to 88 wherein the nucleic acid probe is labelled.

90. The kit of any one of clauses 87 to 89 wherein the further nucleic acid probe is labelled.

91. The kit of any one of clauses 87 to 90 wherein the nucleic acid probe and further nucleic acid probe are differently labelled.

92. The kit of any one of clauses 85 to 91 wherein the complementary strand of the nucleic acid molecule comprises a modification at the 3' end to prevent extension.

93. The kit of clause 92 wherein the modification comprises incorporation of a non-extendible nucleotide.

94. The kit of clause 93 wherein the non-extendible nucleotide is a dideoxy nucleotide triphosphate (ddNTP).

95. The kit of clause 94 wherein the ddNTP is dideoxy-Cytidine.

96. The kit of any one of clauses 85 to 95 wherein the IPC is modified so as to protect it from nuclease activity.

97. The kit of clause 96 wherein the modification is selected from incorporation of methylation, protection of the 3' and/or 5' ends, incorporation of synthetic nucleotides.

98. The kit of clause 97 wherein the synthetic nucleotides comprise phosphorothioate nucleotides and/or locked nucleic acid nucleotides.

99. The kit of any one of clauses 85 to 98 wherein the kit further comprises a high pH reagent.

100. The kit of clause 99 wherein the high pH reagent comprises NaOH or Na2CO3.

101. The kit of clause 99 or 100 wherein the concentration of the high pH reagent is around 5 mM or greater.

102. The kit of any one of clauses 85 to 101 further comprising a pH lowering agent.

103. The kit of clause 102 wherein the pH lowering reagent comprises a buffer or an acid.

104. The kit of clause 103 wherein the buffer comprises a Tris-HCl buffer (pH 7.2 or 8).

DESCRIPTION OF THE FIGURES

FIG. 4. ETGA test background reduction and improved test sensitivity. Graphs show fluorescence detected in the FAM channel in qPCR reaction from ETGA tests carried out on a dilution series of *C. albicans* in blood culture. The qPCR reaction contained a FAM-labelled probe, capable of detecting the modified ETGA substrate, so amplification indicates the presence of a microorganism.

Figure 1A:
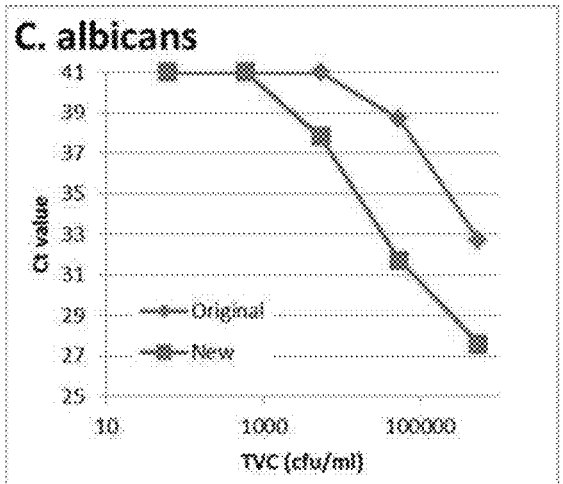
FIG. 1. Improved ETGA detection of microorganisms by increasing dNTP and substrate concentration. Each chart shows the ct value obtained for the detection of the ETGA target substrate (FAM channel) in ETGA detection experiments for a range of relevant microorganisms. In all cases the negative blood culture control was >39.9 ct units, the negative reagent negative controls were >40 ct units and the positive reagent controls were <20 ct units.
Figure 1B:
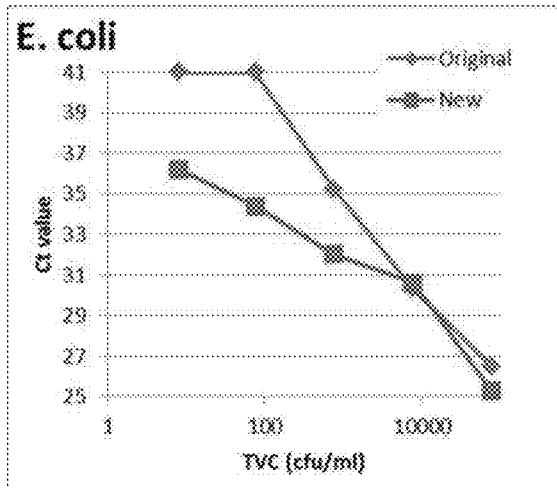
Figure 1C:
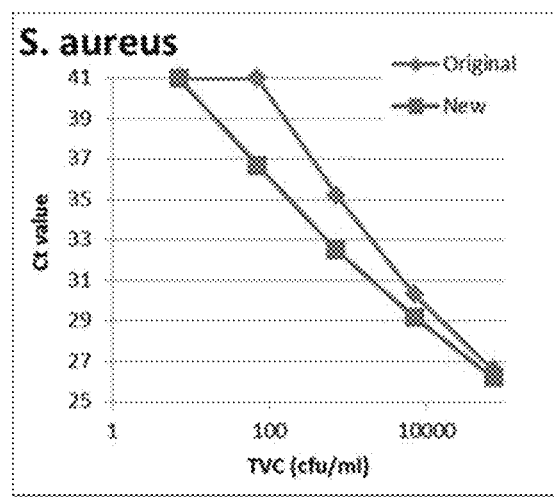
Figure 1D:
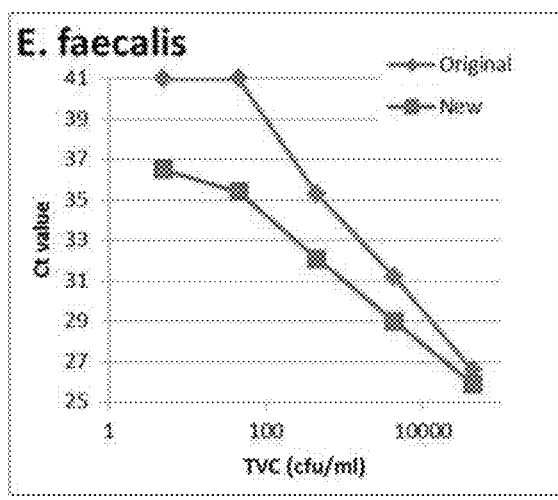
Figure 1E:
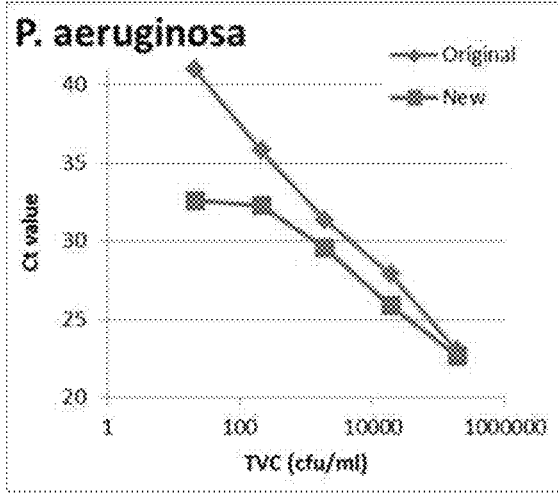

FIGS. 12A-E. Cognitor Minus results for (A) *E. coli*, (B) *S. aureus* and (C) *C. albicans* spiked blood broth samples, (D) positive controls (PC) and (E) no spike controls (NSCs). Ct values from three replicate experiments (n=3) are plotted against sample storage duration. Trend lines are plotted for each sample set: PTO 95° C. (+); PTO 95° C. (−); UMO 95° C. (+); and UMO 95° C. (−). Only UMO LM data are shown for NSC samples because most PTO LM samples produced 'No Ct' due to insufficient amplification.

EXPERIMENTAL SECTION

The invention will be understood with respect to the following non-limiting examples:

Example 1—ETGA Test Modifications

Methods—General Protocol

For each sample, 1 mL of blood culture (with or without microorganisms added, with or without blood) was mixed with 0.333 mL Reagent A (5% w/v Saponin, 5% w/v Tween 20, 8.5 g/L sodium chloride) in a 1.5 mL microcentrifuge tube and incubated at room temperature for 15 min. Each sample was centrifuged for 3 min at 7300 g, then the supernatant was poured away and the rim of the tube was dabbed on clean laboratory tissue paper. Each pellet was then resuspended in 0.75 mL of Reagent B (5 mM NaOH) and incubated for 5 min, then pH was lowered by adding 0.5 mL of Reagent C (1.32 g/L ammonium sulphate, 0.49 g/L magnesium sulphate heptahydrate, 0.75 g/L potassium chloride, 20 mM Tris-HCl, pH8.0). After incubation, samples were centrifuged again and the supernatant removed by pouring away. The remaining pellet was resuspended in 0.5 mL of Reagent C and immediately transferred to a new tube containing a mixture of glass beads (0.1 mm and 0.5 mm glass beads; supplied by CamBio cat 13118-400, and 13116-400 respectively). A further centrifugation was carried out in order to pellet any suspended cells with the glass beads, and again, the supernatant was removed and discarded.

50 μL of microbial Lysis Mixture containing the ETGA substrate (LM; containing reagents L1, L2, L3 at a ratio of 7:2:1, see Table 1) was added to the glass beads and placed in a Disruptor Genie (Scientific Industries, Inc.) cell disruptor for 6 min at 2800 rpm to lyse microbial cells. After disruption, samples were placed in a 37° C. heating block and incubated for 20 min, then transferred to another heating block at 95° C. and incubated for 5 min. After incubation, samples were cooled to room temperature whilst the PCR reagents were prepared.

After cooling, 3 μL of sample supernatant was added to 27 μL of PCR mastermix (MM; containing a general Taq polymerase PCR mastermix (Roche—cat 04902343001), primers for the ETGA substrate, internal positive control—IPC—DNA, FAM-labelled probe for the ETGA substrate, Texas Red labelled probe for the IPC, and (1.2 ul) UDG enzyme (Bioline—cat no BIO-27044)) in a SmartCycler PCR tube (Cepheid). Samples were placed in the SmartCycler PCR and subjected to the following reaction conditions;
1 cycle; 40° C. 10 min, 50° C. 10 min, 95° C. 5 min
40-50 cycles: 95° C. 5 sec, 61° C. 20 sec, 72° C. 20 sec.
Amplification was monitored throughout the reaction in real-time in the Texas Red and FAM excitation/detection channels of the SmartCycler.

TABLE 1

| Lysis mixture components | | |
|---|---|---|
| L1 | Bovine serum albumin | 1.5% w/v |
|  | Triton X100 | 1.5% v/v |
|  | Tween 20 | 1.5% v/v |
| L2 | Ammonium sulphate | 2.64 g/L |
|  | Magnesium sulphate heptahydrate | 0.98 g/L |
|  | Potassium chloride | 1.5 g/L |
|  | Tris-HCl, pH 8.0 | 40 mM |
|  | dNTP (A,G,C,T) | 500 μM |
| L3 | ETGA substrate | 0.001 μM-0.01 μM |
|  | Tris-HCl, pH 8.5 | 20 mM |
|  | KCl | 10 mM |
|  | EDTA | 10 μM |

The sequences of the PCR reaction components are as follows;

Fam labelled probe (a molecular beacon):
(SEQ ID NO: 1)
FAM-cgc tgc gac cga ccg ata agc tag aac agg cag cg-BHQ1

Texas red labelled probe (a molecular beacon):
(SEQ ID NO: 2)
TxR-cgc gat cag cag gcc aca cgt taa aga cat cgc g-BHQ2

IPC
(SEQ ID NO: 3)
gcc gat atc gga caa cgg ccg aac tgg gaa ggc gag atc agc agg cca cac gtt aaa gac aga gag aca aca acg ctg gcc gtt tgt cac cga cgc cta Forward primer
(SEQ ID NO: 4)
ccg ata tcg gac aac ggc cga act gg Reverse primer
(SEQ ID NO: 5)
tag gcg tcg gtg aca aac ggc cag c The substrate components are;

AS
(SEQ ID NO: 6)
uaggcgucggugacaaacggccagcguuguugucucu-DDC (3' terminal is a dideoxy-C)

S1
(SEQ ID NO: 7)
gccgatatcggacaacggccgaactgggaaggcgagactgaccgaccgat aagctagaacagagagacaacaac Results and Discussion 1—Increasing Substrate Concentration The general protocol was modified by increasing the amount of ETGA substrate in LM by 10-fold (from 0.001 μM to 0.01 μM) and increasing the amount of dNTP 2-fold (from 50 μM to 100 μM).

Figure 1F:
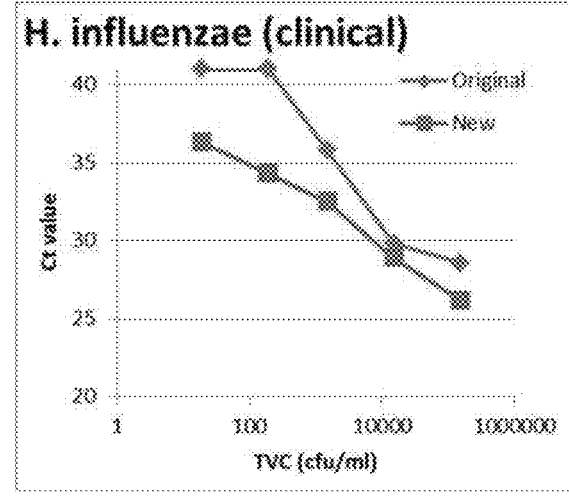
Figure 1G:
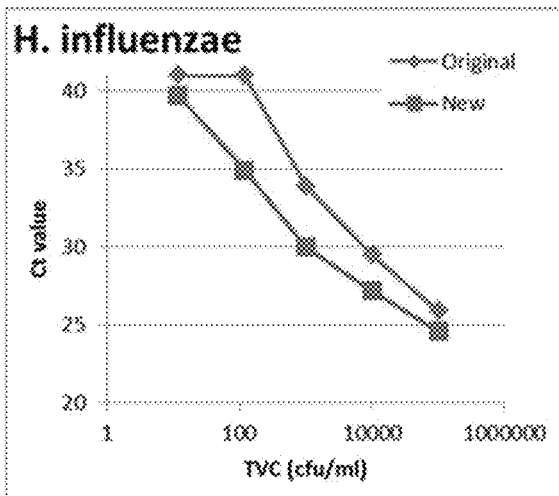

The increased quantity of substrate and dNTP enabled improved detection of *C. albicans* (FIG. 1a), *E. coli* (FIG. 1b), *S. aureus* (FIG. 1c), *E. faecalis* (FIG. 1d), *P. aeruginosa* (FIG. 1e), or 2 different strains of *H. influenzae* (including a delicate clinical strain) (FIG. 1f and FIG. 1g). Data is shown in FIG. 1.

Results and Discussion 2—Improving ETGA Test Sensitivity and Lowering Background by Modifying Oligo Components Evidence of Nuclease Activity Adding the IPC molecule at the same time as the ETGA substrate molecule was thought to be an improvement on the original protocol. If IPC was added in LM, the IPC would be subject to exactly the same test conditions as the ETGA substrate and therefore provide a more accurate test control. For example, conditions that may negatively impact the substrate molecule such as nuclease activity that could digest the substrate, would also affect the IPC. If the IPC is added later (in MM for example) it would not be subject to the same conditions and may result in false interpretation of the data. If IPC is added at the same time as the ETGA substrate the magnitude of the effect of the test conditions on the nucleic acid templates could be measured.

Figure 2:
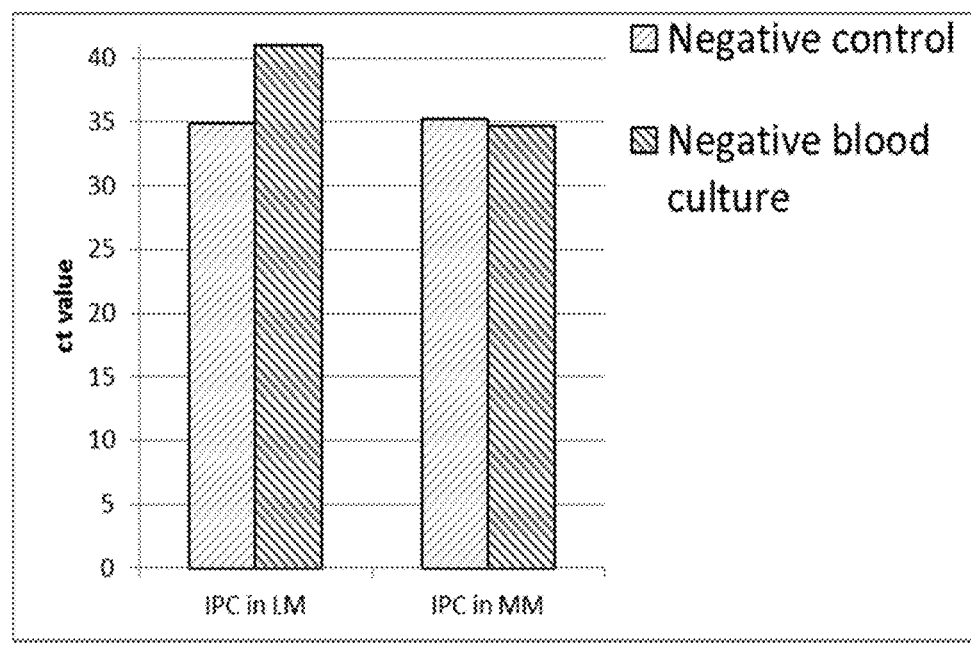
FIG. 2. Detection of IPC molecule in a blood culture sample prepared with IPC DNA added only in the microbial Lysis mixture (LM) or PCR mastermix (MM) compared to a negative control sample. A quantity of IPC DNA was added to the LM to provide the same ct value as when added to the MM. Data shows that there is a complete loss in detection of the IPC molecule (in a 40 cycle PCR reaction) in the negative blood culture sample compared to the negative control (with no blood) when added to LM and not when added to MM.

To exemplify this, FIG. 2 shows that test conditions could have a negative impact on the detection of the ETGA substrate; when adding comparable amounts of IPC DNA in LM rather than in MM, it was found that there was indeed a loss in the ability to detect the IPC in blood culture specimens compared to negative control samples (without blood). The same loss of detection was not seen when using IPC in MM. Loss of the IPC when added in LM was attributed to nucleases that may have been active during the 37° C. incubation step of the ETGA protocol. Nucleases were most likely to have originated from the blood specimen.

Clearly, if the IPC molecule was lost during the test, the ETGA substrate molecule could also be lost.

Loss of the ETGA substrate molecule in a positive blood culture sample would obviously result in reduced detection sensitivity or potentially lead to a false negative result, but, by adding IPC to LM it would be possible to determine (and perhaps quantify) suspected nuclease activity and interpret results accordingly. Samples where a drop in IPC quantity was observed (as seen by a rise in ct value compared to a negative reagent control) could be reported as 'unresolved' rather than 'negative', thus indicating that the sample was subject to nuclease activity and may, in fact, be positive.

Adding an IPC molecule to LM could improve the ETGA test. However, depending on how common nuclease activity was found to be in clinical specimens, this could raise the overall number of unresolved results rendering the test less attractive to potential users due to the high perceived failure rate (and thus explaining why IPC was originally added to MM rather than LM).

Figure 3:
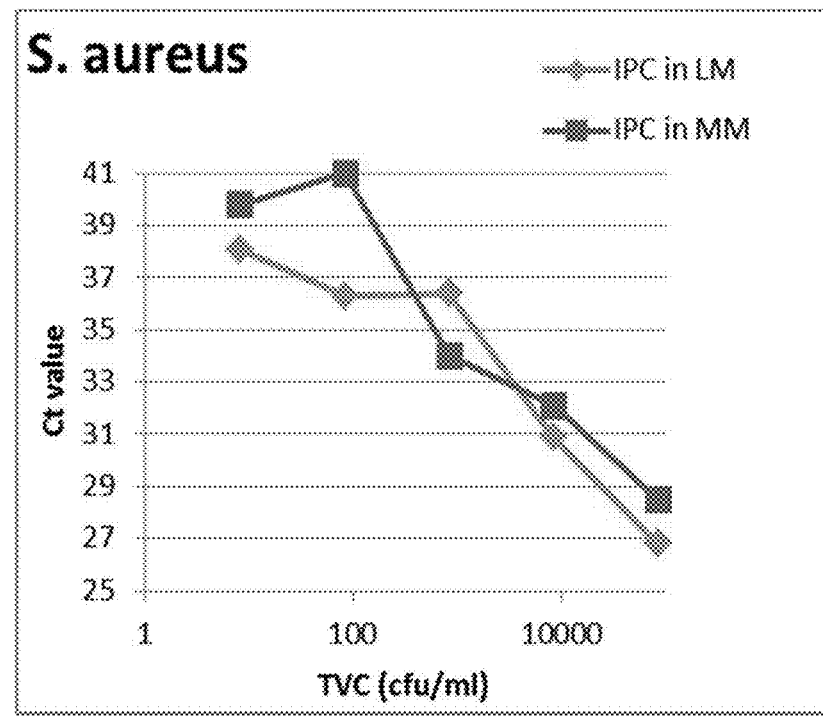
FIG. 3. Increased background caused by adding IPC to LM instead of MM. The data plotted on the chart shows ct value in the FAM channel (detecting ETGA substrate) versus total viable count (TVC) obtained for blood culture samples using a protocol where the IPC had been added to LM (diamonds) and MM (squares). The amount of IPC added to LM was equivalent to 50× higher than in MM for each PCR reaction. The measured background was higher when using 50× the normal concentration of IPC in LM compared to using the standard concentration of IPC in MM. Background levels were measured by an ETGA test procedure with IPC in the MM (blue dashed line) or LM (green dot-dashed line) in blood culture samples that did not contain any added bacteria.

Testing showed that the IPC molecule could be added to the test in the LM and still be detected in the presence of presumed nuclease activity by increasing the concentration 20-50 fold, but high levels of background were detected even in negative blood culture samples (FIG. 3). In this case, background may have been caused by the presence of partly digested oligonucleotides that interfere in the detection PCR reaction. Obviously, high levels of background may reduce the sensitivity of the test, especially when attempting to detect very low numbers of bacteria.

Whilst increasing the amount of IPC in LM may be considered a solution to the problem of loss of target DNA molecules due to nuclease activity, it may only mask the issue and as previously mentioned may contribute to higher background level. Increasing the amount of IPC molecule in samples where contaminating nuclease activity was low could also reduce test sensitivity by increasing competition for reaction components in the detection PCR thereby reducing the ability of the test to detect the target substrate. A better solution to the putative nuclease problem was required.

Protecting ETGA Substrate and IPC From Nuclease Activity

Based on the assumption that the IPC molecule should be included in LM, and that nuclease activity may be having a detrimental effect on the ETGA test, attempt was made to protect the DNA targets (IPC and ETGA substrate) from nuclease degradation. DNA can be protected from nuclease activity by various means, by modification (e.g. methylation, end modification) or using non-standard nucleotides during the synthesis of synthetic oligonucleotides (e.g. locked nucleic acids, phopsphorothioate nucleotides).

ETGA test has been found to be less sensitive to yeasts than bacteria. The reason for this not known but is likely to be due to a combination of reason such as, differences in in vitro activity or absolute quantity of the fungal enzymes in cells compared to the bacterial enzymes, or sensitivity to inhibitors.

Demonstration of the Use of PTO Oligos in the ETGA Test

Standard ETGA substrate and IPC oligos were replaced with phosphorothioate oligos (PTO) with the same nucleotide sequence in LM in the general protocol. PTO-modified ETGA substrate was added to LM at 0.01 µM and PTO-modified IPC was added at a sufficient quantity to achieve a ct value of 37-41 in a 50 cycle PCR reaction.

Figure 4A:
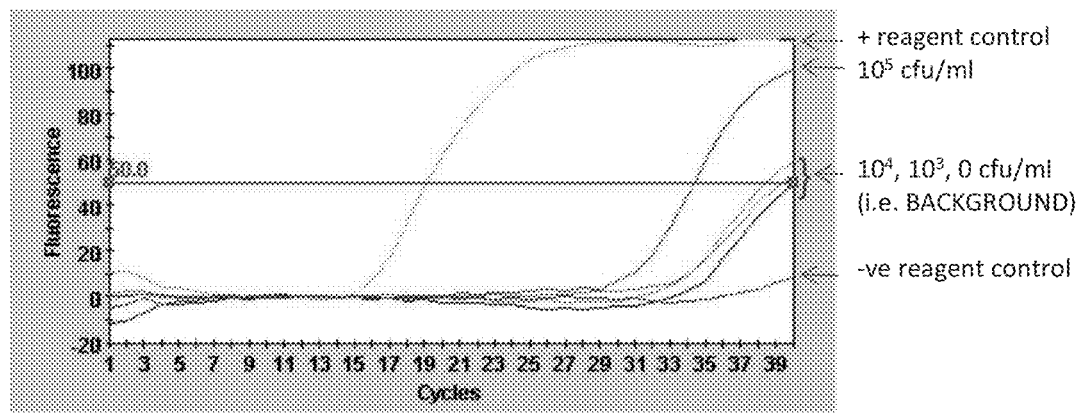
FIG. 4a shows the results of a set of ETGA tests carried out using standard substrate and IPC oligos.
Figure 4B:
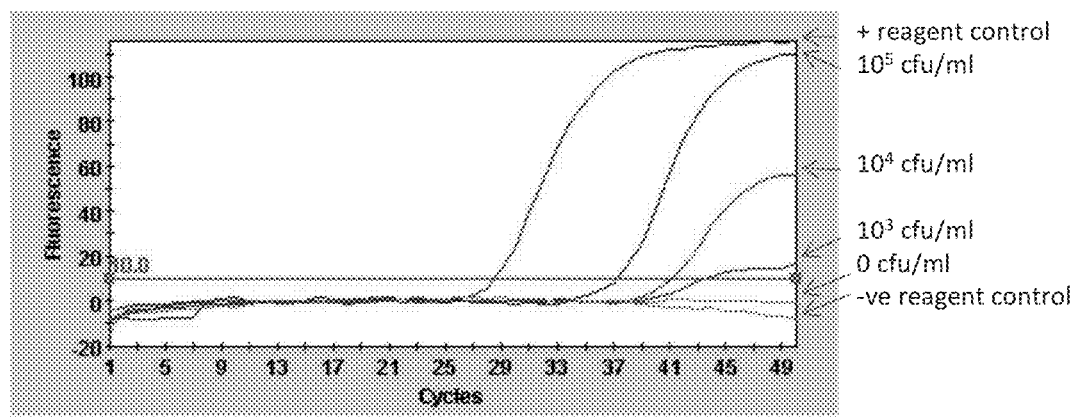
FIG. 4b shows the results obtained from exactly the same samples using PTO substrate and IPC. Note that background is much lower in FIG. 4b, and that it is possible to detect lower number of yeast cells in the test.

A dilution series of yeast cells ($10^5$, $10^4$, $10^3$ and 0 cfu/ml) in blood culture was tested with the original ETGA test protocol with standard oligos and with PTO modified oligos. Both tests were run on exactly the same spiked blood cultures (FIG. 4).

Data showed that the ETGA test with standard oligos yielded results that included high levels of background that may have occluded the detection of low levels of yeast cells, whereas results obtained with PTO modified oligos did not suffer from the same effect. In fact, results showed that PTO oligos reduced the overall background to undetectable levels on the same culture specimens, thus allowing the lowering of the threshold level in the qPCR reaction and potentially increasing the sensitivity of the ETGA test. Note that when using standard oligos, the threshold level was set at 50 units due to the amount of background fluorescence detected, but, when using the PTO oligos the threshold level could be lowered to 10 units, or lower if required. PTO oligos were detected later in the PCR reaction than when using standard oligos, but the PTO qPCR reaction could also be run for longer (50 cycles rather than 40) because the level of background was so low. The result of this reduction in background meant that lower levels of microbial load (as low as $10^3$ cfu/ml in this example) could be detected with PTO oligos that would have previously been undetectable when using the standard oligos.

Figure 5:
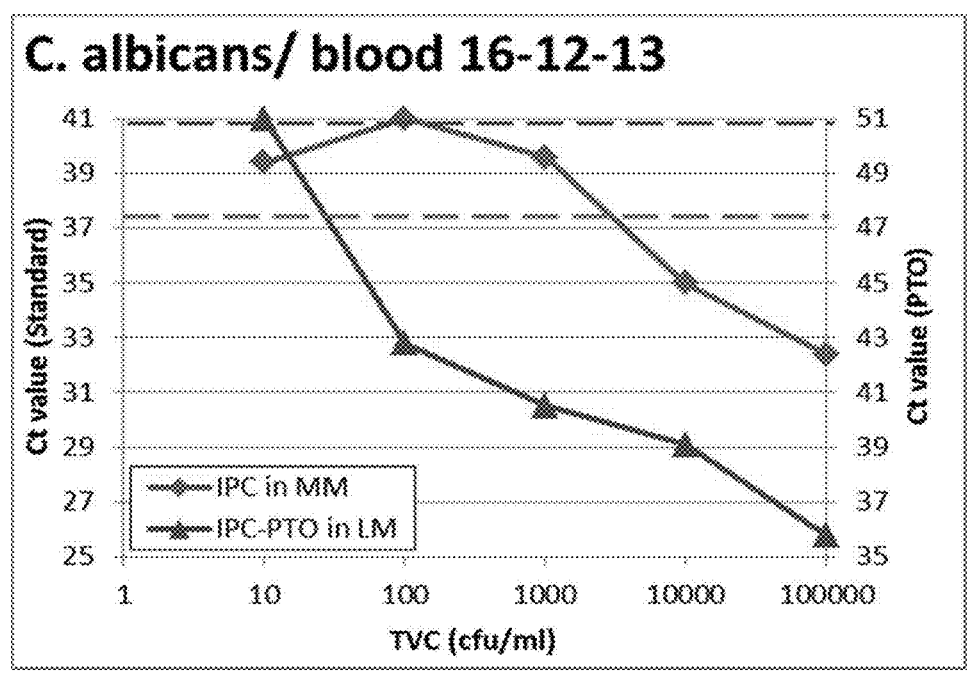
FIG. 5. Improvement of yeast detection by use of PTO oligos. Graph shows sensitivity of detection of yeast (*C. albicans*) in an ETGA test using standard oligos compared to an ETGA test using PTO oligos.

In a further experiment, nuclease resistant PTO versions of the substrate molecules (MWG-Eurofins) were used in an ETGA test. A dilution series of yeast overnight culture was used to artificially spike a blood culture (a sample of the blood culture was then spread on SDA to confirm total viable counts). Each suspension was then tested with an ETGA test using standard oligos and an ETGA test using PTO oligos. Sensitivity of detection of the yeast was much improved by the use of PTO. Note that the PTO results are plotted on a different y-axis to the standard test, due to the differing number of PCR cycles. The dashed lines indicate the Ct value of the negative control (blood culture without any microorganisms). The data from this experiment show that the PTO substrate was shown to improve the detection of yeasts (FIG. 5) by 1000-fold, and furthermore, it did not display the effect of raising background levels. The finding that a PTO substrate could be used to increase the sensitivity of the ETGA test was very significant.

Example 2—Reducing False Negative Test Results in the ETGA Test

General Protocols

For 10 mL Specimens

For each sample, 10 mL of blood culture (with or without microorganisms added, with or without blood) was mixed with 3.33 mL Reagent A (5% w/v Saponin, 5% w/v Tween 20, 8.5 g/L sodium chloride) in a 15 mL Falcon tube and incubated at room temperature for 15 min. Each sample was centrifuged for 8 min at 3600 g, then the supernatant was poured away and the rim of the tube was dabbed on clean laboratory tissue paper. Each pellet was then resupended in 5 mL of Reagent B (5 mM NaOH) and incubated for 5 min. After incubation, samples were centrifuged again and the supernatant removed by pouring away. The remaining pellet was resuspended in 1 mL of Reagent C (1.32 g/L ammonium sulphate, 0.49 g/L magnesium sulphate heptahydrate, 0.75 g/L potassium chloride, 20 mM Tris-HCl, pH8.0) and immediately transferred to a 1.5 mL microcentrifuge tube containing a mixture of glass beads. A further centrifugation for 3 min at 7300× g was carried out in order to pellet any suspended cells with the glass beads, and again, the supernatant was removed and discarded.

50 µL of microbial Lysis Mixture (LM; containing ETGA substrate see table 1 in Example 1 above) was added to the glass beads and placed in a Disruptor Genie cell disruptor for 6 min at 2800 rpm to lyse microbial cells. After disruption, samples were placed in a 37° C. heating block and incubated for 20 min, then transferred to another heating block at 95° C. and incubated for 5 min. After incubation, samples were cooled to room temperature whilst the PCR reagents were prepared.

After cooling, 3 µL of sample supernatant was added to 27 µL of PCR mastermix (MM; containing a general Taq polymerase PCR mastermix, primers for the ETGA substrate, internal positive control—IPC—DNA, FAM-labelled probe for the ETGA substrate, Texas Red labelled probe for the IPC, and UDG enzyme) in a SmartCycler PCR tube (Cepheid). Samples were placed in the SmartCycler PCR and subjected to the following reaction conditions;

1 cycle; 40° C. 10 min, 50° C. 10 min, 95° C. 5 min 40-50 cycles: 95° C. 5 sec, 61° C. 20 sec, 72° C. 20 sec.

Amplification was monitored throughout the reaction in real-time in the Texas Red and FAM excitation/detection channels of the SmartCycler.

For 1 mL Specimens

For each sample, 1 mL of blood culture was mixed with 0.333 mL Reagent A (5% w/v Saponin, 5% w/v Tween 20, 8.5 g/L sodium chloride) in a 1.5 mL microcentrifuge tube and incubated at room temperature for 15 min. Each sample was centrifuged for 3 min at 7300 g, then the supernatant was poured away and the rim of the tube was dabbed on clean laboratory tissue paper. Each pellet was then resupended in 1 mL of Reagent B (5 mM NaOH) and incubated for 5 min. After incubation, samples were centrifuged again and the supernatant removed by pouring away. The remaining pellet was resuspended in 0.5 mL of Reagent C (1.32 g/L ammonium sulphate, 0.49 g/L magnesium sulphate heptahydrate, 0.75 g/L potassium chloride, 20 mM Tris-HCl, pH8.0) and immediately transferred to a new tube containing a mixture of glass beads. A further centrifugation was carried out in order to pellet any suspended cells with the glass beads, and again, the supernatant was removed and discarded.

Microbial lysis and PCR detection was then carried out as previously described for the 10 mL protocol.

PCR reaction components and substrates are per Example 1 above.

BACKGROUND

A single clinical microbial isolate, identified as Haemophilus influenzae gave a false negative result in the ETGA test during a clinical performance evaluation. The microorganism was detected by standard automated blood culture in Biomerieux Bact/ALERT blood culture media.

Figure 6:
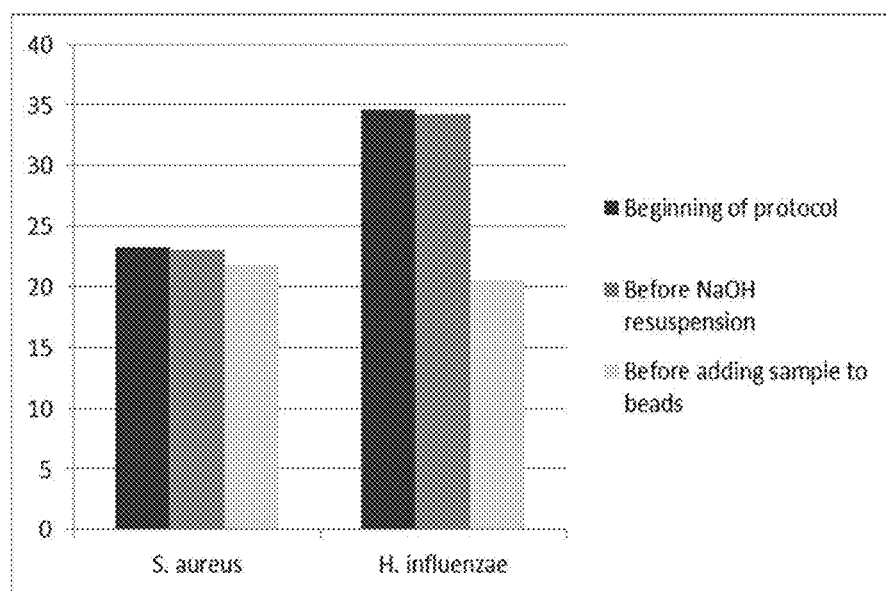
FIG. 6. Detection of less robust microorganisms by ETGA. Chart shows how detection of a delicate strain of *H. influenzae* is affected by the ETGA test procedure. Pure culture of *S. aureus* and *H. influenzae* ($10^5$ cfu) was added to the general test protocol (10 mL) at different stages. Data shows that detection was significantly reduced when microorganisms are added before the NaOH resuspension step.

When a spike of cultured microbial cells was added to different stages of the ETGA test it was found that the *H. influenzae* strain was only detected when added after the NaOH wash step (Reagent B). Other, more robust bacterial species were found to be detectable when added to the test from the start (see FIG. 6). Results indicated that the strain of *H. influenzae* was particularly sensitive to the NaOH washing step (or a combination of the steps up to and including the NaOH washing step).

This result was not typical of all strains of *H. influenzae* and, to date, has only been associated with this strain. The isolate was used as a model 'weak' organism to develop a new ETGA procedure that was better at detecting less robust microorganisms.

Incubation in NaOH is an essential step in the ETGA protocol that must be carried out in order to inactivate free polymerases, reduce contaminants and reduce background. Attempts were therefore made to reduce the damaging effect of NaOH without detrimentally affecting the test results. The concentration of NaOH could not be lowered because it did not remove sufficient contaminating material, which leads to failure of the test.

Results—Reducing Sample Exposure to NaOH

In the general 10 mL protocol, note that the time taken to centrifuge the sample increases the total time that the sample is exposed to NaOH by 8 min. Shortening the length of time could be achieved and controlled by neutralisation of the alkali, or, at least lowering the pH of the sample after an optimal period of incubation time by adding 1 mL of 200 mM Tris-HCl buffer, pH 7.2 to the NaOH.

Figure 7:
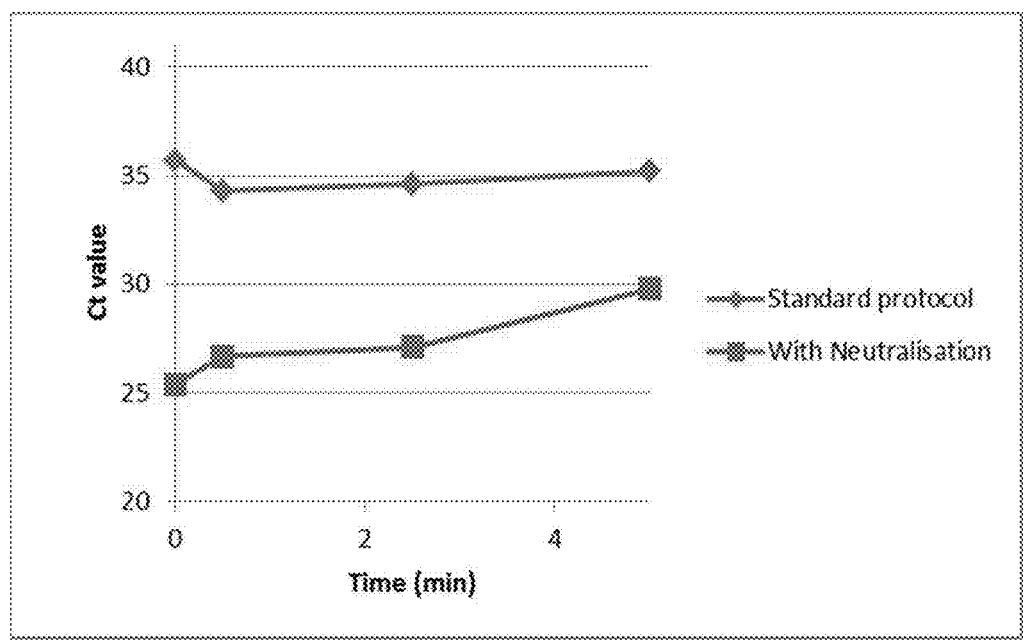
FIG. 7. Controlling exposure to NaOH to improve detection of *H. influenzae*. Graph shows the effect of controlling the amount of time that a culture sample containing $10^5$ cfu *H. influenzae* is exposed to NaOH in the ETGA test procedure compared to the standard procedure. The general protocol for 10 mL was carried out on a suspension of *H. influenzae* in BacT/ALERT broth without blood; after resuspension in NaOH and incubation for 0, 0.5, 2.5 and 5 min, 1 mL 200 mM Tris-HCl [pH7.2] was added prior to centrifugation.

The general protocol for 10 mL specimens was carried out on a suspension of *H. influenzae* in culture media drawn from a BacT/ALERT SA bottle (no blood was added). Results demonstrate that neutralisation (or significant lowering the pH) of the NaOH lead to lower ct values (from identical samples) and therefore improved sensitivity of detection (see FIG. 7).

Data also suggested that the shorter incubation time would be better, but again, short incubation times did not allow sufficient removal of contaminants to enable reliable PCR amplification, leading to reaction failure or high background levels and false positive results.

Lowering of the pH of the sample after NaOH treatment could potentially be achieved by adding any suitable buffer or acid. The preferred method of lowering the pH would be to use Reagent C (a Tris-HCl buffer, pH 8) because the reagent is already used in the test.

Results—Preferred Embodiment, 1 mL

Figure 8:
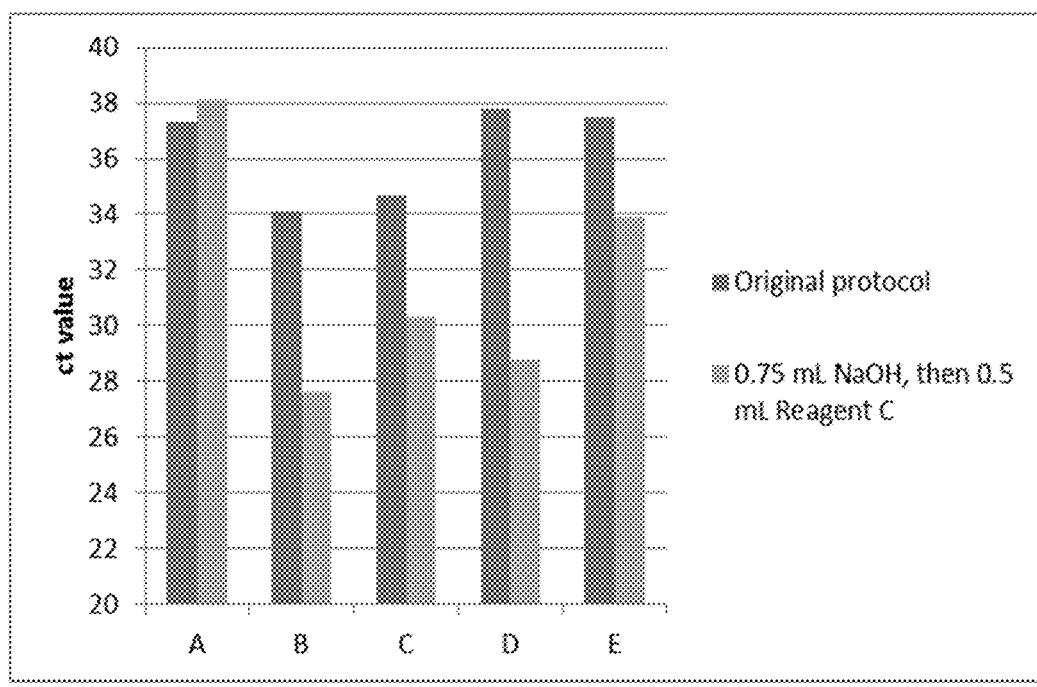
FIG. 8. Improving the 1 ml ETGA protocol with a pH lowering step. Blood culture samples containing A) no spike, B) *H. influenzae* ($10^5$ cfu), C) *H. influenzae* ($10^4$ cfu), D) *S. aureus* ($10^5$ cfu), E) *S. aureus* ($10^4$ cfu) were tested with the original 1 ml procedure (based on a resuspension in 1 mL NaOH) and a procedure containing a pH-lowering step (resuspension in 0.75 mL NaOH, 5 min incubation, 0.5 mL Reagent C). The lower ct value indicates that the microorganisms are detected more strongly.

Detection of both *H. influenzae* and *S. aureus* could be improved in the general protocol for 1 mL specimens by replacing the original NaOH step with the more complex steps consisting of resuspension in 0.75 mL NaOH, incubation at room temperature for 5 min then adding 0.5 mL Reagent C to lower the pH. Results, summarised in FIG. 8, showed that the ct values from the ETGA tests on all microorganism-containing samples were lower when using the pH-lowering protocol compared to the original 1 mL protocol, demonstrating that the pH lowering protocol improved detection.

Example 3—Analysis of the Importance of the 95° C. and the Use of a PTO Substrate Purpose The purpose of the work outlined in this example was to assess the effect of the 95° C. step on the performance of the Cognitor Minus test. The Cognitor Minus test was carried out using bacteria-spiked blood broth samples with or without the 95° C. step to compare the following characteristics:

The Ct values obtained

The stability of ETGA template DNA as measured by QPCR at different time-points following completion of sample preparation The Ct values obtained and stability of ETGA template DNA when lysis mix (LM) contains unmodified oligonucleotide (UMO) ETGA substrate as opposed to the phosphorothioate modified oligonucleotide (PTO) ETGA substrate.

INTRODUCTION

The earlier steps in the Cognitor Minus test aim to lyse blood cells and wash away blood-derived proteins such as DNA polymerases, which will produce non-microorganism derived ETGA template DNA, and nuclease enzymes which may digest microorganism-derived ETGA template DNA. Any resulting intact microorganisms are then lysed by the addition of lysis mix (LM) and bead milling. Following microorganism lysis and the ETGA reaction, samples contain a mixture of microorganism proteins, LM components, newly synthesised ETGA template DNA and residual blood cell proteins. The 95° C. step is intended to denature all proteins in order to protect the ETGA template DNA and internal process control (IPC) DNA from nuclease digestion so that it can be successfully detected by QPCR.

To assess the importance of the 95° C. step, the Cognitor Minus test was carried out using bacteria-spiked blood cultures with or without the 95° C. step. The samples were analysed by QPCR at three time points: immediately after sample preparation; after 2 hours at room temperature; and after a further 18 hours at 4° C. The aim was to compare the Ct values obtained and the consistency of Ct values across the three time points as an indicator of ETGA template DNA stability. An additional experiment was performed using LM containing UMO ETGA substrate to test whether the stability of the resulting ETGA template DNA differs from that of LM containing PTO ETGA substrate.

Materials and Methods

Reagents Used

Reagent A—5% (w/v) Saponin, 5% (v/v) Tween 20 and 146 mM Sodium chloride

Reagent B—5 mM Sodium hydroxide.

Reagent C—10 mM Ammonium sulphate, 2 mM Magnesium sulphate heptahydrate, 10 mM Potassium chloride and 20 mM Tris-HCl [pH 8.0].

Lysis Mix (LM) comprised of L1, L2, L3, dNTPs, PTO-IPC stock:

L1 (252 mL in 360 mL LM)—1.46% (w/v) BSA, 0.15% (v/v) Triton X100 and 0.15% (v/v) Tween 20;

L2 (36 mL in 360 mL LM)—100 mM Ammonium sulphate, 20 mM Magnesium sulphate heptahydrate, 100 mM Potassium chloride and 200 mM Tris-HCl [pH 8.0];

L3 (36 mL in 360 mL LM)—0.1 µM PTO-AS oligo, 0.1 µM PTO-S1 oligo, 20 mM Tris-HCl [pH 8.5], 10 mM Potassium chloride and 10 µM EDTA;

10 mM dNTPs (3.6 mL in 360 mL LM)

PTO-IPC stock (~180 µL in 360 mL LM) *Note: variable concentration $H_2O$ (~32.22 mL in 360 mL LM)

Method 1: the Cognitor Minus Test on *E. coli* Spiked Blood Broth with and without the 95° C. Step

*Escherichia coli* (ATCC® 25922™) was grown in nutrient broth for 18 hours at 37° C. BacT/ALERT SA blood broth (sheep blood) was inoculated to approximately $1 \times 10^7$ cfu/mL, $1 \times 10^6$ cfu/mL, $1 \times 10^5$ cfu/mL, $1 \times 10^4$ cfu/mL, and $1 \times 10^3$ cfu/mL with *E. coli*. Two sets of 1 ml samples were prepared for testing with or without the 95° C. step. Total viable count (TVC) plates were prepared to confirm cfu/mL values. Two sets of blood broth only 'no spike' controls (NSCs), positive controls (broth only plus DNA polymerase) and negative controls (broth only) were also prepared giving a total of 16 samples (see Table 2).

To each 1 mL sample, 330 µL Reagent A was added and mixed by five tube inversions. Samples were incubated for 15 minutes at room temperature (approximately 19° C.) and then centrifuged for 3 minutes at 7300 RCF. Following centrifugation, supernatants were decanted into a clinical waste receptacle and the open tubes blotted on sterile tissue paper. Each pellet was resuspended in 750 µL Reagent B by tip mixing and incubated for 5 minutes at room temperature. Next, 500 µL Reagent C was added to each sample and mixed by three tube inversions. Samples were centrifuged for 3 minutes at 7300 RCF. The resulting supernatants were decanted into a clinical waste receptacle and the open tubes blotted on sterile tissue paper. Each pellet was resuspended in 500 µL Reagent C by tip mixing, transferred to a beadmill tube containing glass beads (0.1 mm and 0.5 mm glass beads), and centrifuged for 3 minutes at 7300 RCF. Following centrifugation, supernatants were transferred to waste by pipette. 50 µL LM was added to each sample and an additional 10 µL of DNA Polymerase solution was added to the positive control samples. Samples were then placed into a Disruptor Genie and run for 6 min at 2800 rpm. After bead milling, samples were transferred to a heat block set at 37° C. and incubated for 20 minutes.

Following the 37° C. microorganism lysis (ETGA) step, the 95° C. (−) samples (samples 9-16) were progressed immediately to QPCR setup, whilst the 95° C. (+) samples (samples 1-8) were incubated at 95° C. for 5 minutes prior to QPCR setup. Both sets of samples were analysed by QPCR immediately. The same samples were analysed by QPCR again after 2 hours at room temperature (approximately 19° C.), and again after a further 18 hours at 4° C. This experiment was replicated four times to allow statistical analysis of the results.

TABLE 2

| Test Samples |
|---|
| 95° C. (+) Samples |

1. *E. coli* $1 \times 10^7$ cfu/mL
2. *E. coli* $1 \times 10^6$ cfu/mL
3. *E. coli* $1 \times 10^5$ cfu/mL

TABLE 2-continued

Test Samples

4. E. coli 1 × 10⁴ cfu/mL
5. E. coli 1 × 10³ cfu/mL
6. Blood broth only (NSC)
7. Positive control (Pol + ve)
8. Negative control (Pol − ve)

95° C. (−) Samples

9. E. coli 1 × 10⁷ cfu/mL
10. E. coli 1 × 10⁶ cfu/mL
11. E. coli 1 × 10⁵ cfu/mL
12. E. coli 1 × 10⁴ cfu/mL
13. E. coli 1 × 10³ cfu/mL
14. Blood broth only (NSC)
15. Positive control (Pol + ve)
16. Broth only (Pol − ve)

NSC: No spike control

Method 2: PTO ETGA Substrate Vs UMO ETGA Substrate

BacT/ALERT blood broth SA was inoculated to approximately 1×10⁷ cfu/mL and 1×10⁴ cfu/mL with E. coli. Four sets of 1 ml samples were prepared to compare Cognitor Minus test results with and without the use of PTOs, with and without the 95° C. step. TVC plates were prepared to confirm cfu/mL values. NSCs and positive controls were also prepared (see Table 3). All samples were processed according to the general protocol described above in "Method 1". Following the 37° C. microorganism lysis (ETGA) step, the 95° C. (−) samples (samples 9-16) were progressed immediately to QPCR setup, whilst the 95° C. (+) samples (samples 1-8) were incubated at 95° C. for 5 minutes before QPCR setup. Both sets of samples were analysed by QPCR immediately. The same samples were analysed by QPCR after 2 hours at room temperature, and again following a further 18 hours at 4° C.

TABLE 3

Test Samples

95° C. (+) Samples

1. E. coli 1 × 10⁷ cfu/mL: UMO LM
2. E. coli 1 × 10⁷ cfu/mL: PTO LM
3. E. coli 1 × 10⁴ cfu/mL: UMO LM
4. E. coli 1 × 10⁴ cfu/mL: PTO LM
5. Blood broth only (NSC): UMO LM
6. Blood broth only (NSC): PTO LM
7. Positive control (Pol + ve): UMO LM
8. Positive control (Pol + ve): PTO LM

95° C. (−) Samples

Figure 9A:
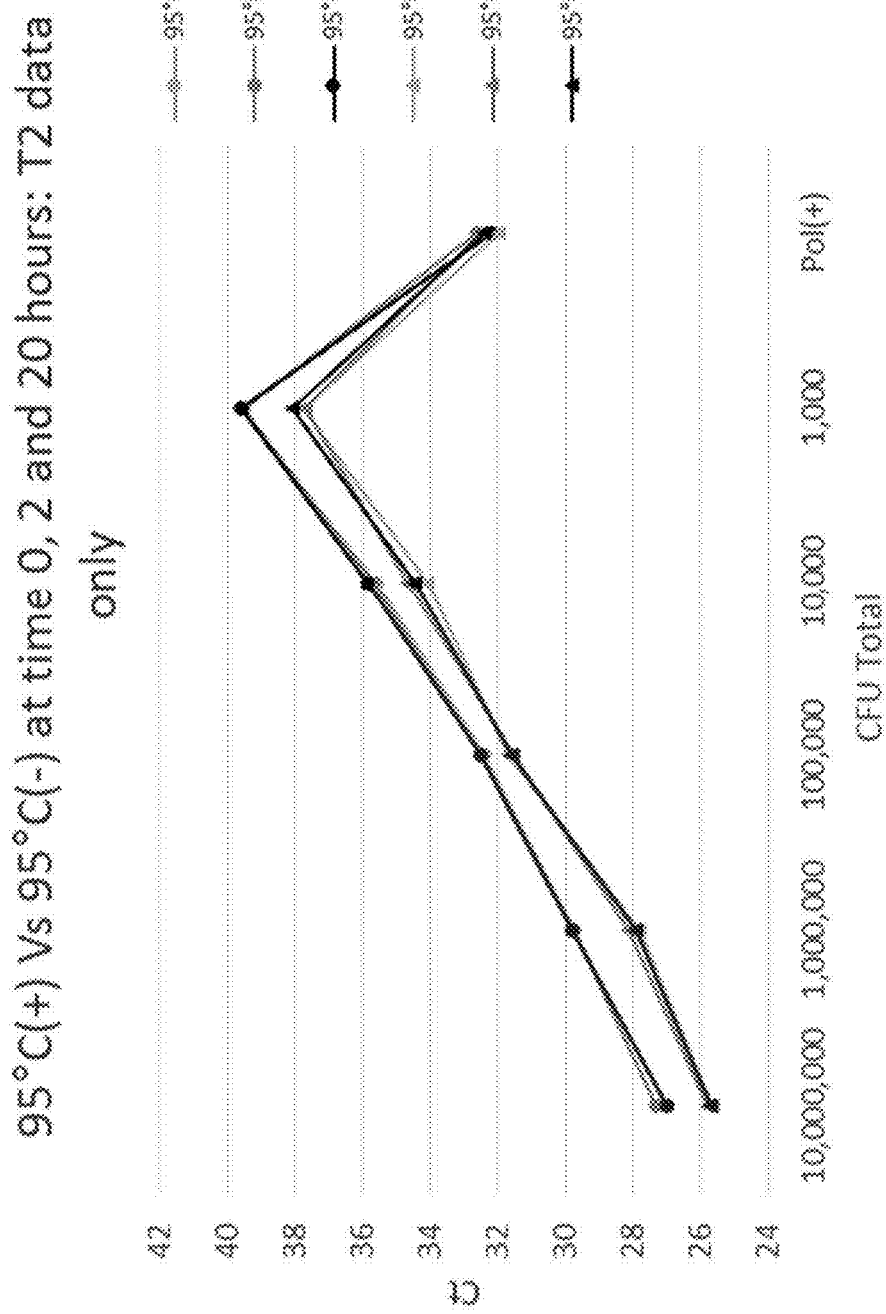
FIGS. 9A-C. Cognitor Minus results for *E. coli* spiked blood broth samples and the positive control (Pol(+)). Data is shown for Cognitor Minus samples analysed at time 0, 2 and 20 hours with or without the 95° C. step for (A) experiment 2, (B) experiment 3 and (C) experiment 4. Data for experiment 1 is not shown because samples were only analysed by QPCR at time 0 hours.
Figure 9B:
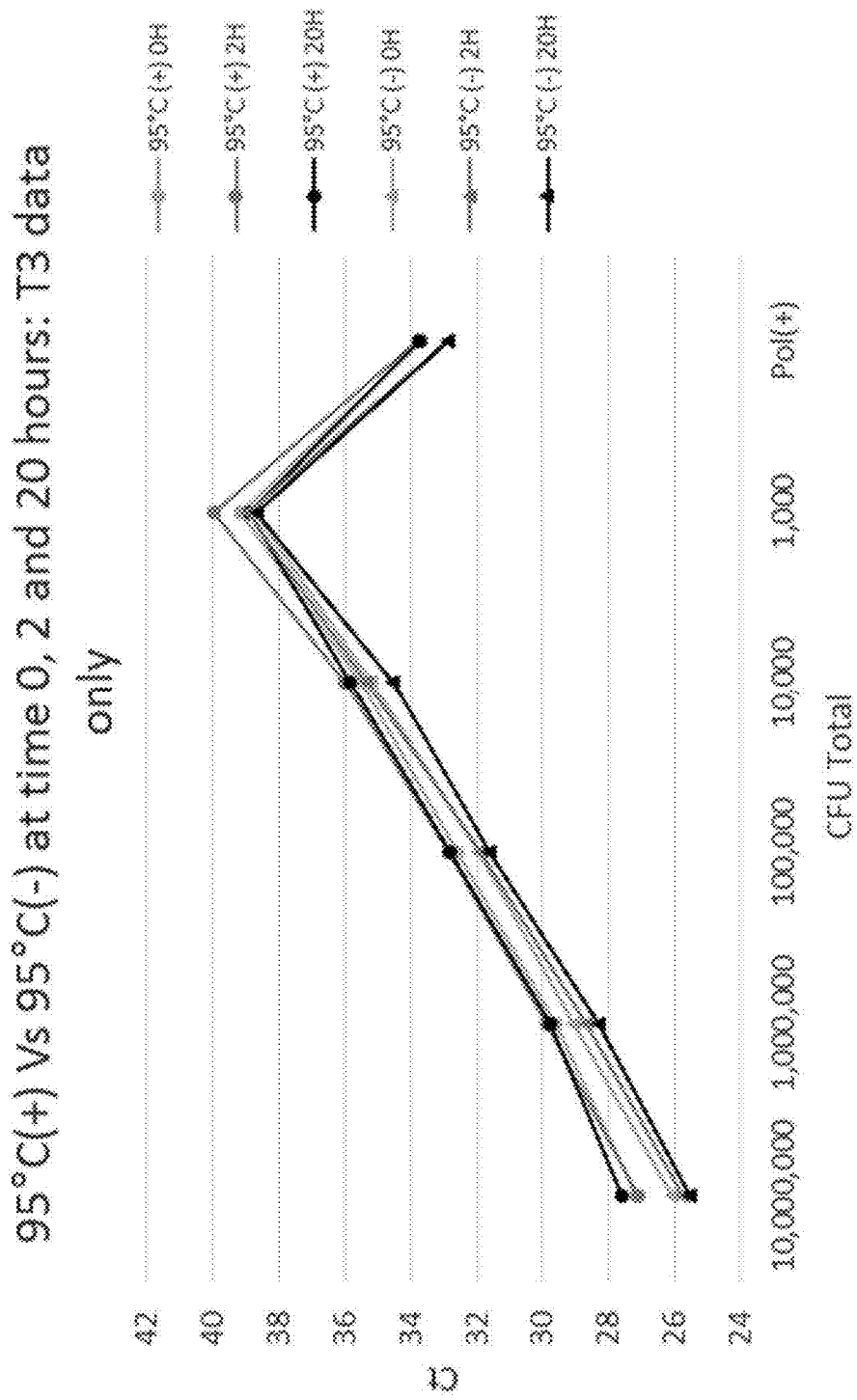
Figure 9C:
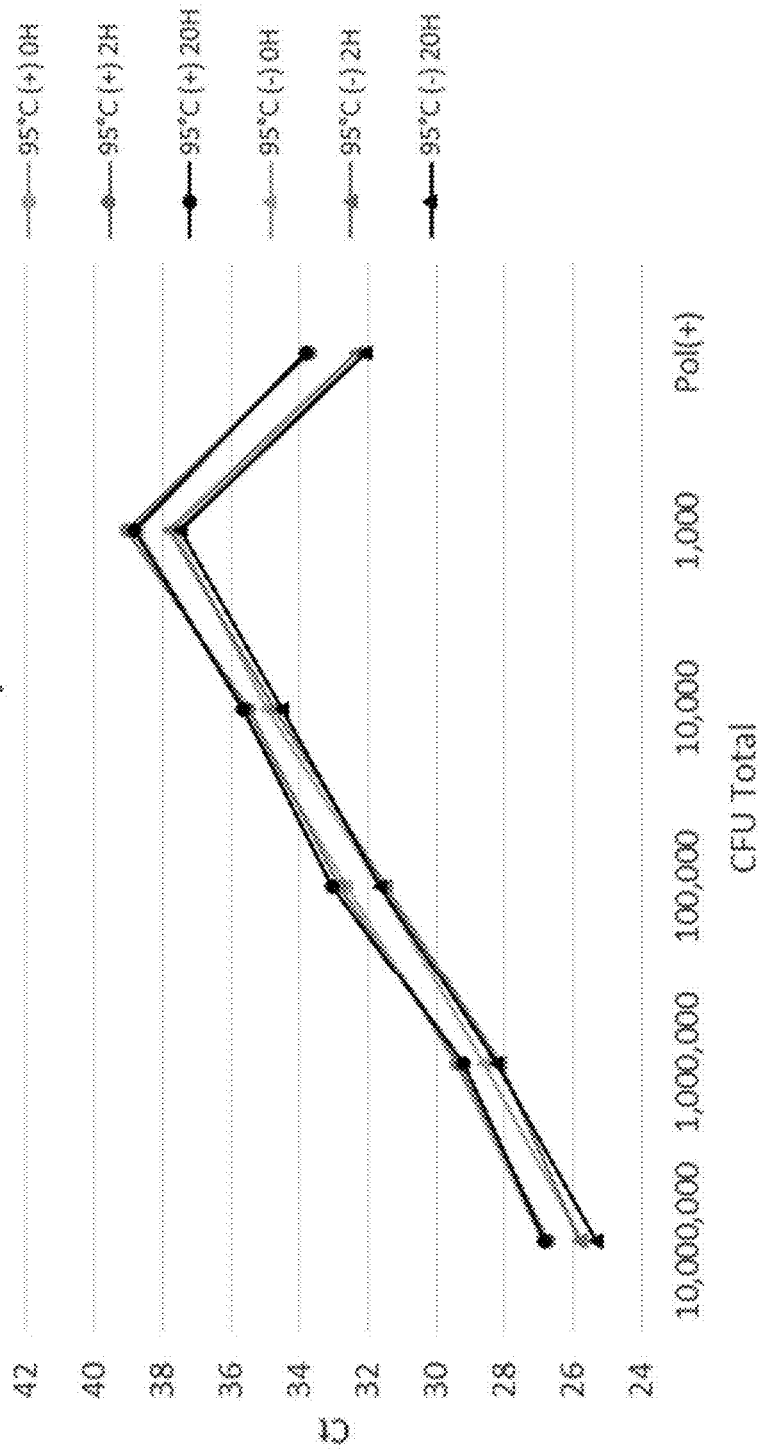
Figure 10:
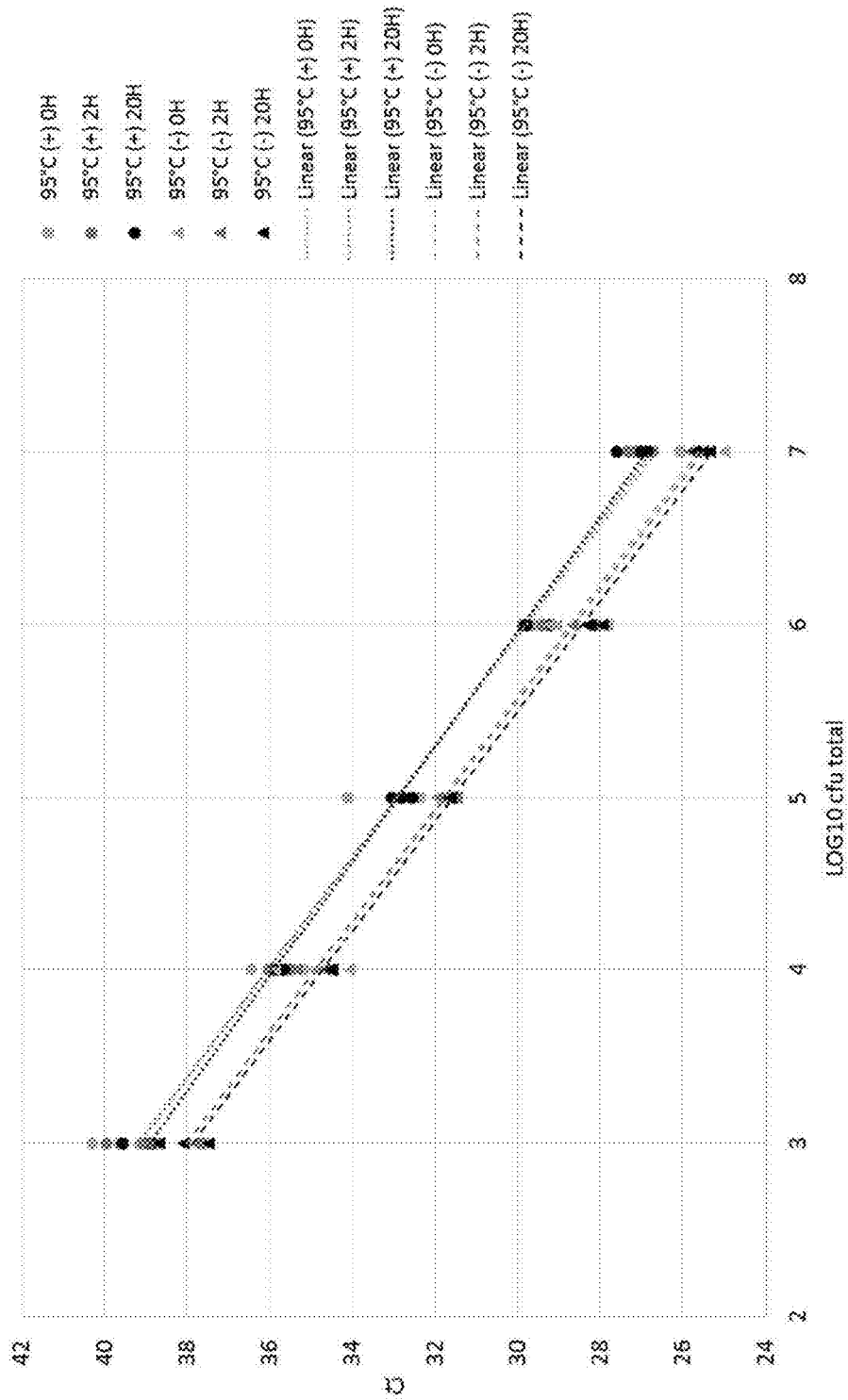
FIG. 10. Ct values for *E. coli* spiked blood broth samples (n=4) plotted against log transformed total cfu values. Trend lines are plotted for each time point (0 hours, 2 hours and 20 hours) within the 95° C. (+) or 95° C. (−) data sets. Positive control data is not shown here.

9. E. coli 1 × 10⁷ cfu/mL: UMO LM
10. E. coli 1 × 10⁷ cfu/mL: PTO LM
11. E. coli 1 × 10⁴ cfu/mL: UMO LM
12. E. coli 1 × 10⁴ cfu/mL: PTO LM
13. Blood broth only (NSC): UMO LM
14. Blood broth only (NSC): PTO LM
15. Positive control (Pol + ve): UMO LM
16. Positive control (Pol + ve): PTO LM NSC: no spike control,
UMO: unmodified oligonucleotide,
PTO: phosphorothioate oligonucleotide,
LM: lysis mix Results and Discussion Results 1: Removal of the 95° C. Step Improves ETGA QPCR Signal without a Reduction in Signal Over Time The results for samples processed with or without the 95° C. step at time 0, 2 and 20 hours following sample preparation (n=3) are shown in FIGS. 9A-C. Within individual experiments, removal of the 95° C. step resulted in reduced Ct values (increased ETGA signal) for all E. coli spiked blood broth dilutions and positive controls (FIGS. 9A-C). The Ct values obtained for the same samples at time 0, 2 and 20 hours are highly consistent across the three replicate experiments with maximum ΔCt values ranging from 0.07 Ct units to 1.07 Ct units (average maximum ΔCt value of 0.30 Ct units) for 95° C. (+) samples and maximum ΔCt values ranging from 0.03 Ct units to 0.58 Ct units (average maximum ΔCt value of 0.38 Ct units) for 95° C. (−) samples. All NSCs and negative controls yielded Ct values greater than 40 or had no QPCR amplification at all (data not shown). FIG. 10 shows all of the data for E. coli spiked blood broth samples plotted together and several trends are apparent. Firstly, there is a clear difference between the Ct values obtained for 95° C. (+) samples compared to 95° C. (−) samples, with approximately a 1.0 Ct unit reduction in Ct values for 95° C. (−) samples. Secondly, there is very little difference between the Ct values obtained at different time points for both 95° C. (+) and 95° C. (−) samples. However, there is a small reduction in Ct value as storage time increases when the 95° C. step is removed, which is apparent from the trend lines in FIG. 10 and is more pronounced in experiment 3 (FIG. 9B).

Linear modelling was performed (using R) to determine whether there are statistically significant differences between the Ct values obtained for the E. coli spiked blood broth dilution series with or without the 95° C. step and at different time points. Table 4 shows the p-values obtained for different comparisons. Comparison of Ct values for 95° C. (+) samples with 95° C. (−) samples using data from all four experiments produced highly significant p-values ($p<0.001$) regardless of whether data from individual time points or data from all time points were included in the analysis. Comparison of Ct values for different time points within 95° C. (+) or 95° C. (−) datasets using data from all four experiments produced non-significant p-values ($p>0.05$). Time point comparisons within the same experiment produced non-significant p-values ($p>0.05$) for all datasets apart from the 95° C. (−) dataset in experiment 3 (T3), which had a p-value of 0.016. This significant p-value is likely to be due to the more pronounced reduction in Ct value with time that was observed in this particular experiment.

TABLE 4

Linear Models (using R) to compare Ct value standard curves for the E. coli spiked blood culture dilution series at different time points and with or without the 95° C. step.

| Data analysed | Comparison | P-value | Significance |
| --- | --- | --- | --- |
| All data | 95° C. (+) vs 95° C. (−) | $<2 \times 10^{-16}$ | *** |
| Time 0 H: T1-T4 data | 95° C. (+) vs 95° C. (−) | $4.82 \times 10^{-8}$ | *** |
| Time 2 H: T2-T4 data | 95° C. (+) vs 95° C. (−) | $1.31 \times 10^{-8}$ | *** |
| Time 20 H: T2-T4 data | 95° C. (+) vs 95° C. (−) | $1.47 \times 10^{-10}$ | *** |
| 95° C. (+): T1-T4 data | Time | 0.730 | — |
| 95° C. (−): T1-T4 data | Time | 0.094 | — |
| 95° C. (+): T2 data only | Time | 0.896 | — |
| 95° C. (−): T2 data only | Time | 0.657 | — |
| 95° C. (+): T3 data only | Time | 0.956 | — |
| 95° C. (−): T3 data only | Time | 0.016 | * |

TABLE 4-continued

Linear Models (using R) to compare Ct value standard curves for the *E. coli* spiked blood culture dilution series at different time points and with or without the 95° C. step.

| Data analysed | Comparison | P-value | Significance |
|---|---|---|---|
| 95° C. (+): T4 data only | Time | 0.769 | — |
| 95° C. (−): T4 data only | Time | 0.061 | — |

Significance codes:
* p < 0.05,
** p < 0.01,
*** p < 0.001.
—: not significant.
T: experiment.

Figure 11A:
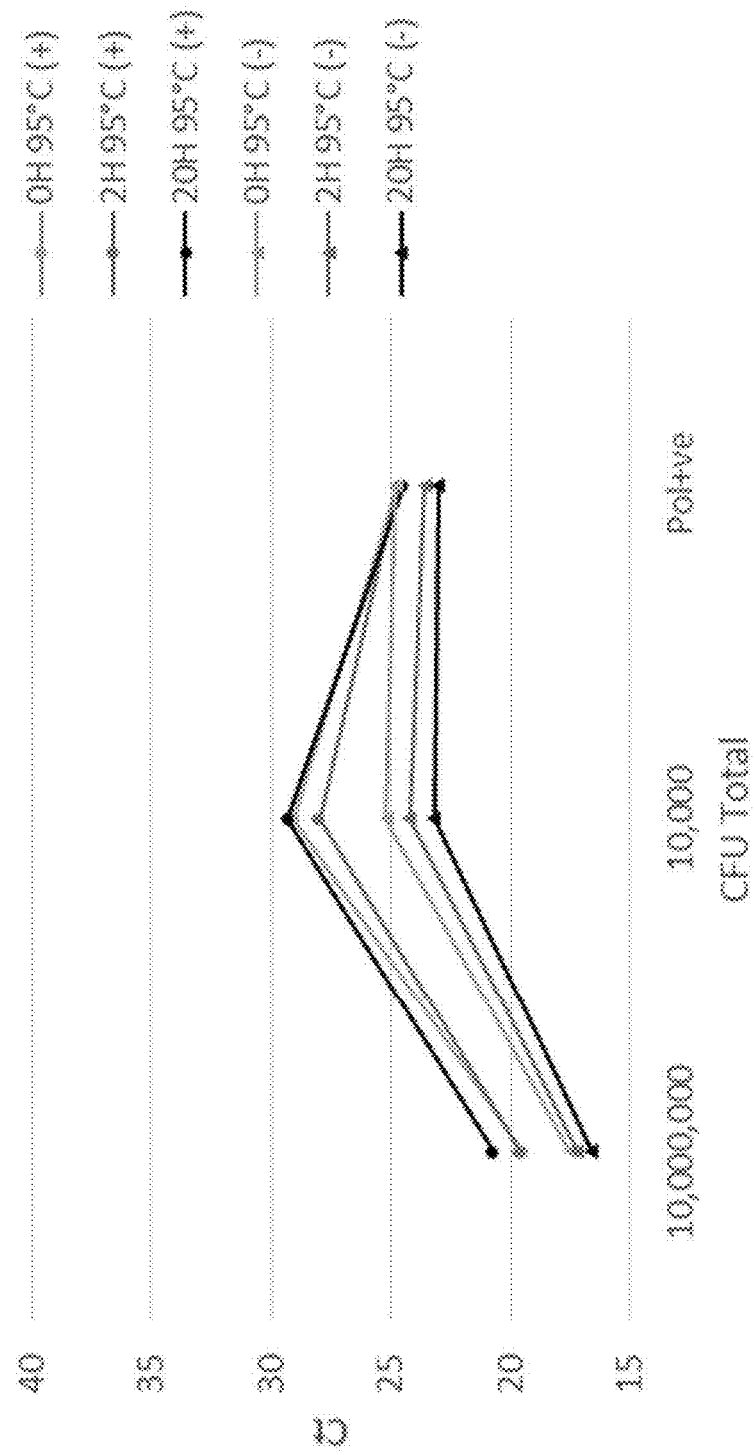
FIGS. 11A-B. Ct values for *E. coli* spiked blood broth samples and positive controls (Pol+ve) at time 0, 2 and 20 hours for 95° C. (+) and 95° C. (−) samples processed using either (A) unmodified oligonucleotide lysis mix or (B) phosphorothioate oligonucleotide lysis mix. The data shown is from a single experiment (n=1).
Figure 11B:
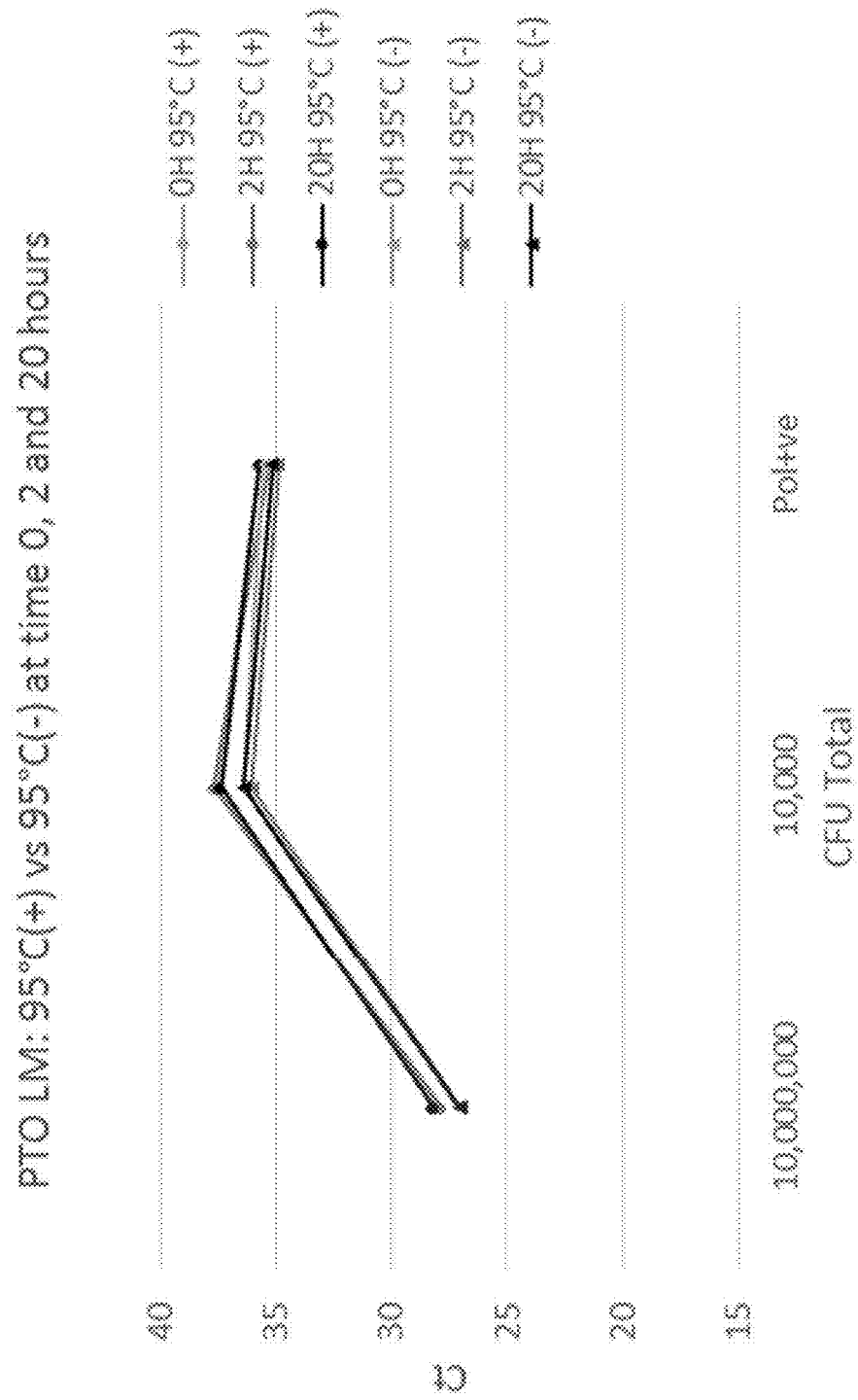
Figure 12A:
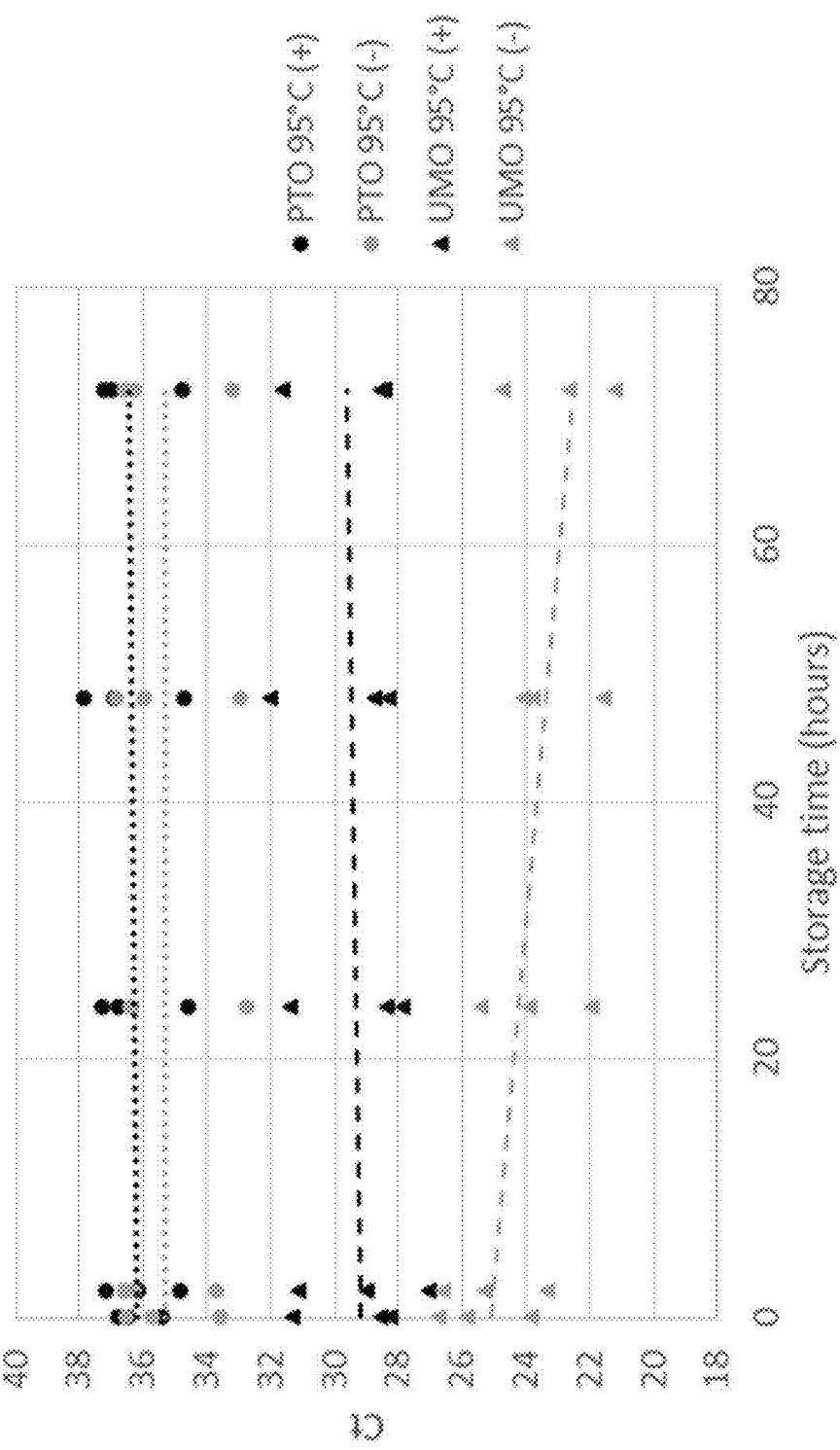
Figure 12B:
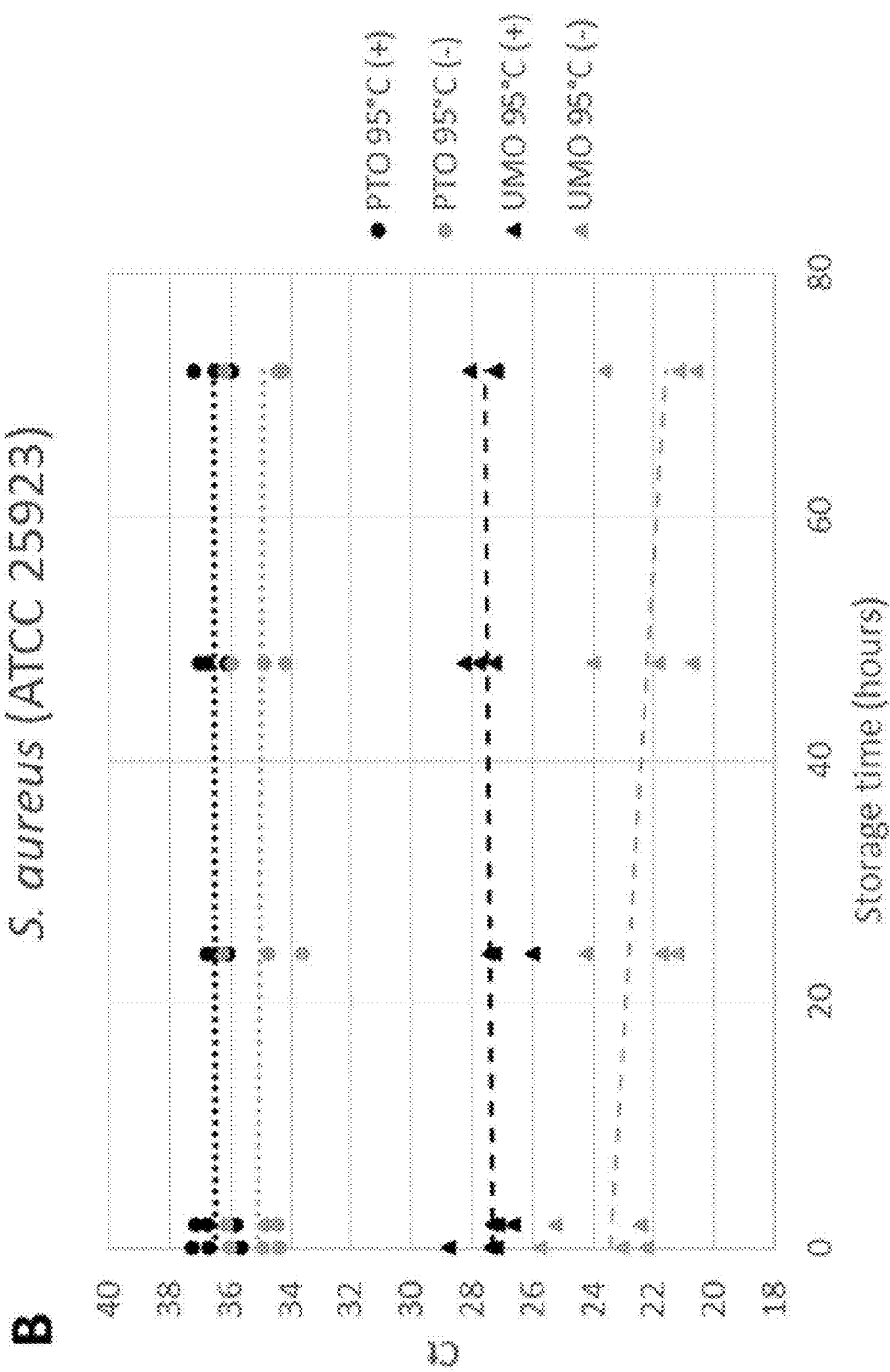
Figure 12C:
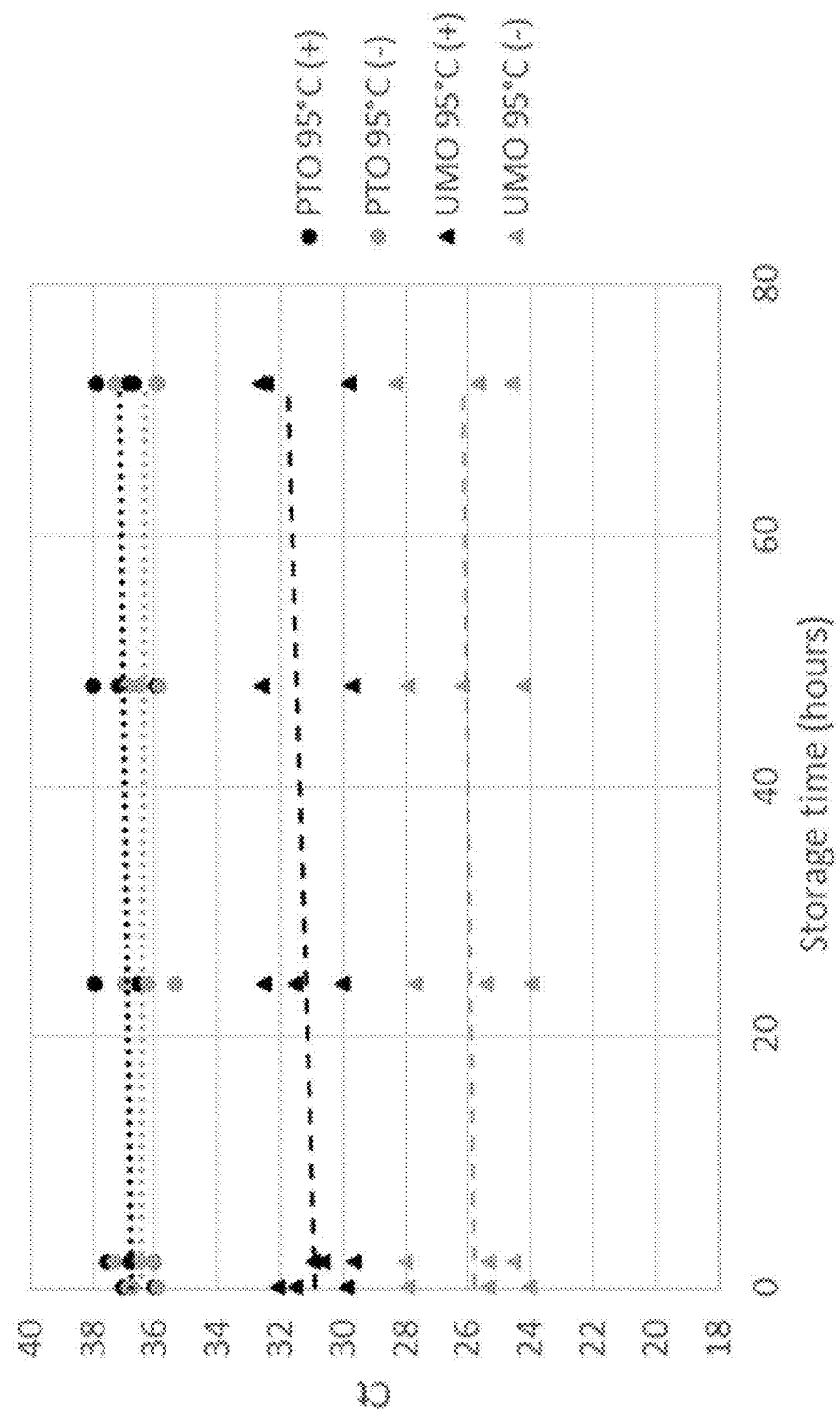
Figure 12D:
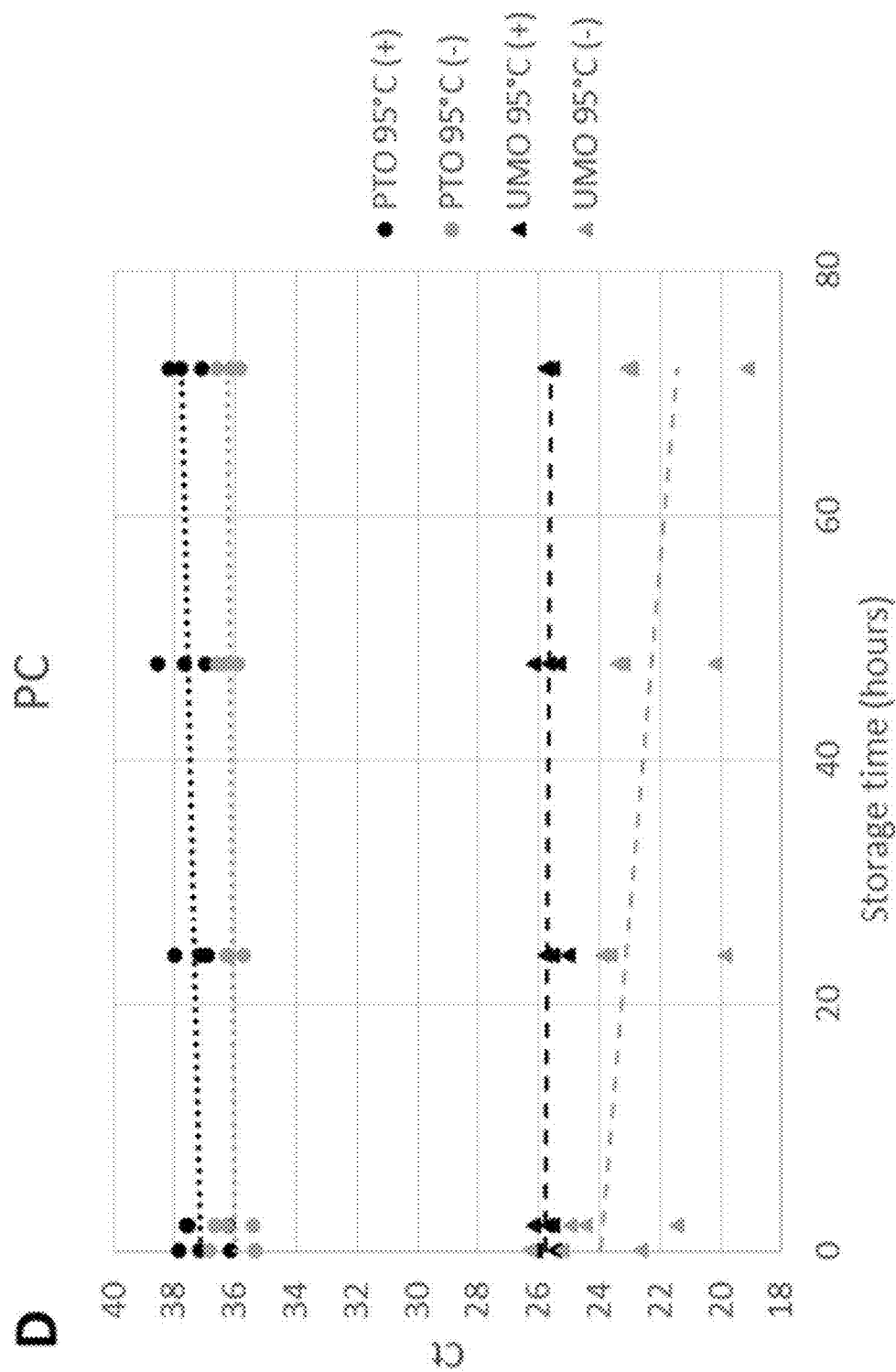
Figure 12E:
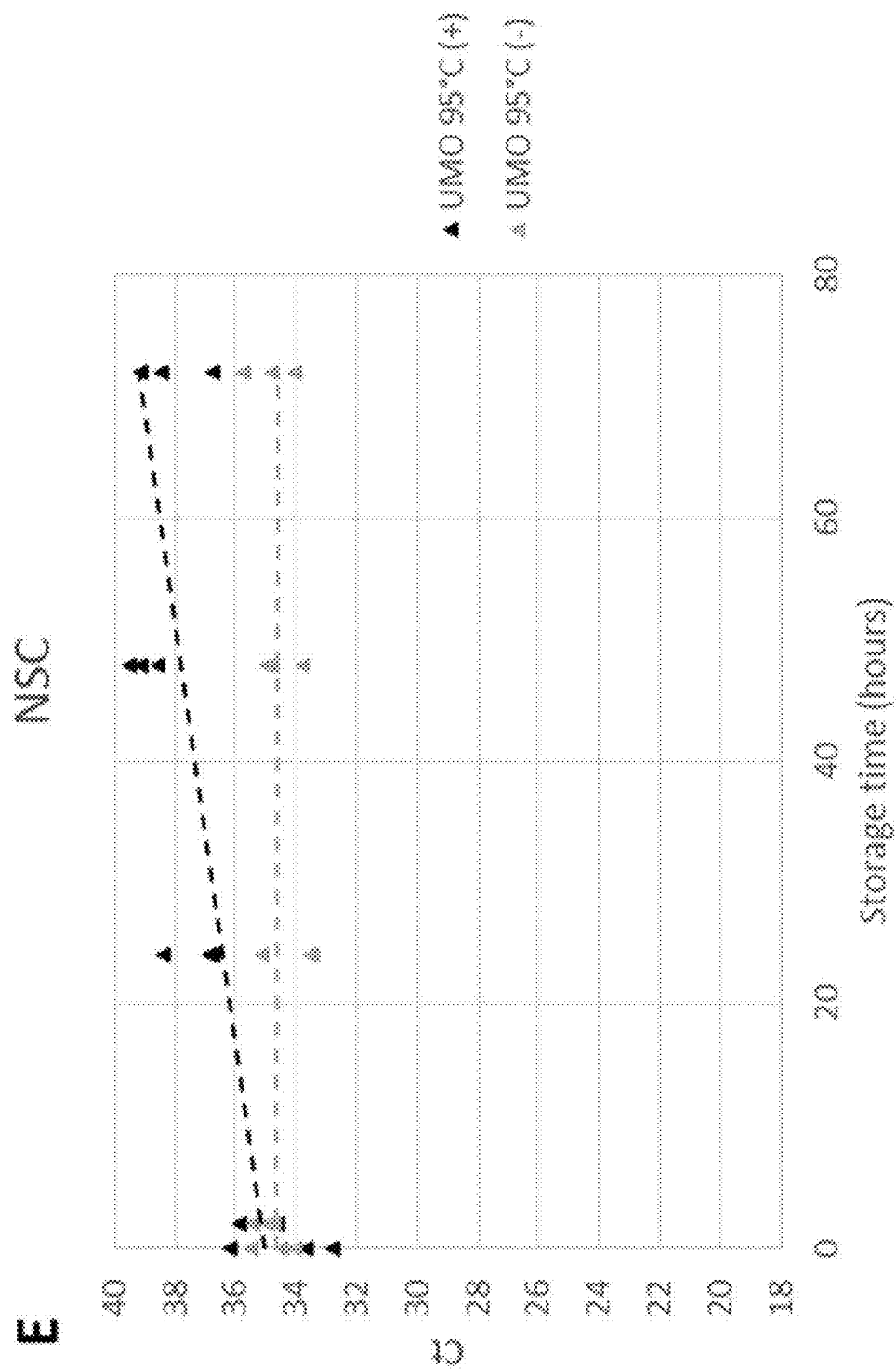

Results 2: Cognitor Minus Results are More Consistent Across Different Time Points when Using PTO LM Rather than UMO LM FIGS. 11A-B shows the Ct values obtained for *E. coli* spiked blood broth samples ($1 \times 10^7$ cfu/mL and $1 \times 10^4$ cfu/mL) and positive controls processed using either UMO LM (FIG. 11A) or PTO LM (FIG. 11B) with and without the 95° C. step. The data shown here is from a single experiment. The Ct values for NSCs using UMO LM were all at least 5 Ct units higher than the Ct values obtained for $1 \times 10^3$ cfu/mL *E. coli* spiked blood broth samples, whilst the PTO LM NSC Ct values were all greater than 42.0 Ct units or had no QPCR amplification at all (data not shown). The results demonstrate that the Ct values for UMO LM samples are on average 10.2 Ct units lower than the Ct values for PTO LM samples. There is also a greater reduction in Ct value for UMO LM samples than there is for PTO LM samples when the 95° C. step is removed. Most importantly, in relation to ETGA template DNA stability, the Ct values obtained for UMO LM samples are notably less consistent across the different time points than the Ct values for PTO LM samples. The Ct values for *E. coli* spiked blood broth samples in the UMO LM 95° C. (+) dataset increased by approximately 1.0 Ct unit from 2 hours to 20 hours, whilst the corresponding positive control showed a 0.24 Ct unit reduction in Ct value. This indicates that nuclease digestion of ETGA template DNA may be occurring in samples when bacteria and/or host blood cells are present despite the protein denaturing effect of the 95° C. step, but not in the positive control were only DNA polymerase enzyme is added. When the 95° C. step is removed, the Ct values for UMO LM samples decrease with increased sample storage time. This indicates that in the absence of protein denaturation, continued ETGA template generation may out compete any increase in nuclease digestion, hence resulting in increased ETGA QPCR signal. The PTO LM data (FIG. 11B) demonstrate highly consistent Ct values across all time points for both 95° C. (+) and 95° C. (−) samples. These data indicate that ETGA template DNA formed from PTO substrate DNA is more resistant to change by either nuclease degradation and/or additional ETGA template DNA generation following the 37° C. ETGA reaction.

SUMMARY

The data shown here demonstrate that ETGA template DNA detection is improved when the 95° C. step is removed. Furthermore, ETGA QPCR signal does not deteriorate with increased sample storage time in the absence of the 95° C. step. Comparison of PTO LM with UMO LM indicates that the high stability of ETGA template DNA is dependant of the use of PTO ETGA substrate DNA. All of the data shown here support removal of the 95° C. step from the Cognitor Minus test. It is worth noting that the increased sensitivity of the test may increase the chance of detecting background signal (blood-derived ETGA signal), however, optimisation of other factors such as blood lysis/wash performance and interpretation of QPCR results should eliminate the impact of this.

Example 4—Analysis of the Importance of the 95° C. and the Use of a PTO Substrate: Primary Panel Microorganisms Purpose The purpose of the work presented in this report was to:
1. Compare Cognitor Minus results with and without the 95° C. step for all primary panel microorganisms (*E. coli*; *S. aureus*; and *C. albicans*)
2. Confirm the findings of Example 3 with regard to comparison between phosphorothioate modified oligonucleotide (PTO) LM and unmodified oligonucleotide (UMO) LM
3. Test the effect of extended sample storage duration (up to 72 hours) on QPCR results for each primary panel microorganism using PTO LM and UMO LM

INTRODUCTION

The earlier steps in the Cognitor Minus test aim to lyse blood cells and wash away blood-derived proteins such as DNA polymerases, which will produce non-microorganism derived ETGA template DNA, and nuclease enzymes which may digest microorganism-derived ETGA template DNA. This process should not harm any microorganisms that are present in the blood sample. Isolated intact microorganisms are then lysed by the addition of lysis mix (LM) and bead milling. After microorganism lysis and the ETGA reaction, samples contain a mixture of microorganism proteins, LM components, newly synthesised ETGA template DNA and residual blood cell proteins. In the current Cognitor Minus test protocol, the 95° C. step is intended to denature all proteins in order to protect ETGA template DNA and internal process control (IPC) DNA from nuclease digestion so that it can be successfully detected by QPCR. The 95° C. step also inactivates DNA polymerases, thereby quenching the ETGA reaction. However, since incorporating the 95° C. step into the protocol, the UMOs used to form the ETGA substrate (and IPC) in the LM have been replaced with PTOs which are nuclease resistant. Whilst the ETGA extension strand that forms the ETGA template is constructed from standard dNTPs, the PTO substrate DNA that it is annealed to may confer protection against nuclease digestion. Due to the benefits of removing the 95° C. step, such as protocol simplification and a reduction in the time required to run the test, it was deemed important to re-evaluate the necessity of the 95° C. step.

To assess the importance of the 95° C. step, the Cognitor Minus test was carried out using microorganism-spiked blood broth with or without the 95° C. step. Samples were analysed by QPCR at five time points: immediately after sample preparation; after 2 hours stored at room temperature (approximately 19° C.); and after 24 hours, 48 hours and 72 hours stored at 4° C. The Ct values obtained and consistency of Ct values across the five time points were used to assess the effect of the 95° C. step on Cognitor Minus test performance and sample stability for each of the primary panel microorganisms using either PTO LM or UMO LM.

Materials and Methods

For details of reagents, see Example 3.

*Escherichia coli* (ATCC® 25922™), *Staphylococcus aureus* (ATCC® 25923™) and *Candida albicans* (ATCC® 10231™) were grown in liquid media (*E. coli* and *S. aureus* in nutrient broth; and *C. albicans* in Sabouraud media) for approximately 18 hours at 37° C. BacT/ALERT SA blood broth (sheep blood; see Table 6) was inoculated with *E. coli*, *S. aureus* and *C. albicans* to approximately $1 \times 10^4$ cfu/mL, $1 \times 10^4$ cfu/mL and $1 \times 10^5$ cfu/mL respectively. Four sets of 1 ml samples were prepared for testing with or without the 95° C. step for PTO LM and UMO LM. Blood broth only 'no spike' controls (NSCs) and positive controls (broth only plus DNA polymerase (PC)) were also prepared giving a total of 20 samples (see Table 5). Total viable count (TVC) plates were prepared to confirm cfu/mL values (see Table 7) and negative blood broth.

To each 1 mL sample, 330 µL Reagent A was added and mixed by five tube inversions. Samples were incubated for 15 minutes at room temperature (approximately 19° C.) and then centrifuged for 3 minutes at 7300 RCF. Following centrifugation, supernatants were decanted into a clinical waste receptacle and the open tubes blotted on sterile tissue paper. Each pellet was resuspended in 750 µL Reagent B by tip mixing and incubated for 5 minutes at room temperature. Next, 500 µL Reagent C was added to each sample and mixed by three tube inversions. Samples were centrifuged for 3 minutes at 7300 RCF. The resulting supernatants were decanted into a clinical waste receptacle and the open tubes blotted on sterile tissue paper. Each pellet was resuspended in 500 µL Reagent C by tip mixing, transferred to a beadmill tube containing glass beads (0.1 mm and 0.5 mm glass beads), and centrifuged for 3 minutes at 7300 RCF. Following centrifugation, supernatants were transferred to waste by pipette. 50 µL LM was added to each sample and an additional 10 µL of DNA Polymerase solution was added to the positive control samples. Samples were then placed into a Disruptor Genie and run for 6 min at 2800 rpm. After bead milling, samples were transferred to a heat block set at 37° C. and incubated for 20 minutes.

Following the 37° C. microorganism lysis (ETGA) step, the 95° C. (−) samples (samples 11-20) were progressed immediately to QPCR setup, whilst the 95° C. (+) samples (samples 1-10) were incubated at 95° C. for 5 minutes prior to QPCR setup. Both sets of samples were analysed by QPCR immediately. The same samples were analysed by QPCR again after 2 hours at room temperature, and again after 24 hours, 48 hours and 72 hours at stored at 4° C. This experiment was replicated three times to allow for statistical analysis of the results.

TABLE 5

Test Samples

95° C. (+) Samples

1. *E. coli* $1 \times 10^4$ cfu/mL: PTO LM
2. *S. aureus* $1 \times 10^4$ cfu/mL: PTO LM
3. *C. albicans* $1 \times 10^5$ cfu/mL: PTO LM
4. PC: PTO LM
5. NSC: PTO LM
6. *E. coli* $1 \times 10^4$ cfu/mL: UMO LM
7. *S. aureus* $1 \times 10^4$ cfu/mL: UMO LM
8. *C. albicans* $1 \times 10^5$ cfu/mL: UMO LM
9. PC: UMO LM
10. NSC: UMO LM 95° C. (−) Samples TABLE 5-continued Test Samples 11. *E. coli* $1 \times 10^4$ cfu/mL: PTO LM
12. *S. aureus* $1 \times 10^4$ cfu/mL: PTO LM
13. *C. albicans* $1 \times 10^5$ cfu/mL: PTO LM
14. PC: PTO LM
15. NSC: PTO LM
16. *E. coli* $1 \times 10^4$ cfu/mL: UMO LM
17. *S. aureus* $1 \times 10^4$ cfu/mL: UMO LM
18. *C. albicans* $1 \times 10^5$ cfu/mL: UMO LM
19. PC: UMO LM
20. NSC: UMO LM PC: positive control,
NSC: no spike control,
UMO: unmodified oligonucleotide,
PTO: phosphorothioate oligonucleotide,
LM: lysis mix

TABLE 6

Materials

| Reagent | Supplier | Batch/Lot number | Expiry date |
|---|---|---|---|
| Sheep Blood (Replicate 1) | TCS Bioscience | 30112000 | 27 Apr. 2015 |
| Sheep Blood (Replicate 2) | TCS Bioscience | 30210900 | 25 May 2015 |
| Sheep Blood (Replicate 3) | TCS Bioscience | 30255300 | 8 Jun. 2015 |

TABLE 7

Microorganism TVCs

| Microorganism | Exp. 1 TVC (cfu total) | Exp. 2 TVC (cfu total) | Exp. 3 TVC (cfu total) |
|---|---|---|---|
| *E. coli* | 7,200 | 10,200 | 28,200 |
| *S. aureus* | 4,200 | 23,000 | 23,200 |
| *C. albicans* | 271,000 | 191,000 | 246,000 |

Results and Discussion

The results for samples processed using either PTO LM or UMO LM with or without the 95° C. step at time 0, 2, 24, 48 and 72 hours (n=3) are shown in FIGS. 12A-E.

Removal of the 95° C. Step Improves ETGA QPCR Signal

All microorganism-spiked blood broth samples and positive control samples processed without the 95° C. step produced lower Ct values (stronger ETGA signal) than corresponding samples processed with the 95° C. step, for both PTO LM and UMO LM. The average ΔCt values (95° C. (+) subtract 95° C. (−)) for PTO LM samples at '0 hours' were 0.98 Ct units, 1.41 Ct units, 0.12 Ct units and 1.21 Ct units for *E. coli*, *S. aureus* and *C. albicans* and positive control respectively. The average ΔCt values (95° C. (+) subtract 95° C. (−)) for UMO LM samples at '0 hours' were 3.91 Ct units, 4.10 Ct units, 5.36 Ct units and 1.20 Ct units for *E. coli*, *S. aureus* and *C. albicans* and positive control respectively. The majority of NSC samples processed with PTO LM did not produce Ct values due to low QPCR amplification, and therefore this data is not shown in FIGS. 12A-E. However, the incidence of sufficient amplification for Ct values was higher for 95° C. (−) samples than 95° C. (+) samples (7/15 Ct values compared to 2/15 Ct values with no obvious trends for storage duration; and all NSC PTO LM Ct values were between 42.0 Ct units and 45.0 Ct units).

NSC samples processed with UMO LM produced Ct values at '0 hours' that were on average 0.42 Ct units lower without the 95° C. step. This increase in QPCR signal for NSC samples processed without the 95° C. step is expected given the general increase in signal observed for positive samples.

Cognitor Minus Results are More Consistent Across Different Time Points when Using PTO LM Rather than UMO LM Within the PTO LM dataset, all microorganism-spiked blood broth samples and positive control samples produced highly consistent Ct values across the 72 hour storage period, regardless of whether samples were processed with the 95° C. step. Within the UMO LM 95° C. (+) dataset, E. coli, S. aureus and positive control samples produced fairly consistent Ct values across the 72-hour storage period, whereas C. albicans and NSC samples showed an increase in Ct values over time (reduction in ETGA signal). This increase in Ct values for C. albicans and NSC samples may be due to a greater impact of nuclease activity on ETGA template DNA concentration when the starting concentration is lower, as indicated by higher Ct values for these samples at '0 hours'. UMO LM 95° C. (−) samples generally showed a decrease in Ct value (increase in ETGA QPCR signal) over time, except for C. albicans and NSC samples were Ct values were highly consistent across the 72-hour period. This indicates that for E. coli, S. aureus and positive control samples processed without the 95° C. step (protein denaturation), continuation of the ETGA reaction results in increased QPCR signal, out competing any nuclease activity. Whereas, in C. albicans and NSC samples, where the effect of nuclease degradation seems to be more pronounced, the continued ETGA reaction may be counteracting this degradation to provide more stable QPCR signal over time.

Statistical Analysis of Results

Linear modelling was performed (using R) to determine whether there are statistically significant differences between the Ct values obtained for PTO LM and UMO LM samples processed with or without the 95° C. step at different time points. For each dataset (e.g. E. coli with PTO LM dataset), 'Ct' was modelled against the following explanatory variables and their interactions: 'Log 10 cfu', 'Time', and '95° C. step'. Non-significant ($p>0.05$) interactions and variables were removed from the model in a stepwise manner, resulting in model simplification. However, non-significant variables were not removed from the model if any of their interactions were significant ($p<0.05$). Therefore, the final model for each dataset contained only significant interactions, significant variables, and non-significant variables that form significant interactions. Significance codes for each variable and interaction are shown in Table 8 (significance codes are based on p-values for each interaction or variable at the point of model simplification, if removed from the model, or from the final model).

TABLE 8

Significance codes for p-values of each explanatory variable and their interactions using linear modelling in R

| Dataset | Log10 cfu | Time | 95° C. | Log10 cfu: Time | Log10 cfu: 95° C. | Time: 95° C. | Log10 cfu: Time: 95° C. |
|---|---|---|---|---|---|---|---|
| E. coli PTO LM | *** | NS | *** | NS | ~ | NS | NS |
| E. coli UMO LM | *** | ** | *** | NS | NS | * | NS |
| S. aureus PTO LM | *** | NS | * | NS | ** | NS | NS |
| S. aureus UMO LM | *** | *** | *** | NS | *** | ** | NS |
| C. albicans PTO LM | * | NS | *** | NS | ** | NS | NS |
| C. albicans UMO LM | ~ | NS | ** | NS | ** | NS | NS |
| PC PTO LM | | ~ | *** | | | NS | |
| PC UMO LM | | ~ | *** | | | ~ | |
| NSC UMO LM | | NS | NS | | | *** | |

Significance codes:
*** $p < 0.001$,
** $p < 0.01$,
* $p < 0.05$,
~ $p < 0.1$,
NS—not significant.

The 95° C. step has a significant effect on Ct value for all microorganisms and positive controls with PTO LM and UMO LM. Sample storage duration ('Time' and 'Time' interactions) has no significant effect on Ct value for any microorganism or positive control with PTO LM; and is also non-significant for C. albicans and the positive control with UMO LM. However, sample storage duration is a significant variable for E. coli and S. aureus with UMO LM: most likely due to the observed reduction in Ct value over time for samples processed without the 95° C. step in these sample sets. There is no significant effect of the 95° C. step for the NSC UMO LM dataset; but there is a significant interaction between sample storage duration and the 95° C. step (Time: 95° C.'). Statistical analysis could not be performed on the NSC PTO LM dataset due to missing Ct values as a result of low QPCR amplification.

SUMMARY

The data shown here demonstrate that ETGA template DNA detection is improved when the 95° C. step is removed. Furthermore, ETGA QPCR signal does not deteriorate with increased sample storage duration in the absence of the 95° C. step when samples are processed using PTO ETGA substrate DNA. ETGA signal is not as stable when samples are processed using UMO ETGA substrate DNA: in the absence of the 95° C. step ETGA QPCR signal continues to increase with sample storage duration; and with the 95° C. step ETGA QPCR signal is more likely to deteriorate as a result of nuclease degradation without continued production of ETGA template DNA. These results are consistent with the results presented in Example 3.

All of the data shown here support removal of the 95° C. step from the Cognitor Minus test, and confirm the importance of using PTO ETGA substrate DNA in the LM. These results also verify that samples processed using PTO LM can be stored for up to 72 hours at 4° C., without being detrimental to test results. It is worth noting that the increased sensitivity of the test upon removal of the 95° C. step may increase the chance of detecting background signal (blood-derived ETGA QPCR signal). However, whilst NSC PTO LM samples did not provide a complete set of Ct values for comparison (due to low amplification), the NSC UMO LM dataset demonstrates that the increase in ETGA QPCR signal associated with removal of the 95° C. is lower for NSCs than it is for positive samples. Furthermore, optimisation of other factors such as blood lysis/wash performance and interpretation of QPCR results should eliminate the impact of this.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

Various publications are cited herein, the disclosures of which are incorporated by reference in their entireties.

The invention claimed is:

1. A method of detecting the presence of a micro-organism in a sample, the method comprising:
   (a) contacting the sample with a nuclease resistant nucleic acid molecule comprising a plurality of nuclease resistant nucleotides which is either extended by polymerase activity or is ligated by ligase activity of the micro-organism in the sample, wherein the nuclease resistant nucleotides comprise phosphorothioate nucleotides,
   (b) incubating the thus contacted sample under conditions suitable for polymerase activity or ligase activity; and
   (c) detecting in the sample a nucleic acid molecule that has been extended by the polymerase activity or ligated by the ligase activity of the micro-organism as compared to a negative control, thereby indicating the presence of the micro-organism in the sample.

2. The method of claim 1 wherein the action of the polymerase activity or ligase activity on the nuclease resistant nucleic acid molecule produces an extended nucleic acid molecule.

3. The method of claim 1 wherein step (a) comprises contacting the sample with a nucleic acid molecule which is either extended by polymerase activity or is ligated by ligase activity of the micro-organism in the sample together with an internal positive control (IPC) nucleic acid molecule, wherein:
   (a) the IPC nucleic acid molecule is susceptible to nuclease activity and is used to identify contaminating nuclease activity in the sample; or
   (b) the IPC nucleic acid molecule is nuclease resistant and comprises a plurality of nucleotides that are resistant to nuclease activity.

4. The method of claim 3 wherein a nucleic acid probe is added in step (c) which binds to a target probe sequence within the nucleic acid molecule, optionally wherein the nucleic acid probe is labelled.

5. The method of claim 4 wherein a further nucleic acid probe is added in step (c) which binds to a target probe sequence within the IPC nucleic acid molecule, optionally wherein the further nucleic acid probe is labelled.

6. The method of claim 5 wherein the nucleic acid probe does not bind to the IPC nucleic acid molecule and the further nucleic acid probe does not bind to the nucleic acid molecule.

7. The method of claim 5 wherein the nucleic acid probe and further nucleic acid probe are differently labelled.

8. The method of claim 1 wherein the nucleic acid molecule is at least partially double stranded and comprises uracil residues in the complementary strand and step (c) comprises adding Uracil DNA Glycosylase (UDG) to the sample in order to degrade the uracil residues in the complementary strand.

9. The method of claim 8 wherein the complementary strand of the nucleic acid molecule comprises a modification at the 3' end to prevent extension.

10. The method of claim 9 wherein the modification at the 3' end comprises incorporation of a non-extendible nucleotide.

11. The method of claim 10 wherein the non-extendible nucleotide is a dideoxy nucleotide triphosphate (ddNTP), optionally wherein the ddNTP is dideoxyCytidine.

12. The method of claim 1 wherein step (c) comprises a nucleic acid amplification step.

13. The method of claim 1, wherein the sample contains a non-micro-organism source of polymerase activity or ligase activity, and the method comprises:

(a) treating the sample under high pH conditions for no more than 5 minutes in order to inhibit the non-microorganism source of polymerase activity or ligase activity,
(b) contacting the sample with the nuclease resistant nucleic acid molecule comprising a plurality of the nuclease resistant nucleotides which is either extended by polymerase activity or is ligated by ligase activity of the micro-organism in the sample,
(c) incubating the thus contacted sample under conditions suitable for polymerase activity or ligase activity; and
(d) specifically determining the presence of a modified nucleic acid molecule resulting from the action of the polymerase activity or ligase activity on the nuclease resistant nucleic acid molecule to indicate the presence of the micro-organism.

14. The method of claim 13 wherein the treatment under high pH conditions is stopped by adding a reagent to lower the pH.

15. The method of claim 1 wherein the sample contains a non-micro-organism source of polymerase activity or ligase activity, and the method comprises:
(a)
  (i) incubation of the sample with a reagent that lyses non-microorganisms if present in the sample but does not lyse microorganisms in the sample,
  (ii) separation of the lysed cell material and the intact microorganisms if any in the sample,
  (iii) contacting the separated intact microorganisms if any in the sample with a high pH reagent and incubating for no more than 5 minutes in order to inhibit the non-micro-organism source of polymerase activity or ligase activity,
  (iv) adding a pH lowering reagent in order to stop the incubation at high pH,
  (v) separation of the microorganisms if present in the sample from the pH modifying reagents,
  (vi) lysis of any separated microorganisms,
  (vii) contacting the sample with the nuclease resistant nucleic acid molecule comprising the plurality of nuclease resistant nucleotides which is either extended by polymerase activity or is ligated by ligase activity of the micro-organism in the sample,
  (viii) incubating the thus contacted sample under conditions suitable for polymerase activity or ligase activity, and
  (ix) specifically determining the presence of the extended or ligated nucleic acid molecule resulting from the action of the polymerase activity or ligase activity on the nuclease resistant nucleic acid molecule to indicate the absence or presence of the micro-organism;
or
(b)
  (i) incubation of the sample with a reagent that lyses non-micro-organisms if present in the sample but does not lyse micro-organisms in the sample,
  (ii) centrifugation of the sample to form a pellet containing micro-organisms if present in the sample,
  (iii) removal of the supernatant from the pellet,
  (iv) re-suspending the pellet in a high pH reagent and incubating for no more than 8 minutes in order to inhibit the non-micro-organism source of polymerase activity or ligase activity,
  (v) adding a pH lowering reagent in order to stop the incubation at high pH,
  (vi) a second centrifugation of the sample to form a pellet containing micro-organisms if present in the sample,
  (vi) removal of the supernatant from the pellet,
  (vii) lysing any micro-organisms in the pellet,
  (viii) contacting the sample with the nuclease resistant nucleic acid molecule comprising the plurality of nuclease resistant nucleotides which is either extended by polymerase activity or is ligated by ligase activity of the micro-organism in the sample,
  (ix) incubating the thus contacted sample under conditions suitable for polymerase activity or ligase activity, and
  (x) specifically determining the presence of the extended or ligated nucleic acid molecule resulting from the action of the polymerase activity or ligase activity on the nuclease resistant nucleic acid molecule to indicate the presence of the micro-organism.

16. The method of claim 15 wherein steps (a)(vi) and (a)(vii) or b(vii) and b(viii) are performed together, optionally wherein the nucleic acid molecule is added to the sample together with a lysis reagent.

17. The method of claim 1 wherein the sample potentially contains a non-micro-organism source of nuclease activity and the method comprises:
  (i) incubation of the sample with a reagent that lyses non-micro-organisms if present in the sample but does not lyse micro-organisms in the sample,
  (ii) separation of the lysed cell material from the intact microorganisms if any in the sample and/or inactivation of the lysed cell material,
  (iii) lysing any microorganisms following the separation and/or inactivation,
  (iv) contacting the sample with the nuclease resistant nucleic acid molecule comprising a plurality of the nuclease resistant nucleotides which is either extended by polymerase activity or ligated by ligase activity of the micro-organism in the sample,
  (v) incubating the thus contacted sample under conditions suitable for polymerase activity or ligase activity, and
  (vi) specifically determining the presence of the extended or ligated nucleic acid molecule resulting from the action of the polymerase activity or ligase activity on the nuclease resistant nucleic acid molecule to indicate the presence of the micro-organism;
or
(a) centrifugation of the sample to form a pellet containing micro-organisms if present in the sample,
(b) removal of the supernatant from the pellet,
(c) lysing any micro-organisms in the pellet,
(d) contacting the sample with the nuclease resistant nucleic acid molecule comprising the plurality of nuclease resistant nucleotides which is either extended by polymerase activity or is ligated by ligase activity of the micro-organism in the sample,
(e) incubating the thus contacted sample under conditions suitable for polymerase activity or ligase activity, and
(f) specifically determining the presence of the extended or ligated nucleic acid molecule resulting from the action of the polymerase activity or ligase activity on the nuclease resistant nucleic acid molecule to indicate the presence of the micro-organism.

18. The method of claim 17 wherein steps (iii) and (iv) or (c) and (d) respectively are performed together, optionally wherein the nuclease resistant nucleic acid molecule comprising a plurality of nuclease resistant nucleotides is added to the sample together with a lysis reagent.

19. A method of detecting the absence of a micro-organism in a sample, the method comprising:
(a) contacting the sample with a nuclease resistant nucleic acid molecule comprising a plurality of nuclease resistant nucleotides which is either extended by polymerase activity or is ligated by ligase activity of the micro-organism in the sample, wherein the nuclease resistant nucleotides comprise phosphorothioate nucleotides,
(b) incubating the thus contacted sample under conditions suitable for polymerase activity or ligase activity; and
(c) detecting in the sample a lack of a nucleic acid molecule that has been extended by the polymerase activity or ligated by the ligase activity of the micro-organism as compared to a positive control, thereby indicating the absence of the micro-organism in the sample.

20. The method of claim 19 wherein the positive control is an internal positive control (IPC).

21. The method of claim 19 wherein the nucleic acid molecule is at least partially double stranded and comprises uracil residues in the complementary strand and step (c) comprises adding Uracil DNA Glycosylase (UDG) to the sample in order to degrade the uracil residues in the complementary strand.

22. The method of claim 21 wherein the complementary strand of the nucleic acid molecule comprises a modification at the 3' end to prevent extension.

23. The method of claim 19 wherein step (c) comprises a nucleic acid amplification step.

* * * * *

```
                          SEQUENCE LISTING

<160> NUMBER OF SEQ ID NOS: 7

<210> SEQ ID NO 1
<211> LENGTH: 35
<212> TYPE: DNA
<213> ORGANISM: Artificial Sequence
<220> FEATURE:
<223> OTHER INFORMATION: Exemplary Sequence of Molecular Beacon Probe
      for Detecting Amplification Product

<400> SEQUENCE: 1
cgctgcgacc gaccgataag ctagaacagg cagcg                          35

<210> SEQ ID NO 2
<211> LENGTH: 34
<212> TYPE: DNA
<213> ORGANISM: Artificial Sequence
<220> FEATURE:
<223> OTHER INFORMATION: Exemplary Sequence of Molecular Beacon Probe
      for Detecting Amplification Produc

<400> SEQUENCE: 2
cgcgatcagc aggccacacg ttaaagacat cgcg                           34

<210> SEQ ID NO 3
<211> LENGTH: 99
<212> TYPE: DNA
<213> ORGANISM: Artificial Sequence
<220> FEATURE:
<223> OTHER INFORMATION: Exemplary Internal Positive Control (IPC)
      Nucleic Acid Molecule in Nucleic Acid Amplification Reaction

<400> SEQUENCE: 3
gccgatatcg gacaacggcc gaactgggaa ggcgagatca gcaggccaca cgttaaagac    60
agagagacaa caacgctggc cgtttgtcac cgacgccta                           99

<210> SEQ ID NO 4
<211> LENGTH: 26
<212> TYPE: DNA
<213> ORGANISM: Artificial Sequence
<220> FEATURE:
<223> OTHER INFORMATION: Exemplary Primer for Detecting Modified
      Substrate Probe

<400> SEQUENCE: 4
ccgatatcgg acaacggccg aactgg                                    26

<210> SEQ ID NO 5
<211> LENGTH: 25
<212> TYPE: DNA
<213> ORGANISM: Artificial Sequence
```

```
<220> FEATURE:
<223> OTHER INFORMATION: Exemplary Primer for Detecting Modified
      Substrate Probe

<400> SEQUENCE: 5
taggcgtcgg tgacaaacgg ccagc                                          25

<210> SEQ ID NO 6
<211> LENGTH: 37
<212> TYPE: DNA
<213> ORGANISM: Artificial Sequence
<220> FEATURE:
<223> OTHER INFORMATION: Exemplary Substrate Probe for Detecting Nucleic
      Acid Modifying Activity

<400> SEQUENCE: 6
uaggcgucgg ugacaaacgg ccagcguugu ugucucu                             37

<210> SEQ ID NO 7
<211> LENGTH: 74
<212> TYPE: DNA
<213> ORGANISM: Artificial Sequence
<220> FEATURE:
<223> OTHER INFORMATION: Exemplary Substrate Probe for Detecting Nucleic
      Acid Modifying Activity

<400> SEQUENCE: 7
gccgatatcg gacaacggcc gaactgggaa ggcgagactg accgaccgat aagctagaac    60
agagagacaa caac                                                      74
```